US012704512B2

(12) United States Patent
Krammer et al.

(10) Patent No.: US 12,704,512 B2
(45) Date of Patent: Aug. 11, 2026

(54) MODULATORS OF THE FUNCTION OF THE CORE DOMAIN OF ANNEXINS, AND USES THEREOF IN AUTOIMMUNE AND/OR CANCER THERAPY

(71) Applicant: Deutsches Krebsforschungszentrum Stiftung des öffentlichen Rechts, Heidelberg (DE)

(72) Inventors: Peter H. Krammer, Heidelberg (DE); Alexandra Kurz, Kiel (DE); Bjorn Linke, Jena (DE); Heiko Weyd, Heidelberg (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 1465 days.

(21) Appl. No.: 15/541,709

(22) PCT Filed: Nov. 19, 2015

(86) PCT No.: PCT/EP2015/077066
§ 371 (c)(1),
(2) Date: Jul. 6, 2017

(87) PCT Pub. No.: WO2016/113022
PCT Pub. Date: Jul. 21, 2016

(65) Prior Publication Data

US 2018/0275124 A1 Sep. 27, 2018

(30) Foreign Application Priority Data

Jan. 15, 2015 (EP) .................................... 15151328

(51) Int. Cl.

| | |
|---|---|
| ***G01N 33/566*** | (2006.01) |
| ***A61K 38/00*** | (2006.01) |
| ***A61K 39/35*** | (2006.01) |
| ***C07K 14/47*** | (2006.01) |
| ***C07K 16/18*** | (2006.01) |
| ***G01N 33/564*** | (2006.01) |
| ***G01N 33/575*** | (2026.01) |

(52) U.S. Cl.
CPC .......... *G01N 33/566* (2013.01); *A61K 39/35* (2013.01); *C07K 14/4703* (2013.01); *C07K 16/18* (2013.01); *G01N 33/564* (2013.01); *G01N 33/575* (2026.01); *A61K 38/00* (2013.01); *C07K 2319/00* (2013.01); *C07K 2319/30* (2013.01); *G01N 2500/00* (2013.01)

(58) Field of Classification Search
CPC .. G01N 33/566; G01N 33/564; G01N 33/574; G01N 2500/00; A61K 39/35; A61K 38/00; C07K 14/4703; C07K 16/18; C07K 2319/00; C07K 2319/30; A61P 35/00
See application file for complete search history.

(56) References Cited

U.S. PATENT DOCUMENTS

2006/0052320 A1* 3/2006 Li ...................... A61K 38/1709
514/44 R
2009/0226887 A1* 9/2009 Brisson ............. G01N 33/5432
435/7.1

FOREIGN PATENT DOCUMENTS

WO WO-2004055519 A2 * 7/2004 ......... G01N 33/6803
WO 2005027965 A1 3/2005
WO 2009/049892 A1 4/2009

OTHER PUBLICATIONS

Patel et al. (Biochemistry 44:2833-2844, 2005).*
Chao et al. Dendritic cells respond to nasopharygeal carcinoma cells through annexin A2-recognizing DC-SIGN. Oncotarge 6(1): 159-170, published Nov. 6, 2014.*
Gerke, Annexins: From Structure to Function, Physiology Review, 2002, pp. 331-371, v. 82 [NPL_GERKE].
Fatimathas, Annexins as disease modifiers, Histol Histopathol, 2010, pp. 527-532, v. 25 [NPL_FATIMATHAS].
Linke, The Tolerogenic Function of Annexins on Apoptotic Cells is Mediated by the Annexin Core Domain, The Journal of Immunology, 2015, pp. 5233-5242, v. 194 [NPL_LINKE].
Ling, Identification and Characterization of the Acidic pH Binding Sites for Growth Regulatory Ligands of Low Density Lipoprotein Receptor-related Protein-1, The Journal of Biological Chemistry, 2004, pp. 38736-38748, v. 279(37) [NPL_LING].
Krammer, PCT/EP2015/077066, WO2016113022A1, International Search Report and Written Opinion of the International Searching Authority (EPO), mailed Jan. 25, 2016 [WO2016113022A1_ISR_WO].
Ernst, Stefanie et al. "An Annexin 1 N-Terminal Peptide Activates Leukocytes by Triggering Different Members of the Formyl Peptide Receptor Family." The Journal of Immunology 172(12):7669-7676, Jun. 15, 2004.
Goulet, Francine et al. "Glycosylation of Annexin I and Annexin II." Biochemical and Biophysical Research Communications 188(2):554-558, Oct. 30, 1992.
Hayhoe, Richard P. G. et al. "Annexin 1 and its bioactive peptide inhibit neutrophil-endothelium interactions under flow: indication of distinct receptor involvement." Blood 107(5):2123-2130, Mar. 1, 2006.

(Continued)

*Primary Examiner* — Alana Harris Dent
(74) *Attorney, Agent, or Firm* — SALIWANCHIK, LLOYD & EISENSCHENK

(57) ABSTRACT

The present invention relates to a method for identifying a compound that modulates the interaction of an annexin core domain with a receptor selected from the group of C-type lectin receptors and LRP-1 in a cell, and uses thereof in autoimmune and/or cancer therapy.

22 Claims, 65 Drawing Sheets

Figure 1A:
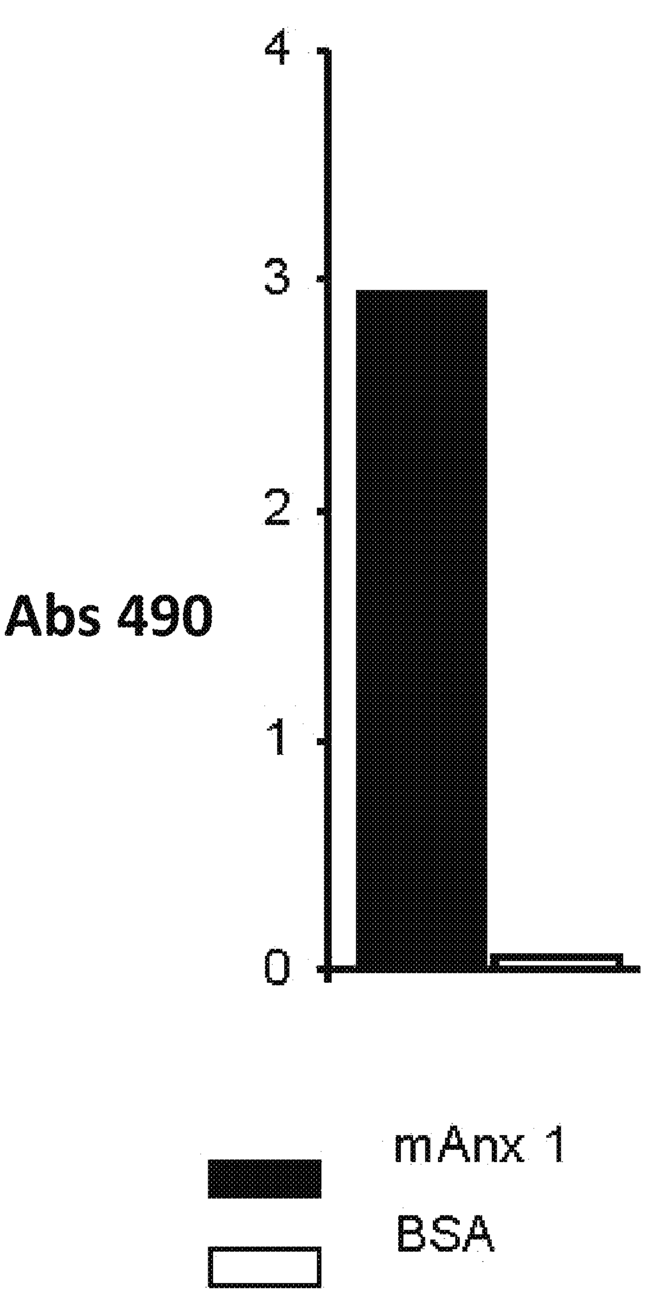

Specification includes a Sequence Listing.

(56) References Cited

OTHER PUBLICATIONS

Lim, Lina H. K. & Pervaiz, Shazib "Annexin 1: the new face of an old molecule." The FASEB Journal, 21(4):968-975, Apr. 2007.
Perretti, Mauro & Gavins, Felicity N. E. "Annexin 1: an Endogenous Anti-inflammatory Protein." News Physiol Sci, 18(2):60-64, (Year: 2003).
Pupjalis, Danute et al. "Annexin A1 released from apoptotic cells acts through formyl peptide receptors to dampen inflammatory monocyte activation via JAK/STAT/SOCS signalling." EMBO Molecular Medicine 3(2):102-114, (Year: 2011).
Scannell, Michael et al. "Annexin-1 and Peptide Derivatives Are Released by Apoptotic Cells and Stimulate Phagocytosis of Apoptotic Neutrophils by Macrophages." The Journal of Immunology, 178(7):4595-4605, Apr. 1, 2007.
Sugimoto, Michelle Amantea et al. "Annexin A1 and the Resolution of Inflammation: Modulation of Neutrophil Recruitment, Apoptosis, and Clearance." Journal of Immunology Research 2016(1):1-13, (Year: 2016).
Office action issued by the Canadian Patent Office dated Feb. 25, 2022 with respect to the Canadian priority application No. 2,973,409.

* cited by examiner

DC cocultured w/

OVA-annexin beads ( ◯) or

OVA-control beads ( ●)

and OVA-spec. T cells (○)

FIG. 12C mRNA expression normalized to GAPDH

| | NΦ | BMDC |
|---|---|---|
| FPR1 | 36.30 ± 0.52 | 0.36 ± 0.01 |
| FPR2 | 869.24 ± 30.90 | 12.35 ± 0.90 |
| FPR3 | 0.04 ± 0.01 | 0.03 ± 0.01 |

FIG. 19 hANXA1 → gi|47115305|emb|CAG28612.1|
hANXA5 → gi|49456639|emb|CAG46640.1|
hANXA13 → gi|49456633|emb|CAG46637.1| mANXA1 → gi|71059925|emb|CAJ18506.1|
mANXA5 → gi|13277612|gb|AAH03716.1|
mANXA13 → gi|13397933|emb|CAC34623.1|

MODULATORS OF THE FUNCTION OF THE CORE DOMAIN OF ANNEXINS, AND USES THEREOF IN AUTOIMMUNE AND/OR CANCER THERAPY

CROSS-REFERENCE TO RELATED APPLICATIONS

This U.S. non-provisional patent application is a U.S. national stage application, which was filed as U.S. Ser. No. 15/541,709 on Jul. 6, 2017 under 35 U.S.C. § 371 and claims priority to PCT Patent Application No. PCT/EP2015/077066, which was filed on Nov. 19, 2015, and to European Patent Application No. EP15151328.0, which was filed on Jan. 15, 2015. The contents of PCT Patent Application No. PCT/EP2015/077066 and European Patent Application No. EP15151328.0 are incorporated herein by reference in their entirety.

SEQUENCE LISTING

This application includes a Sequence Listing in electronic format as a txt file entitled "DKFZ-01-0203USWO_2017-07-06_D31370WOUS_US15541709_SEQLIST_ST25," which was created on Jul. 6, 2017 and which has a size of 17,953 bytes. The contents of txt file "DKFZ-01-0203USWO_2017-07-06_D31370WOUS_US15541709_SEQLIST_ST25" are incorporated by reference herein.

FIELD OF THE INVENTION

The present invention relates to a method for identifying a compound that modulates the interaction of an annexin core domain with a receptor selected from the group of C-type lectin receptors and LRP-1 in a cell, and uses thereof in autoimmune and/or cancer therapy.

BACKGROUND OF THE INVENTION

One crucial mechanism of peripheral tolerance induction is the uptake, processing and presentation of apoptotic cell (AC)-derived antigens by professional phagocytes (1). In the steady state, immature dendritic cells (DCs) continuously engulf ACs and present self-antigens from peripheral tissues in the draining lymph nodes (2, 3). Thus, DCs play a pivotal role in controlling the interface of innate and acquired immunity by providing soluble and intercellular signals, followed by recognition of pathogens. These functions of DCs are largely dependent on the expression of specialized surface receptors, pattern recognition receptors (PRRs), represented, most notably, by toll-like receptors (TLRs) and C-type lectins or lectin-like receptors (LLRs) (Figdor, C. G., Y. van Kooyk, and G. J. Adema. 2002. C-type lectin receptors on dendritic cells and Langerhans cells. Nat Rev Immunol 2:77-84. Pyz, E., A. S. Marshall, S. Gordon, and G. D. Brown. 2006. C-type lectin-like receptors on myeloid cells. Ann Med 38:242-251. Brown, G. D. 2006. Dectin-1: a signalling non-TLR pattern-recognition receptor. Nat Rev Immunol 6:33-43).

In the absence of inflammation or infection, the presentation of self-antigens to naïve T cells induces tolerance (4-6). Defects in AC uptake, AC processing or tolerization of phagocytes after AC uptake have been implicated in the development of autoimmune diseases and chronic inflammatory disorders (7-10). Whereas a plethora of eat-me signals and their uptake receptors on phagocytes are well characterized, little is known about molecules on ACs that mediate DC tolerization.

Annexins comprise a family of calcium- and phospholipid-binding proteins. Over 20 members have been found in all eukaryotic kingdoms as well as plants and animals with the exception of fungi. Annexins have molecular weights ranging between 30 and 40 kDa (only annexin VI is 66 kDa) and possess striking structural features. Annexins' amino-terminal domains are diverse in sequence and length (ranging from 11 to 196) on each annexin member. In contrast the carboxyterminal regions consisting of four (eight only for annexin VI) a-helical domains composed of about 70 amino acid residues are well conserved among annexins. The calcium- and phospholipid-binding sites are located in the carboxyterminal domains. The $Ca^{2+}$ binding similarities of all the annexins is due to their common primary structure, a unique N-terminal domain (the "tail") and the conserved C-terminal domain (the "core"). With the exception of annexin VI, the conserved C-terminal domain is always composed of 4 repeats (annexin VI having 8) of −70 amino acids containing an increased homology region called the "endonexin fold". In addition to the C terminal core the annexins contain a significantly more variable N terminal head. It is this domain which endows each annexin with unique functions in a diverse range of cellular processes including; endo- and exocytosis, cytoskeletal regulation and membrane conductance and organisation. Given their involvement in such a variety of processes it is not surprising that the annexins have also been implicated in a range of disease pathologies. Although there is no singular disease state directly attributed to a dysregulation in annexin function, several pathological conditions are suggested to be modified by the annexins. Fatimathas and Moss (in: Annexins as disease modifiers. Histol Histopathol. 2010 April; 25(4):527-32) discuss the growing evidence for the role of the annexins in the progression of cancer, diabetes and the autoimmune disorder anti-phospholipid syndrome.

Recently, the early exposure of the cytosolic protein annexin A1 (AnxA1) was identified by the present inventors as a tolerogenic signal on the surface of ACs (11).

In AnxA1, lipid binding is mediated by the C-terminal core domain highly conserved among all annexin family members (12, 13), and peptides corresponding to the AnxA1 N-terminus were shown to bind to members of the N-formyl peptide receptor (FPR) family, resulting in a reduction of neutrophil transmigration in several models of acute and chronic inflammation (15-18). Downstream signaling induced by binding of AnxA1 N-terminal peptides to FPR family members causes activation of ERK, but not of p38 or JNK (19, 20). Additional anti-inflammatory properties of AnxA1 have been attributed to the inhibition of cytosolic as well as of secretory phospholipase $A_2$ (c/s$PLA_2$) activity (21-23). Inhibition of s$PLA_2$ is mediated by the antiflammin-2 (AF-2) sequence, which also negatively regulates polymorphonuclear leukocyte (PMN) adhesion to activated endothelium by binding to human FPR2 (24).

The presence of multiple annexin family members in all higher eukaryotes suggests a fundamental role for annexins in cell biology. Mice deficient in individual annexin family members, however, have no severe phenotype, suggesting that several annexins have (partly) overlapping functions (12, 25). In fact, functional redundancy of annexins was proven in the context of membrane trafficking, inhibition of $PLA_2$ activity and blood coagulation (12).

US 2002-052358 describes a method of treating a subject with arthritis or an arthritic disease or preventing arthritis or arthritic disease in a subject, comprising administering to the subject a therapeutically effective amount of an agent that attenuates annexin function. Also provided are various methods of screening for agents.

WO 01/10199 describes a knockout transgenic mouse containing a nonfunctional allele of the tumor suppressing gene, annexin VII. This mouse is used as a screening model for potential therapeutic agents useful in the treatment of tumors resulting from an annexin tumor suppressor disease.

JP 2014-095643 describes screening of a compound effective in treatment of inflammatory disease, based on an inhibition of binding between annexin A2 and ADAM17.

WO 2014/126127 describes a method for screening an active ingredient for the treatment of severe enanthema, skin erythema, body surface erosion, blister and excoriation as formyl peptide receptor 1-induced necroptosis-related diseases. The active ingredient to be screened is said to be a substance capable of inhibiting necroptosis that is induced by the binding of formyl peptide receptor 1 to annexin A1.

WO 02/17857 discloses methods for inhibiting angiogenesis in endothelial cells and selectively inducing apoptosis in endothelial cells via compounds which binds annexin II are provided. These compounds and methods for using these compounds are regarded as useful in the treatment of diseases or disorders characterized by unwanted angiogenesis. Also provided are pharmaceutical compositions containing a compound which binds annexin II and a pharmaceutically acceptable vehicle and methods for identifying such compounds.

WO 2005/027965 discloses anti-annexin antibodies and their uses as well as uses of theirs ligands, the annexins. Such annexins and anti-annexin antibodies are useful for detecting apoptosis and for the production of pharmaceutical compositions for the diagnosis and/or treatment of cancer, autoimmune diseases, cardiovascular and/or vascular diseases.

US 2014/0322214 discloses compositions and methods for binding Dectin-1 on immune cells with anti-Dectin-1-specific antibodies or fragment thereof capable of activating the immune cells as well as methods for treating or preventing an influenza infection in a subject in need thereof comprising administering to the subject a therapeutically effective amount of a composition comprising an anti-dectin-1 antibody fused to an influenza antigen.

The thesis of Connie Hesse, CLEC7A/Dectin-1 attenuates the immune response against dying and dead cells, Friedrich-Alexander-University Erlangen-Nürnberg, 2011, discusses the role of C-type lectins CLEC4L/DC-SIGN, CLEC9A/DNGR1, and CLEC7A/dectin-1 in the recognition as well as the uptake of apoptotic and necrotic cells and/or their effects on the immunogenicity of dying and dead cells.

The low-density lipoprotein receptor-related protein-1 (LRP-1) is a membrane receptor displaying both scavenging and signaling functions. The wide variety of extracellular ligands and of cytoplasmic scaffolding and signaling proteins interacting with LRP-1 gives it a major role not only in physiological processes, such as embryogenesis and development, but also in critical pathological situations, including cancer and neurological disorders (Emonard H et al. Regulation of LRP-1 expression: make the point. Pathol Biol (Paris). 2014 April; 62(2):84-90. doi: 10.1016/j.patbio.2014.02.002. Epub 2014 Mar. 21). Cell surface annexin VI may function as an acidic pH binding site or receptor and may also function as a co-receptor with LRP-1 at neutral pH in the context of alpha 2-macroglobulin recognition (Ling T Y et al. Identification and characterization of the acidic pH binding sites for growth regulatory ligands of low density lipoprotein receptor-related protein-1. J Biol Chem. 2004 Sep. 10; 279(37):38736-48. Epub 2004 Jun. 28).

Finally, Weyd et al. (in: Weyd H, Abeler-Domer L, Linke B, Mahr A, Jahndel V, et al. (2013) Annexin A1 on the Surface of Early Apoptotic Cells Suppresses CD8+ T Cell Immunity. PLoS ONE 8(4): e62449. doi:10.1371/journal.pone.0062449) disclose that in mice, AnxA1 prevented the development of inflammatory DC and suppressed the cellular immune response against the model antigen ovalbumin (OVA) expressed in apoptotic cells. Furthermore, AnxA1 on apoptotic cells was found to compromise OVA-specific tumor vaccination and impaired rejection of an OVA-expressing tumor, and that this process may play an important role in prevention of autoimmune diseases and of the immune response against cancer.

Despite the above approaches, new targets for the development of new therapies based on immunosuppression that may prove beneficial for patients with cancer or autoimmune diseases and chronic inflammatory disorders are highly desired. It is therefore an object of the present invention, to provide these new targets and to employ these targets in the development of new and effective therapies. Other objects and aspects of the present invention will become apparent to the person of skill upon reading the following description of the invention.

According to a first aspect thereof, the object of the present invention is solved by providing a method for identifying a compound that modulates the interaction of an annexin core domain with a receptor selected from the group of C-type lectin receptors and LRP-1 in a cell, comprising the steps of a) contacting at least one of annexin, a receptor-binding core domain or fragment thereof of annexin, and/or a cell recombinantly expressing a receptor-binding core domain or fragment thereof of annexin with at least one compound that potentially modulates the interaction of said annexin core domain with said receptor in said cell, and b) identifying a modulation of said interaction of said annexin core domain with said receptor in the presence of said at least one compound, compared to the absence of said at least one compound.

It was surprisingly found by the present inventors that the suppressive activity of annexins is mediated through the conserved core domain, and all publications so far (see, for example, above) map the activity of AnxA1 in the N-terminal domain thereof, mediated by receptors of the formyl-peptide-receptor-family. Since the core domain is highly conserved between all vertebrate-annexina, all respective annexins, including the ones as studied in the context of the present invention, must have the same biological (suppressive) activity. In consequence, the annexin core domain provides a valuable tool for therapeutic approaches in order to treat or prevent cancer and/or autoimmune diseases. Thus, the inventors found it conceivable to target annexin in human disease without affecting vital functions.

In the context of the present invention, the term "annexin core domain" shall be understood as indicating/representing the minimal fragment of the polypeptide for annexin (or homologs thereof), which is necessary and sufficient to bind to a C-type lectin receptor and/or LRP-1 or functional fragment thereof. This ability (biological function) may be tested in a number of art known methods as described herein, and, e.g. in the examples, below. This ability may further be tested in a number of art known methods as described in the respective literature. For examples for core domains, see also FIG. 18, below. Also, the term shall particularly comprise the vertebrate, in particular mammalian (in particular human) annexin gene and/or protein and/or mRNA and/or the fragment (core domain) as described herein. The term also covers the annexin core domain in different preparations, such as in the cellular context, a cell recombinantly expressing said core domain, purified from the cell, and fractions, in particular biologically active factions, thereof.

In the context of the present invention, the terms "C-type lectin receptor", "Dectin-1", "DC-SIGN", and "LRP-1" shall be understood as indicating/representing the minimal fragment of the receptor(s), which is necessary and sufficient to bind to a core domain of the annexin as described and tested in the examples, and in, for example, Hesse as mentioned above for lectin-Fc fusion proteins. This ability may further be tested in a number of art known methods as described in the respective literature. Also, the term shall comprise the mammalian (in particular mouse) homolog of the human receptor gene and/or protein and/or mRNA and/or the fragment (binding part, fragment or domain) as described herein. The term also covers the receptor(s) and/or the minimal fragment of the receptor(s) in different preparations, such as in the cellular context, a cell (recombinantly) expressing said receptor(s) and/or the minimal fragment of the receptor(s), purified from the cell, and fractions thereof.

With Dectin-1 and DC-SIGN as members of the family of C-type lectin receptors and LRP-1, novel DC-surface receptors could be identified that with high affinity bind to the core domain of all annexins as studied. This is an indication that Dectin-1 and DC-SIGN are responsible for the annexin-mediated suppression of the immune response and the induction of peripheral tolerance, whereas the annexin-LRP-1-binding is required for the phagocytosis of apoptotic cells.

The effect of the annexins on DC via specific receptors is a novel molecular mechanism of immunological tolerance, resulting in a multitude of novel possibilities both for the therapy of cancers and tumors, as well as for autoimmune diseases, rejection, transplantation and allergies in mammals, such as mice and humans.

WO 2009/049892 describes a first polypeptide (A) comprising a recruiting polypeptide (a) comprising at least an annexin core domain or a functional variant thereof, a bait polypeptide (b) and a luminophore. The composition according to the invention can be used to measure protein-protein interactions within and/or between entire multiprotein complexes. Described is the use of the method according to the invention for the identification of a test compound in a library of test compounds which modulates a medically relevant protein-protein interaction, without that any concrete disease context is disclosed. WO 2009/049892 is silent about any interaction(s) of annexin with Dectin-1, DC-SIGN and/or LRP-1, and also non-enabling for the screening of therapeutically relevant compounds and/or compositions.

WO 2005/027965 describes that annexin I and other annexins are related to specific receptors, which could be stimulated or blocked by either binding of one of the annexins or fragments thereof or an antibody against this receptor. Thus, annexins and/or functional fragments thereof and/or fusion proteins comprising an annexin or functional fragments thereof are discussed to be of use to modulate the immune system. WO 2005/027965 is silent about any interaction(s) of the annexin core domain and the relevance thereof with Dectin-1, DC-SIGN, and/or LRP-1, and thus is also non-enabling for the screening of therapeutically relevant compounds and/or compositions.

In the context of the present invention, the inventors discovered two novel tolerogenic signals on the surface of ACs, annexin A5 (AnxA5) and annexin A13 (AnxA13) promoting the development of DCs with a tolerogenic phenotype, i.e., DCs with an impaired upregulation of co-stimulatory molecules and with low pro-inflammatory cytokine secretion upon TLR stimulation. Importantly, these effects were mediated by the annexin core domain and were independent of N-terminal peptides of AnxA1 or the AF-2 sequence. In line, AnxA1, AnxA5 and AnxA13 inhibit the induction of antigen-specific $CD8^+$ T cell responses in vivo. Based on these results the inventors found that several annexins contribute to AC-induced immunosuppression in a functionally redundant manner and, thus, contribute to peripheral tolerance induction.

Exposure of bone marrow-derived dendritic cells (BMDCs) to AnxA5 or AnxA13 in vitro resulted in the inhibition of both the pro-inflammatory cytokine secretion and the upregulation of co-stimulatory molecules upon TLR-stimulation. In vivo, co-injection of apoptotic OVA-expressing and Anx-expressing cells prevented induction of antigen-specific $CD8^+$ T cells. These results suggest that several annexins contribute to AC-induced immunosuppression of DC activation. Manipulating Anx-mediated immunosuppression may therefore prove beneficial for patients with cancer or autoimmune diseases and chronic inflammatory disorders.

N-terminal peptides and the AF-2 sequence in the core domain have been implicated in mediating anti-inflammatory effects of AnxA1 (15, 21, 62, 63). However, several points make it unlikely that recognition by FPR family members contributes to the tolerogenic effect of annexins on BMDCs. First, the annexin core domain, highly conserved among annexin family members, is sufficient to inhibit TLR-induced cytokine secretion of BMDCs (FIG. 12). Second, mutation of the AF-2 sequence, the only other peptide sequence binding to FPR family members apart from the AnxA1 N-terminus, and ablation of the N-terminal domain of AnxA1 do not abrogate AnxA1-induced suppression of TLR-induced DC activation (FIG. 12) (24). Third, AnxA5 and AnxA13, which have not been shown to bind to FPR family members so far, possess suppressive activity comparable to AnxA1 (FIG. 14). Fourth, pan-specific antagonists of FPR family members do not abrogate the suppressive effect elicited by annexins. Finally, phosphorylation of ERK, induced upon binding of N-terminal peptides of AnxA1 to FPR family members, could not be detected in BMDCs upon treatment with AnxA1, AnxA5 or AnxA13. The lower levels of FPR family members expressed on DCs and/or different signaling thresholds of DCs compared to neutrophils may explain differential effects seen for the individual domains of annexins depending on the cell type or biological setting. The data presented here support the existence of different, hitherto unknown receptors involved in recognition of annexins on DCs, which were identified as belonging to the group of C-type lectin-1 and LRP-1-receptors.

As mentioned above, the annexin core domain that can be used in the method according to the present invention can be derived from any of the known annexins or functional fragments (i.e. able to bind to the receptors as described herein) thereof, and is preferably selected from the group of the human or murine annexin 1, 5, and 13 core domain, preferably according a sequence according to SEQ ID NO: 1, 2, 3, 6, 7, or 8, or functional fragments thereof, more preferably according to the boxed sequences as shown in FIG. 19. Similarly, the minimal fragments of the receptor(s) of the C-type lectins (e.g. Dectin-1 or DC-SIGN) or LRP-1, which are necessary and sufficient to bind to a core domain of the annexin(s) as described above can be preferably used in the method according to the present invention.

Preferred is a method according to the present invention, wherein said modulation is selected from a decrease or an increase of (a) an expression of said annexin and/or (b) of binding to said receptor(s) and/or (c) the biological activity of annexin, such as the annexin-mediated immunosuppression or phagocytosis of apoptotic cells.

Preferably, said identifying comprises a method selected from rtPCR, immunoprecipitation and measuring the induction or reduction of the translocation of annexin to the outer cell membrane and/or apoptosis in said cell. Respective assays are known to the person of skill, and described below.

More preferred is a method according to the present invention, wherein said compound is selected from the group consisting of a peptide library, a combinatory library, a cell extract, in particular a plant cell extract, a “small molecular drug”, an antisense oligonucleotide, an siRNA, an mRNA, a peptide binding to a receptor, a soluble fragment of said receptor, and a blocking or activating antibody or fragment thereof specifically interfering with the binding of the annexin core domain to said receptor(s), in particular anti-Dectin-1, anti-DC-SIGN, and/or anti-LRP-1 antibodies or functional fragments thereof.

According to the invention, a cell can be selected from the group of dendritic cells, macrophages, cancer cells, apoptotic cells, and recombinant host cells, such as dendritic cells, macrophages, cancer cells, apoptotic cells, S2 cells, or Mono Mac cells expressing said annexin core domain or fragment thereof, wherein said recombinant host cells optionally express or co-express the receptor(s) or fragment(s) thereof.

According to the invention, said cell can thus preferably be selected from the group of cancer cells and cell lines, and recombinant host cells expressing annexin or the receptor binding fragment thereof, wherein said recombinant host cells optionally express Dectin-1, DC-SIGN, LRP-1, yeast cells, and recombinant bacterial cells.

The method according to the present invention as described herein is thus suitable for the identification of compounds that can interact with the binding of the annexin core domain to a receptor as described, and/or the activities of annexin, and thus to identify, for example, inhibitors, activators, competitors or modulators of the annexin function, in particular, inhibitors, activators, competitors or modulators of the binding of the annexin core domain Preferred are compounds that inhibit the binding of the annexin core domain to the receptors. Another aspect is directed at compounds that modulate the expression of annexin in a cell/in cells.

Another aspect is directed at a method according to the present invention, further comprising testing said compound(s) as identified for its activity to sensitise tumour cells to apoptosis and/or to induce tolerance. Since apoptosis occurs via a complex signaling cascade that is tightly regulated at multiple points, there are many opportunities to evaluate the activity of the proteins involved. A large number of apoptosis assays are devised to detect and count apoptotic cells. Apoptosis assays, based on methodology, can be classified into six major groups and include assays detecting cytomorphological alterations; DNA fragmentation; detection of caspases, cleaved substrates, regulators and inhibitors; membrane alterations; detection of apoptosis in whole mounts; and mitochondrial assays. Respective assays are known to the person of skill, ad can be taken from the respective literature.

The term “contacting” in the present invention means any interaction between the potentially binding substance(s) with the annexin core domain, whereby any of the two components can be independently of each other in a liquid phase, for example in solution, or in suspension or can be bound to a solid phase, for example, in the form of an essentially planar surface or in the form of particles, pearls or the like. In a preferred embodiment a multitude of different potentially binding substances are immobilized on a solid surface like, for example, on a compound library chip and the annexin core domain (or a functional part thereof) is subsequently contacted with such a chip.

The potentially binding substance, the binding of which to annexin is to be measured, can be any chemical substance or any mixture thereof, as described above. For example, it can be a substance of a peptide library, a combinatory library, a cell extract, in particular a plant cell extract, a “small molecular drug”, an antisense oligonucleotide, an siRNA, an mRNA, a peptide binding to a receptor, a soluble fragment of said receptor, and a blocking or activating antibody or fragment thereof specifically interfering with the binding of the annexin core domain to said receptor(s), in particular anti-Dectin-1, anti-DC-SIGN, and/or anti-LRP-1 antibodies or functional fragments thereof.

Measuring of binding of the compound to the annexin core domain can be carried out either by measuring a marker that can be attached either to the protein or to the potentially interacting compound. Suitable markers are known to someone of skill in the art and comprise, for example, fluorescence or radioactive markers. The binding of the two components can, however, also be measured by the change of an electrochemical parameter of the binding compound or of the protein, e.g. a change of the redox properties of the annexin core domain or the binding compound, upon binding. Suitable methods of detecting such changes comprise, for example, potentiometric methods. Further methods for detecting and/or measuring the binding of the two components to each other are known in the art and can without limitation also be used to measure the binding of the potential interacting compound to the annexin core domain or fragments. The effect of the binding of the compound or the activity of the annexin core domain can also be measured indirectly, for example, by assaying the binding activity of the core domain to the receptors as described herein after binding.

As a further step after measuring the binding of a potentially interacting compound and after having measured at least two different potentially interacting compounds at least one compound can be selected, for example, on grounds of the measured binding activity or on grounds of the detected increase or decrease of annexin core domain receptor (binding) activity and/or core domain expression.

The thus selected binding compound can then in a preferred embodiment be modified in a further step. Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or iso-pentyl groups, lower alkenyl groups, preferably having two to five carbon atoms, lower alkynyl groups, preferably having two to five carbon atoms or through the introduction of, for example, a group selected from the group consisting of $NH_2$, $NO_2$, OH, SH, NH, CN, aryl, heteroaryl, COH or COOH group.

The thus modified binding substances are than individually tested with a method of the present invention, i.e. they are contacted with the annexin core domain and subsequently binding of the modified compounds to the core domain polypeptide is measured. In this step, both the binding per se can be measured and/or the effect of the function of the core domain like, e.g. the binding to the receptors as described and/or the enzymatic activity of the polypeptide can be measured. If needed, the steps of selecting the binding compound, modifying the binding compound, contacting the binding compound with an annexin core domain polypeptide and measuring the binding of the modified compounds to the protein can be repeated a third or any given number of times as required. The above described method is also termed "directed evolution" since it involves a multitude of steps including modification and selection, whereby binding compounds are selected in an "evolutionary" process optimizing its capabilities with respect to a particular property, e.g. its binding activity, its ability to activate or modulate the activity of the annexin core domain polypeptide towards the receptors as described herein.

According to another aspect thereof, the object of the present invention is solved by providing a screening tool for an agent for treating or preventing autoimmune diseases, chronic inflammatory diseases or allergies or cancer, in particular a screening tool for screening for a compound that modulates the interaction of an annexin core domain with a receptor selected from the group of C-type lectin receptors, preferably Dectin-1 or DC-SIGN, and LRP-1 in a cell, comprising an isolated cell expressing a receptor-binding core domain or fragment thereof of annexin, and wherein said cell optionally expresses or co-expresses the receptor(s) or fragment(s) thereof.

The cell can be a prokaryotic or eukaryotic cell, and the expression constructs can be present extrachromosomally or integrated into the chromosome. The polypeptides can be expressed in the form of a fusion protein, for example together with an enzymatically active moiety as reporter-construct, in order to be able to detect the expression product. Preferred host cells are derived from cells selected from the group of dendritic cells, macrophages, cancer cells, apoptotic cells, and recombinant host cells, such as dendritic cells, macrophages, cancer cells, apoptotic cells, S2 cells, or Mono Mac cells expressing said annexin core domain or fragment thereof, wherein said recombinant host cells optionally express or co-express the receptor(s) or fragment(s) thereof. Thus, preferred is a screening tool according to the present invention, comprising such a cell.

According to yet another aspect thereof, the object of the present invention is solved by providing a screening tool for an agent for treating or preventing for treating or preventing autoimmune diseases, chronic inflammatory diseases or allergies or cancer, in particular a screening tool for screening for a compound that modulates the expression, the biological activity and/or the interaction of the annexin core fragment with a receptor as described herein, wherein said cell as above is part of a non-human transgenic mammal, which preferably overexpresses the annexin core domain and/or a receptor as described above, optionally as a genetic reporter-construct. Preferred is a transgenic mouse, rat, pig, goat or sheep. Methods to produce these non-human transgenic mammals (over)expressing the annexin core domain and/or a receptor as described above and/or carrying an annexin core domain and/or a receptor as described above genetic reporter-construct are known to the person of skill in the art. Preferred are also transgenic non-human mammals wherein the gene that is homologous to the annexin core domain and/or a receptor as described above is exchanged by a gene having a modified function (e.g. knock-out or knock-in animal).

Similar to the strategies for identifying compounds that interact with the annexin core domain and the binding thereof to the receptors as described above, and/or the biological activity of the annexin core domain, e.g. the binding thereof to the receptors as described above, compounds can be identified that modulate the expression of annexin and/or the annexin core domain in a cell. In preferred strategies, the expression can be monitored using a genetic reporter-construct (in order to analyse the translation efficiency and/or stability of the polypeptide), for an example a fusion protein comprising a detectable fusion member (such as an enzymatic or fluorophoric group, or GFP as described herein), or the amount of mRNA as present in a cell can be measured, for example, by Northern blot. The expression can also be analyzed and monitored by using chip-analysis or rtPCR. Preferred compounds that modulate the expression of annexin and/or the annexin core domain in a cell are selected from specific antisense oligonucleotides, siRNAs, mRNAs or other preferably mutated nucleic acids encoding the annexin core domain. Another preferred embodiment is the transfer of said genetic elements using gene therapy. Furthermore, encompassed are viral constructs for the introduction of said genetic elements into said cells. Alternatively, also the "naked" nucleic acid can be introduced into the cell(s), e.g. by using particle-mediated technologies. Respective methods are well described in the literature and known to the person of skill.

Further preferred is the screening tool according to the present invention as described herein, wherein said annexin and/or said receptor(s) and/or the fragments thereof are labeled. Labels and methods for labeling are known to the person of skill, and can be enzymatic labels, dyes, fluorophores, and/or radioactive labels.

According to yet another aspect thereof, the present invention relates to the use of the tools according to the present invention as described herein for screening for a compound that modulates the expression, the biological activity and/or the interaction of the annexin core fragment with a receptor as described herein.

Another aspect of the present invention relates to a method for manufacturing a pharmaceutical composition for treating or preventing autoimmune diseases, chronic inflammatory diseases, allergies or cancer, comprising the steps of performing a method according to the present invention, and formulating said compound as identified into a pharmaceutical composition.

In a further embodiment of the method of the present invention, the interacting compound identified as outlined above, which may or may not have gone through additional rounds of modification and selection, is admixed with suitable auxiliary substances and/or additives. Such substances comprise pharmacological acceptable substances, which increase the stability, solubility, biocompatibility, or biological half-life of the interacting compound or comprise substances or materials, which have to be included for certain routs of application like, for example, intravenous solution, sprays, band-aids or pills.

Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

Administration of an agent, e.g., a compound can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, coated microparticles, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhaler, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

Yet another aspect of the present invention is directed at a pharmaceutical composition for treating or preventing autoimmune diseases, chronic inflammatory diseases, allergies or cancer, obtainable by a method according to the method as above.

In certain embodiments, the compound (activator or inhibitor) is administered to the subject by administering a recombinant nucleic acid, such as, for example, an anti-annexin or anti-annexin core domain RNA, for example an siRNA. Preferably, the recombinant nucleic acid is a gene therapy vector.

Another aspect of the present invention relates to a method or use as described herein, wherein the pharmaceutical composition further comprises additional pharmaceutically active ingredients for treating or preventing autoimmune diseases, chronic inflammatory diseases, allergies or cancer, i.e. chemotherapeutics.

Another aspect of the present invention relates to an isolated annexin core domain; a complex or fusion of an annexin core domain with at least one antigen or allergenic compound; an activating antibody, optionally coupled to at least one antigen or allergenic compound; or a pharmaceutical composition obtained by the method according to the present invention for use in the prevention and/or therapy of autoimmune diseases, chronic inflammatory diseases or allergies as described herein (see, e.g., below). Preferred is the complex or fusion for use according to the present invention, wherein said annexin or fragment thereof, complex or fusion is soluble or bound to a carrier, such as micro- or nanoparticles, e.g. of poly(D,L-lactide-co-glycolide) (PLGA) and PLGA-based polymers, hydroxyapatite particles, biocompatible nanoparticles consisting of biopolymers such as protein (silk, collagen, gelatin, β-casein, zein and albumin), protein-mimicked polypeptides and polysaccharides (chitosan, alginate, pullulan, starch and heparin), a liposome or latex bead.

Another aspect of the present invention relates to an inhibitor of (a) the expression of the annexin core domain and/or (b) of the binding of said core domain to a receptor selected from the group of C-type lectin receptors and LRP-1 and/or (c) of the biological activity of annexin or a pharmaceutical composition comprising said inhibitor for use in the therapy of cancer as described herein (see, e.g., below). Preferred is the inhibitor or pharmaceutical composition for use according to the present invention, wherein said inhibitor is selected from an antisense oligonucleotide, a soluble fragment of said receptor(s), and a blocking antibody or fragment thereof specifically interfering with the binding of said annexin core domain to said receptor(s), in particular anti-dectin-1, anti-DC-SIGN or anti-LRP-1 antibodies.

Another aspect of the present invention then relates to a monoclonal antibody or a functional fragment thereof (such as, for example, an scFv or Fab fragment) that specifically recognizes and interacts with the binding of the annexin core domain to a receptor as described herein. Preferably, said monoclonal antibody or a functional fragment thereof interferes (such as inhibits or activates) the binding of the annexin core domain to a receptor as described herein. The antibodies or fragments thereof can also be labeled (see above), and/or carry a therapeutic group attached to them, such as, for example, for antibody-directed enzyme prodrug therapy (ADEPT) or radioimmunotherapy (RIT).

Another aspect of the present invention then relates to a method for treating or preventing autoimmune diseases, chronic inflammatory diseases or allergies in a patient, comprising administering to said patient an effective amount of an isolated annexin core domain; a complex or fusion of an annexin core domain with at least one antigen or allergenic compound; an activating antibody, optionally coupled to at least one antigen or allergenic compound; or a pharmaceutical composition obtained by the method according to the present invention.

In general, the attending physician will base a treatment on the compound as identified, and optionally also on other individual patient data (clinical data, family history, DNA, etc.), and a treatment can also be performed based on the combination of these factors. This method of the present invention for example involves integrating individual diagnostic immunological data with patient clinical information and general healthcare statistics to enable, for example, the application of personalized medicine to the patient. Significant information about drug effectiveness, drug interactions, and other patient status conditions can be used, too.

Preferred is a therapeutic method according to the present invention, wherein said mammal to be treated is a mouse, rat or human.

Preferably, an activating active agent is administered in form of a pharmaceutical composition comprising an activating agent as described above, such as an antibody, nucleotide or an activating binding compound for the annexin core domain/receptor binding. Preferably, said patient is a human being. Treating is meant to include, e.g., preventing, treating, reducing the symptoms of, or curing the disease or condition, i.e. immunological diseases.

Another aspect of the present invention then relates to a method for treating or preventing cancer in a patient, comprising administering to said patient an effective amount of an inhibitor of the expression of the annexin core domain and/or of the binding of said core domain to a receptor selected from the group of C-type lectin receptors, preferably Dectin-1, DC-SIGN and LRP-1 and/or of the biological activity of annexin or a pharmaceutical composition comprising said inhibitor.

In general, the attending physician will base a treatment on the compound as identified, and optionally also on other individual patient data (clinical data, family history, DNA, etc.), and a treatment can also be performed based on the combination of these factors. This method of the present invention for example involves integrating individual diagnostic cancer data with patient clinical information and general healthcare statistics to enable, for example, the application of personalized medicine to the patient. Significant information about drug effectiveness, drug interactions, and other patient status conditions can be used, too.

Preferred is a therapeutic method according to the present invention, wherein said mammal to be treated is a mouse, rat or human.

More preferably, the cancer to be treated is a solid tumor, such as, for example, selected from breast, bone, ovarian, liver, kidney, and lung cancer.

Preferably, an inhibiting active agent is administered in form of a pharmaceutical composition, such as an antibody, nucleotide or an inactivating binding compound for the annexing core domain/receptor binding. Preferably, said patient is a human being. Treating is meant to include, e.g., preventing, treating, reducing the symptoms of, or curing the disease or condition, i.e. cancer.

An "effective amount" is an amount of the compound(s) or the pharmaceutical composition as described herein that reduces or increases the expression and/or abundance of the annexin core domain in/on a cell, or inhibits and/or reduces or activates and/or increases the binding of the annexin core domain to the receptors as described herein. The amount alleviates symptoms as found for the disease and/or condition.

The invention also includes a method for treating a subject at risk for autoimmune diseases, chronic inflammatory diseases, allergies or cancer, wherein a therapeutically effective amount of a modulator as above is provided. Being at risk for the disease can result from, e.g., a family history of the disease, a genotype which predisposes to the disease, or phenotypic symptoms which predispose to the disease.

The mammalian patient can be a rat, mouse, goat, rabbit, sheep, horse, monkey or human, preferred is a mouse, rat or human.

Yet another preferred aspect of the present invention then relates to a kit, comprising materials for identifying and screening compounds according to a method according to the present invention as described herein, in one or separate containers, preferably comprising a screening tool according to the present invention. Optionally, the kit comprises instructions for performing a method according to the present invention as described herein.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The container may be formed from a variety of materials such as glass or plastic. Preferably the kit and/or container contain/s instructions on or associated with the container that indicates directions for reconstitution and/or use.

Preferred is a kit according to the present invention, wherein said kit comprises materials for a method selected from the group of Western blots and/or Enzyme-Linked Immunosorbent Assay (ELISA). For example, the label may indicate that the lyophilized formulation is to be reconstituted to certain antibody concentrations as suitable for the above methods, such as ELISA.

Further preferred is the use according to the present invention, wherein said kit comprises monoclonal antibodies or fragments thereof specific for the annexin core domain and/or functional parts and variants thereof as described herein.

Uptake and processing of self-antigens derived from ACs by DCs in the steady state, and subsequent presentation of self-peptides on MHC I and MHC II by tolerogenic DCs is an important mechanism to induce $CD4^+$ and $CD8^+$ T cell tolerance in the periphery (36, 37). Immunosuppression of phagocytes by ACs is mediated by tolerogenic signals on the surface of ACs including growth arrest-specific gene 6 (Gash), inactivated complement component 3b (iC3b), thrombospondin 1 (TSP1) and AnxA1 (10, 11, 38-40). In lymphoid organs, the subsequent interaction of tolerogenic DCs and auto-reactive T cells induces anergy, deletion or may trigger conversion of naïve $CD4^+$ T cells into $T_{reg}$ (41-46). As the knowledge of tolerogenic signals on the surface of ACs is limited and functional redundancy has been reported for different properties of annexins, the experiments underlying the present invention aimed at investigating whether annexins act as redundant tolerogenic signals on ACs.

Upon induction of apoptosis AnxA1 translocates to the surface of ACs and is recognized by phagocytosing DCs (11). Using a leukemia cell line and stably transfected apoptotic S2 cells the inventors could show that translocation upon induction of apoptosis is a common feature of AnxA1, AnxA5 and AnxA13 (FIG. 13). Translocation of AnxA5 to the surface of rat cardiomyocytes upon treatment with staurosporine or hydrogen peroxide has already been reported (47). Externalization of AnxA5 also takes place under pathophysiological conditions like acute myocardial infarction or glomerulonephritis (48, 49). In both cases passive release from necrotic cells cannot be ruled out. However, the experiments show that annexins are externalized at an early stage of apoptosis preceding the loss of membrane integrity (FIG. 13).

AnxA5 and AnxA13 induce the development of a tolerogenic DC phenotype as was previously shown for AnxA1 (11). Soluble and membrane-bound AnxA5 and AnxA13 inhibit the TLR-induced secretion of pro-inflammatory cytokines, i.e., IL-12, IL-6 and TNF-α, while the secretion of IL-10 is not affected (FIG. 14). TLR-induced upregulation of the co-stimulatory molecules CD40, CD80 and CD86 was inhibited by annexin pretreatment, whereas surface levels of MHC class I and II molecules and co-inhibitory molecules were not altered (FIG. 15). Thus, the phenotype of DCs obtained after annexin incubation resembles the one of DCs after uptake of ACs or upon incubation with AC-derived tolerogenic signals (10, 38, 39, 50-52). Expression of MHC molecules on DCs is a prerequisite for efficient presentation of self-peptides and, thus, required for deletion or tolerization of auto-reactive T cells in the draining lymph nodes (2). In addition, low expression of co-stimulatory molecules, especially of CD40, has been described as a decisive feature of tolerogenic DCs (53, 54). Inhibition of TLR-induced upregulation of co-stimulatory molecules has been observed after incubation of BMDCs with the tolerogenic signals Gas6 or iC3b or upon ligation of receptors that recognize tolerogenic signals, including Mer tyrosine kinase (MerTK), complement receptor 3 (CR3) or CD36 (10, 38, 39, 51). Importantly, deletion and functional inactivation of auto-reactive $CD8^+$ T cells does not only require the absence of CD40L-induced signaling, but also expression of PD-1 ligands, i.e., PD-L1 and PD-L2, both of which were not affected by annexin pretreatment of BMDCs (46).

Similar to AC uptake or ligation of MerTK, CD36 or CR3, pre-incubation of BMDCs with annexins results in inhibition of TLR-induced secretion of pro-inflammatory cytokines including TNF-α, IL-6 and IL-12 (FIG. 14 (10, 38, 39, 50)). Low secretion of the $T_H1$-promoting cytokines TNF-α and IL-12 as well as of the $T_H17$-promoting cytokine IL-6 implies that $T_H1$ and $T_H17$ priming of naïve $CD4^+$ T cells by annexin-treated BMDCs is unlikely.

Figure 4:
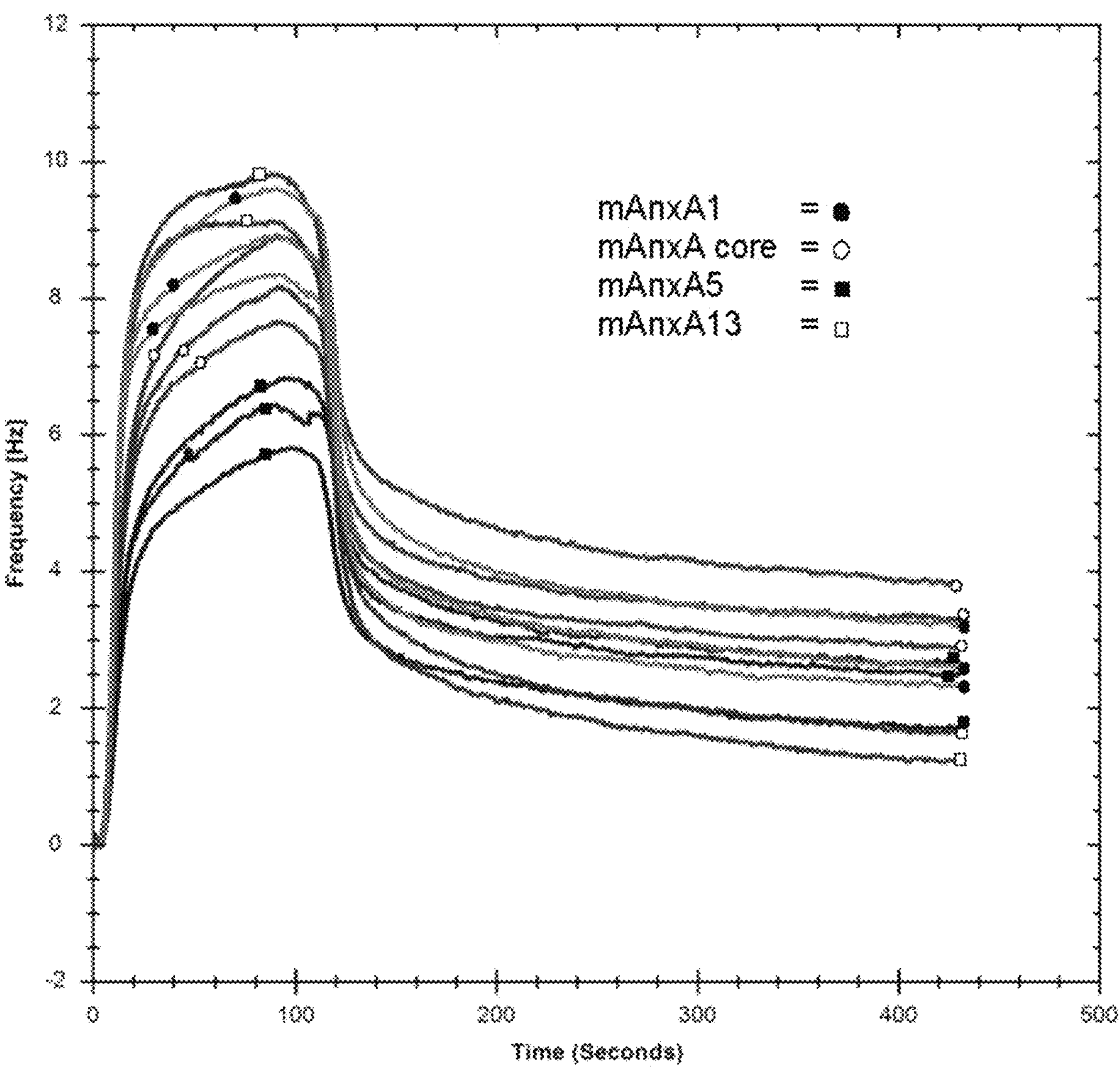
Figure 5A:
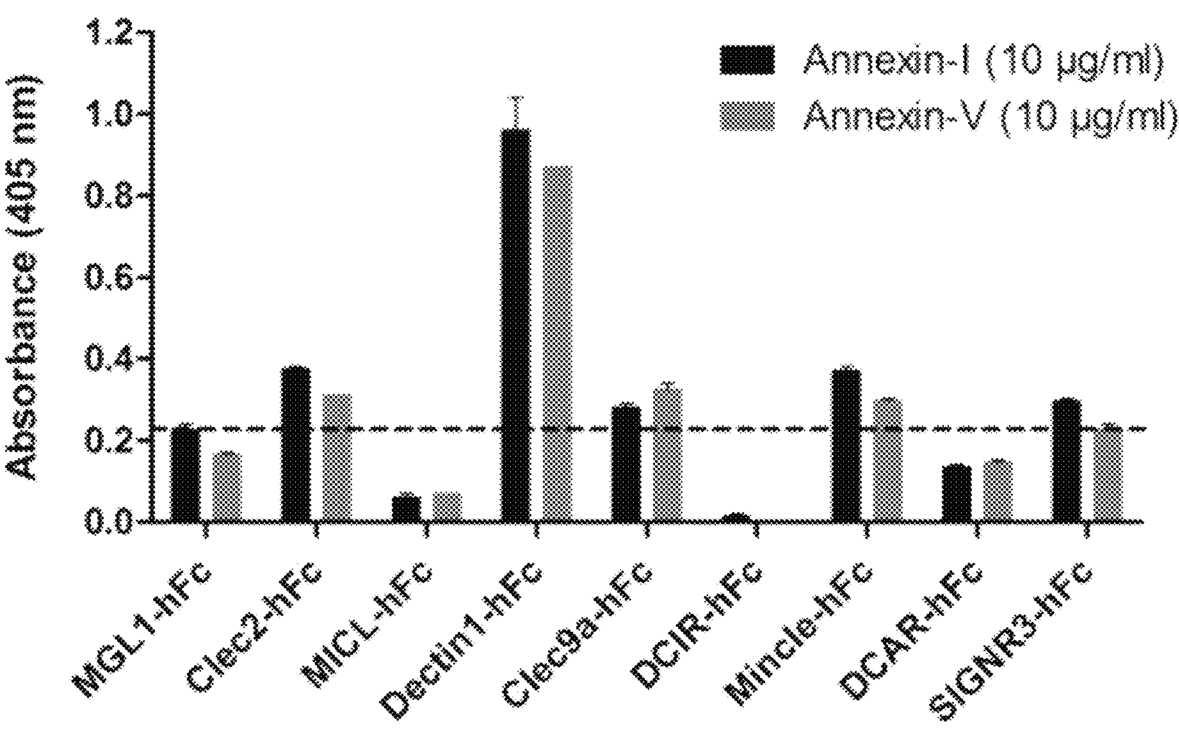
Figure 5B:
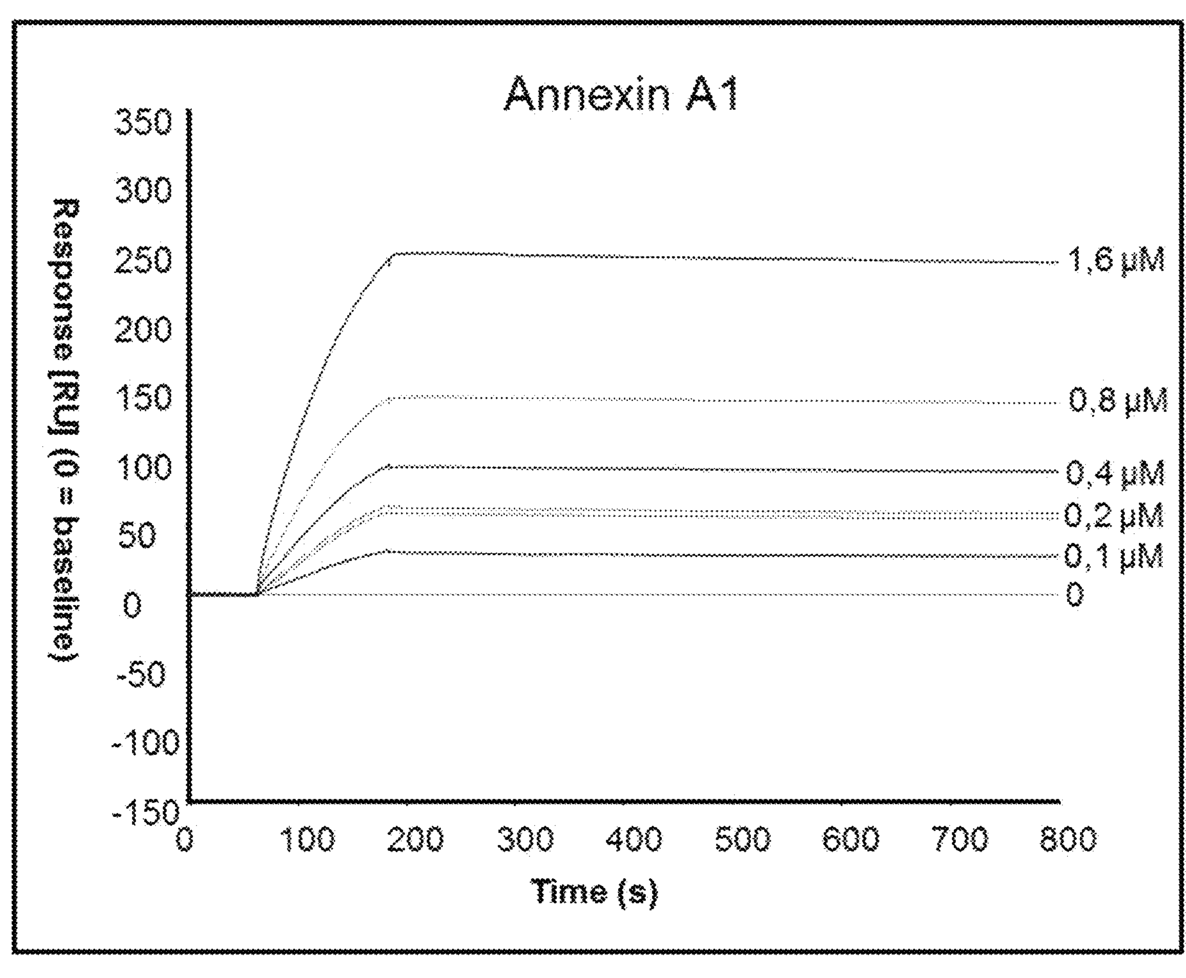
Figure 5C:
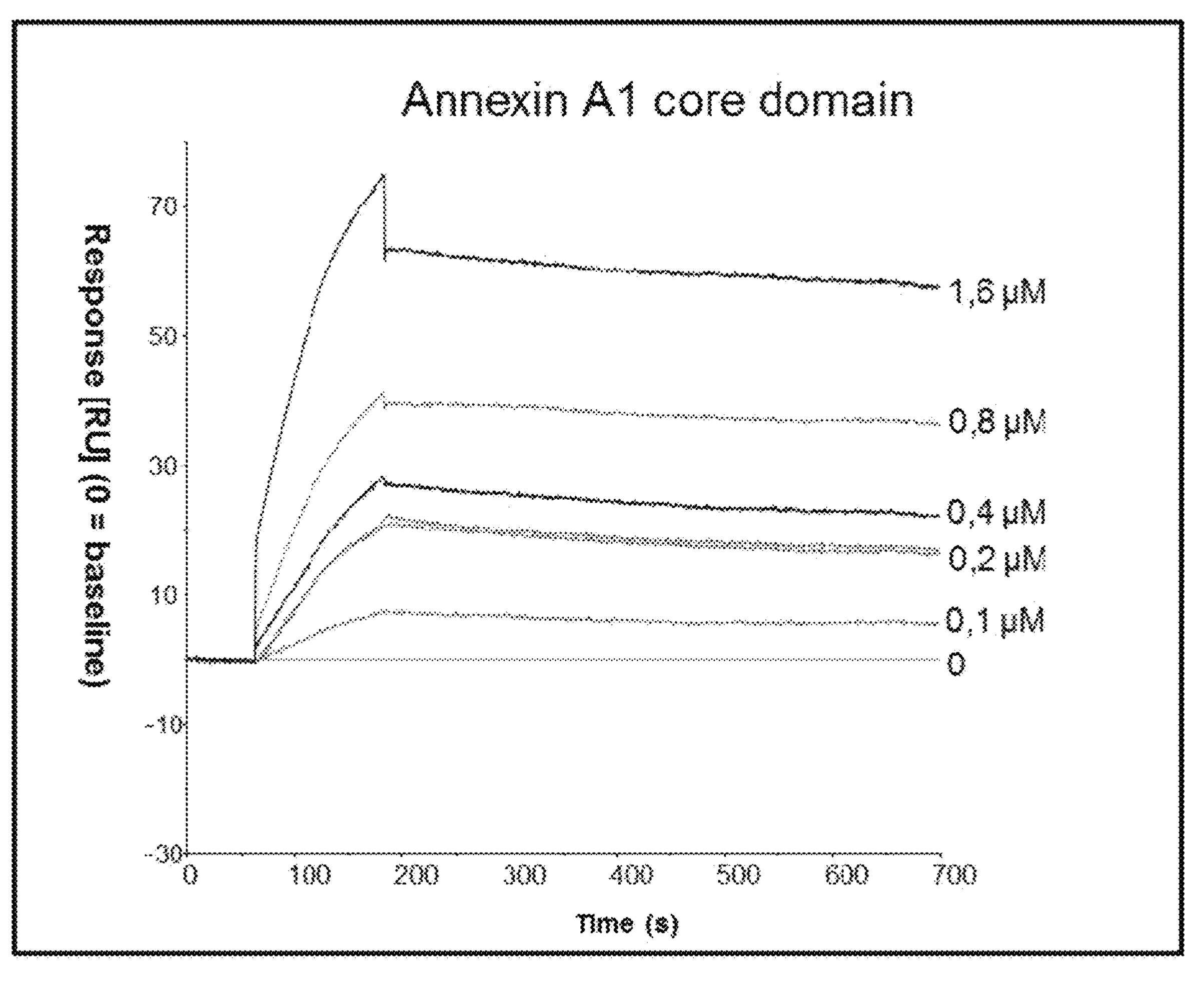
Figure 5D:
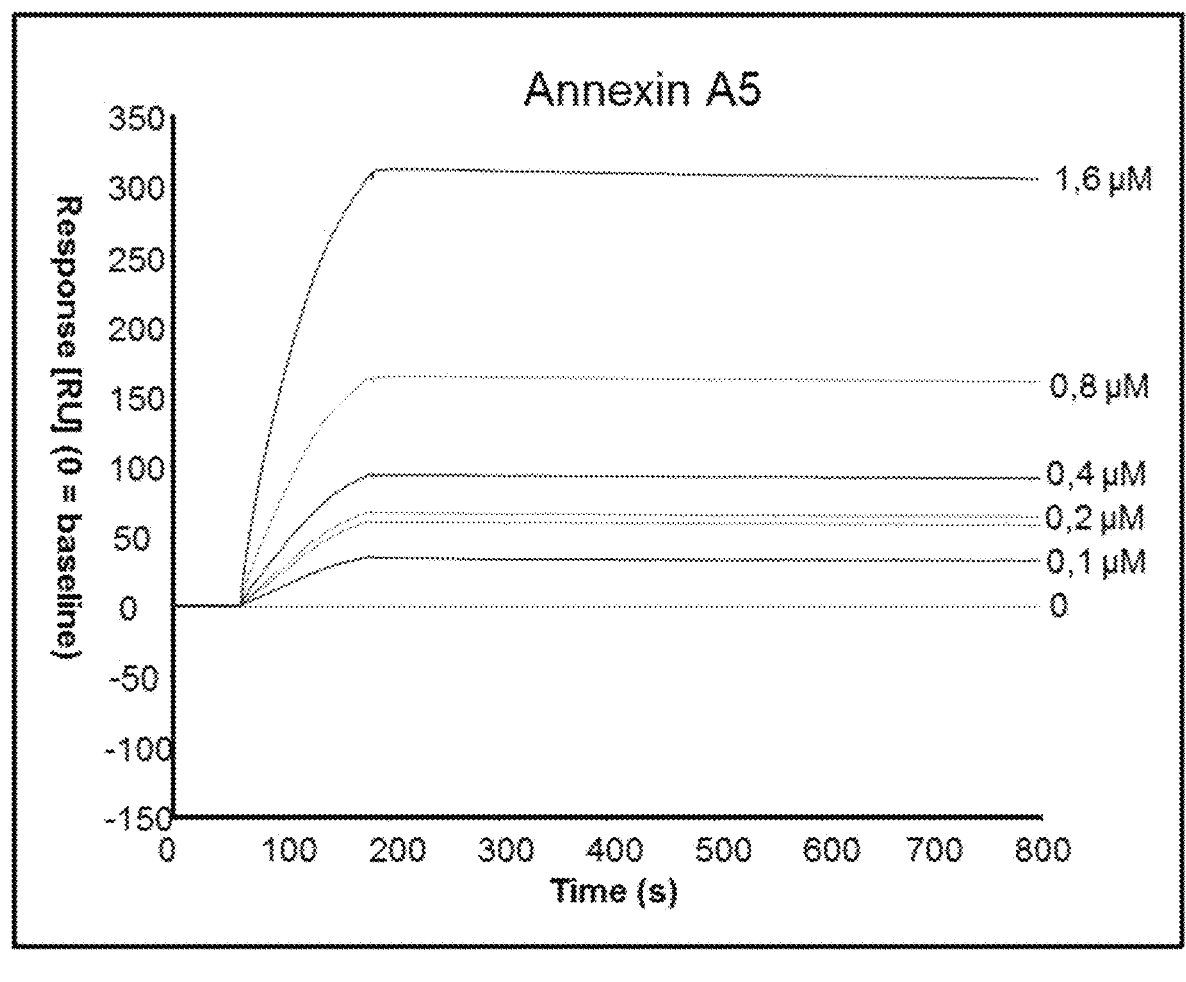
Figure 5E:
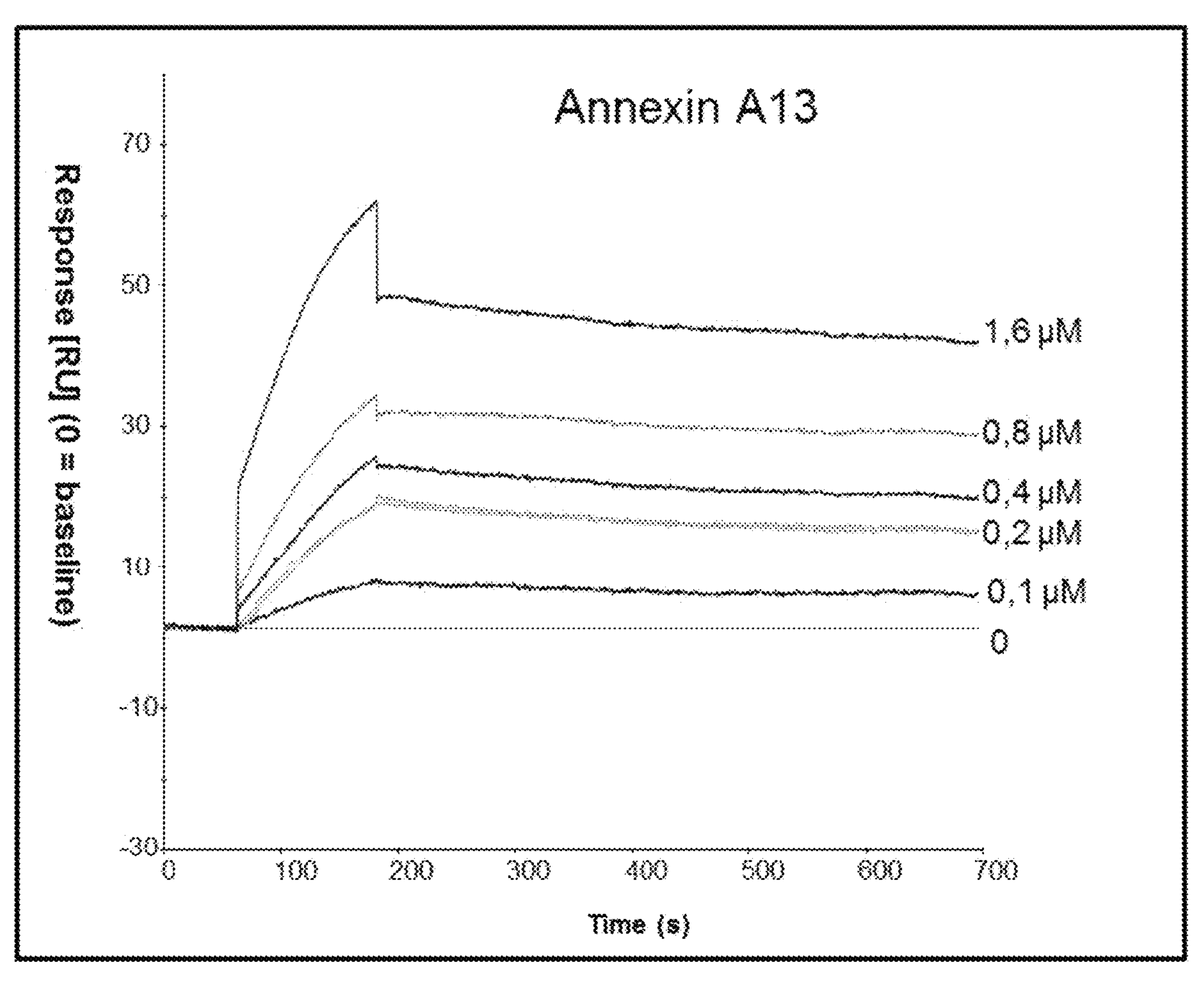

Tolerance induction by AnxA1, AnxA5 and AnxA13 is independent of DC apoptosis, recognition of annexins by FPR family members or inhibition of $PLA_2$ activity. The cytosolic form of $PLA_2$ ($cPLA_2$) has been described to be the key enzyme for signal transduction of inflammation (55, 56). Inhibition of $cPLA_2$ is mediated by specific interaction of $cPLA_2$ and the amino acids 275-346 of AnxA1. Other annexins, including AnxA5, do not inhibit $cPLA_2$ activity in vitro (57). Since AnxA5 and AnxA13 promote the development of tolerogenic DCs, inhibition of $cPLA_2$ is not required for suppression of DC activation by annexins. High amounts of AnxA1 released into the inflammatory fluid accelerate apoptosis of neutrophils and monocytes, which contributes to the resolution of inflammation (58-60). AnxA5 can have pro-apoptotic or anti-apoptotic effects depending on the cell type investigated (47, 61). Importantly, pre-incubation of BMDCs with AnxA1, AnxA5 or AnxA13 did not influence apoptosis progression, ruling out DC apoptosis as a mechanism for tolerance induction by annexins (FIG. 4, 12).

The inventors' results show that several annexin family members translocate to the surface of ACs and induce tolerogenic signaling upon recognition by their cognate receptor on DCs. The absence of severe phenotypes in mice deficient in individual annexin family members and almost identical tissue-specific expression patterns of most similar annexin genes suggest that annexins have redundant functions in vivo (12, 25, 28-31). In fact, redundant functions for different annexins have been reported in the context of membrane trafficking, inhibition of phospholipase activity and of blood coagulation in vitro (12). In a non-inflammatory or non-infectious setting and on a mouse background not prone to develop autoimmunity $AnxA1^{-/-}$ mice lack symptoms of autoimmune or chronic inflammatory diseases (FIG. 6). This is likely due to upregulation of other—equally suppressive—annexin family members in $AnxA1^{-/-}$ mice (FIG. 6, (32)).

The better understanding of tolerogenic signals on ACs provides new opportunities to interfere with peripheral tolerance induction for treatment of autoimmune diseases, chronic inflammatory diseases and cancer. The clearance of apoptotic tumor cells by tumor-associated macrophages or DCs is associated with release of anti-inflammatory cytokines and tolerance induction to tumor antigens (64). The immunoregulatory environment established by the tumor, and the presentation of tumor antigens in the absence of danger signals may account for the failure of most anticancer chemotherapies to promote curative T cell immunity (65). One powerful approach to counteract tolerogenic properties of the tumor is to induce immunogenic cell death if alarmins are released during apoptosis (66). The release of alarmins, however, has severe side effects, including promotion of angiogenesis, resistance to chemotherapeutics, chronic inflammation, development of gout or renal failure (64). The inventors' data can guide the development of an alternative approach, i.e., interference with the presentation of tolerogenic signals, e.g., annexins, or blockade of those on dying tumor cells with the goal to maximize cancer immunotherapy.

The following figures, sequences, and examples merely serve to illustrate the invention and should not be construed to restrict the scope of the invention to the particular embodiments of the invention described in the examples. All references as cited herein are hereby incorporated in their entirety by reference.

Figure 1B:
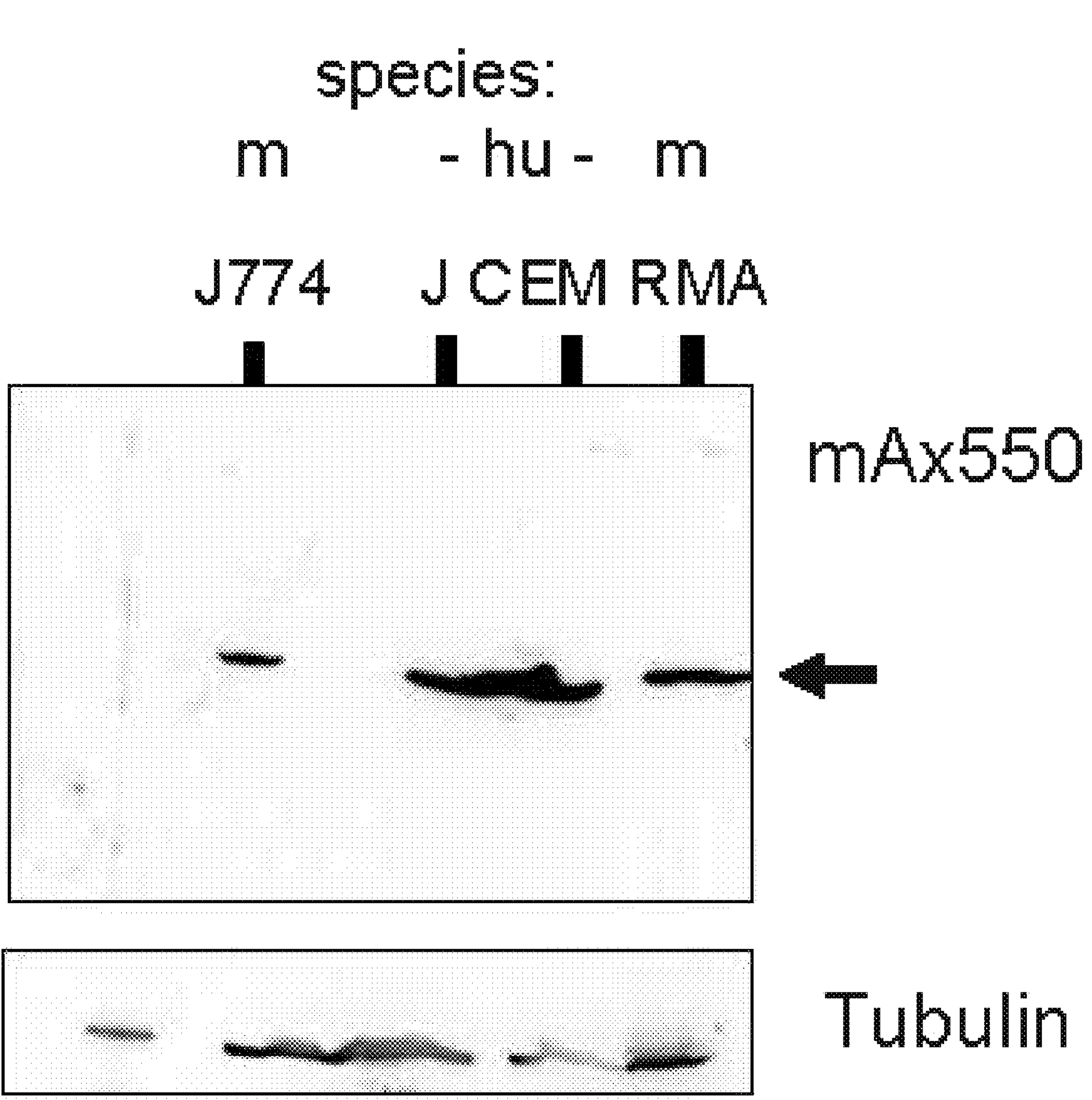
Figure 1C:
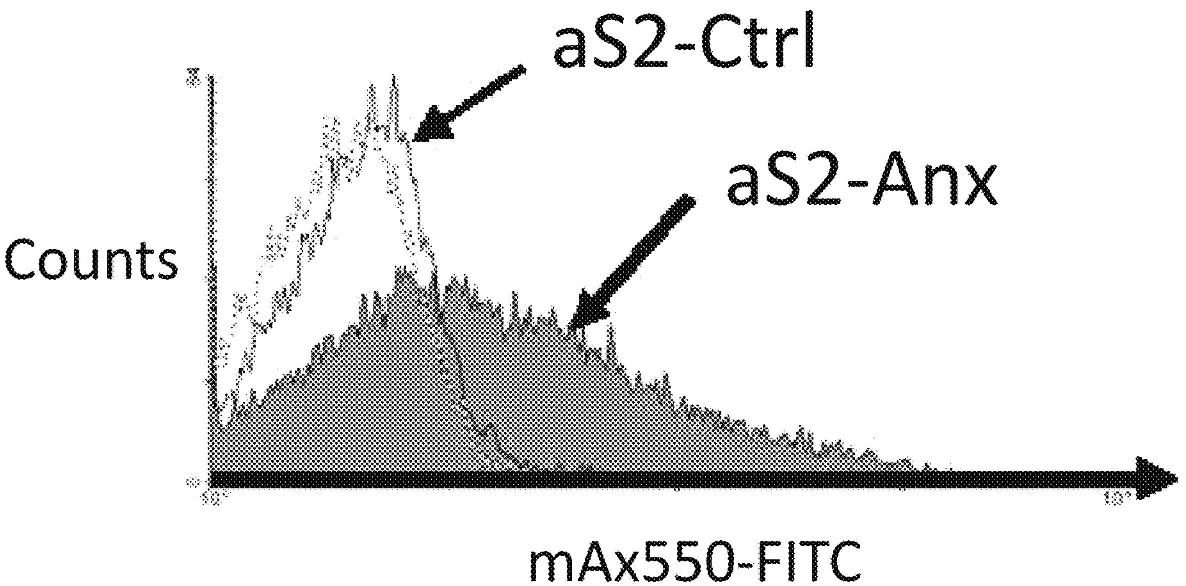

FIG. 1 shows that antibody mAx550 binds to human and murine annexin A1. FIG. 1A The antibody mAx550 binds to plate coated murine annexin A1 (mAnx1) but not to plate coated bovine serum albumin (BSA) used as negative control. FIG. 1B Western blot of different postnuclear lysates of the indictaed human (hu) and murine (m) cell lines were probed with the antibody mAx 550 followed by a secondary HRP-coupled anti-mouse Ig antibody. Tubulin was detected as loading control. The arrow denotes the specific annexin A1 band of 37 kDa. FIG. 1C The antibody mAx550 was coupled to Fluoroesceinisothiocyanate (FITC) and used to stain apoptotic Schneider cells (aS2), which were transfected with murine annexin A1 (Anx, grey shaded histogram) or an empty plasmid (Ctrl, black line). Unstained cells are shown as control (hatched line). Binding of mAx550-FITC was detected by flowcytometry.

Figure 2A:
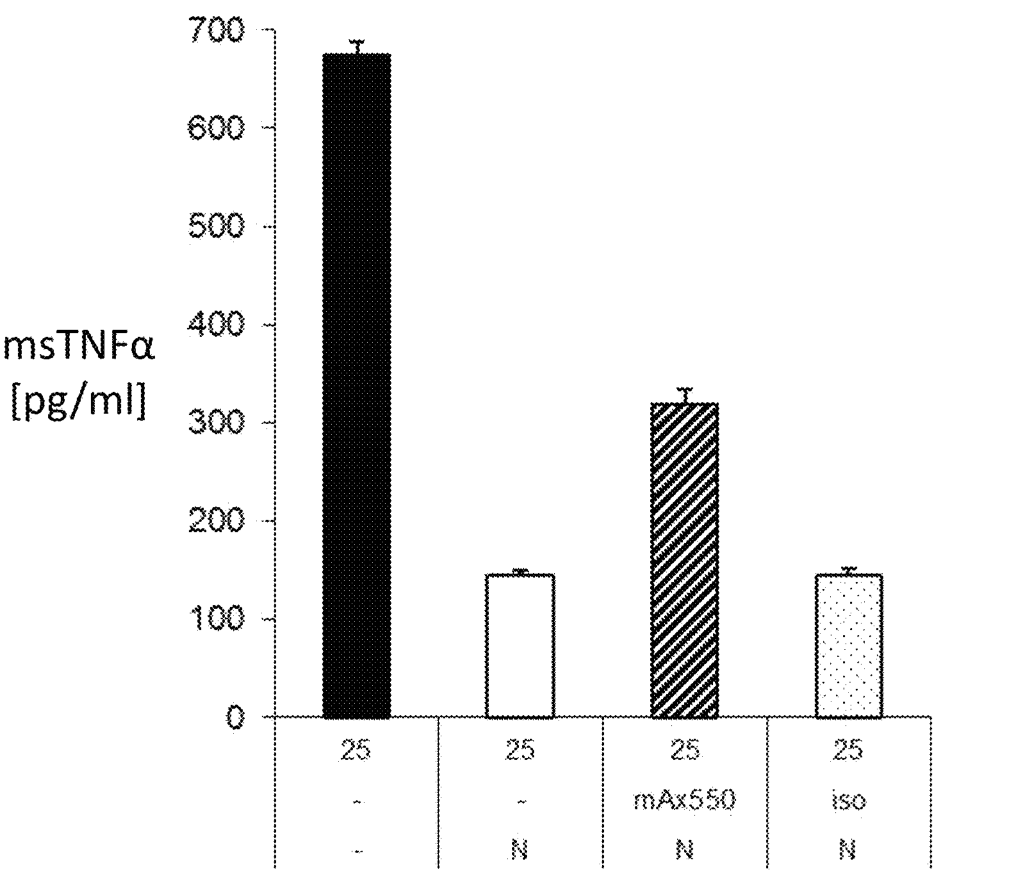
Figure 2B:
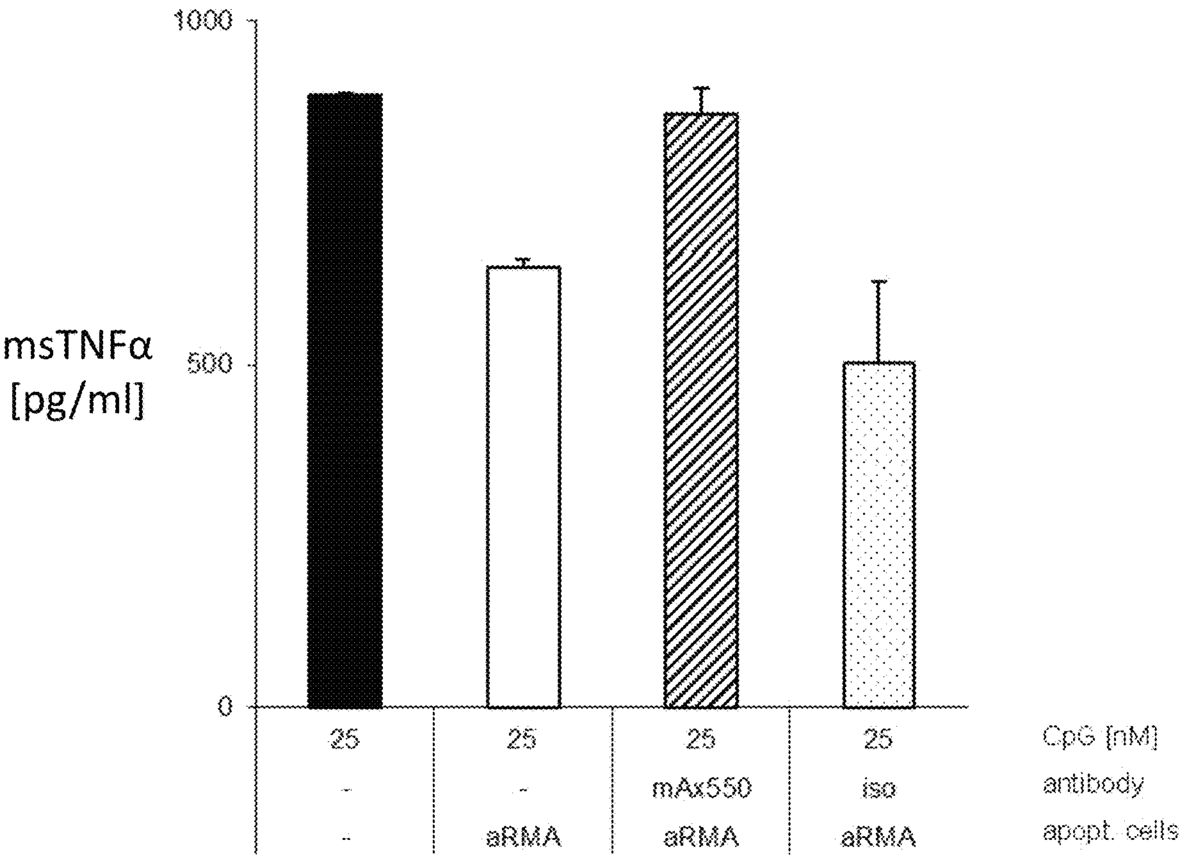
Figure 3A:
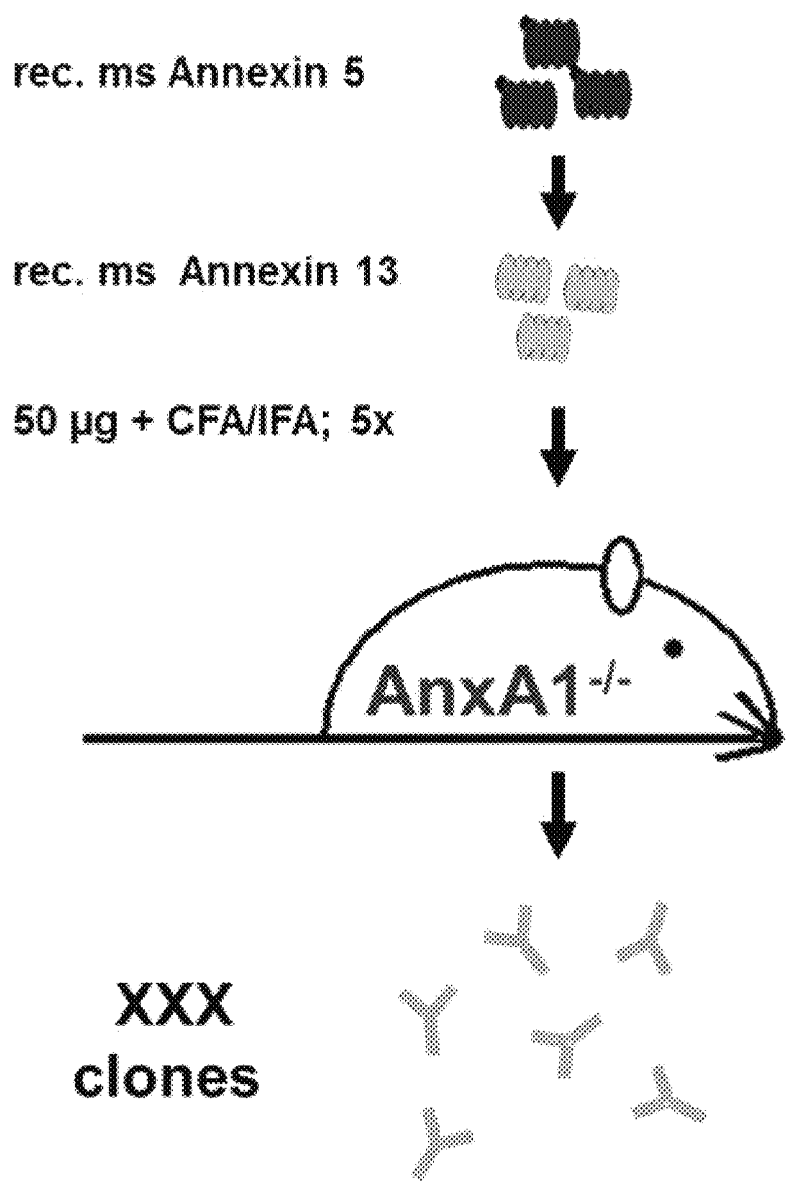
Figure 3B:
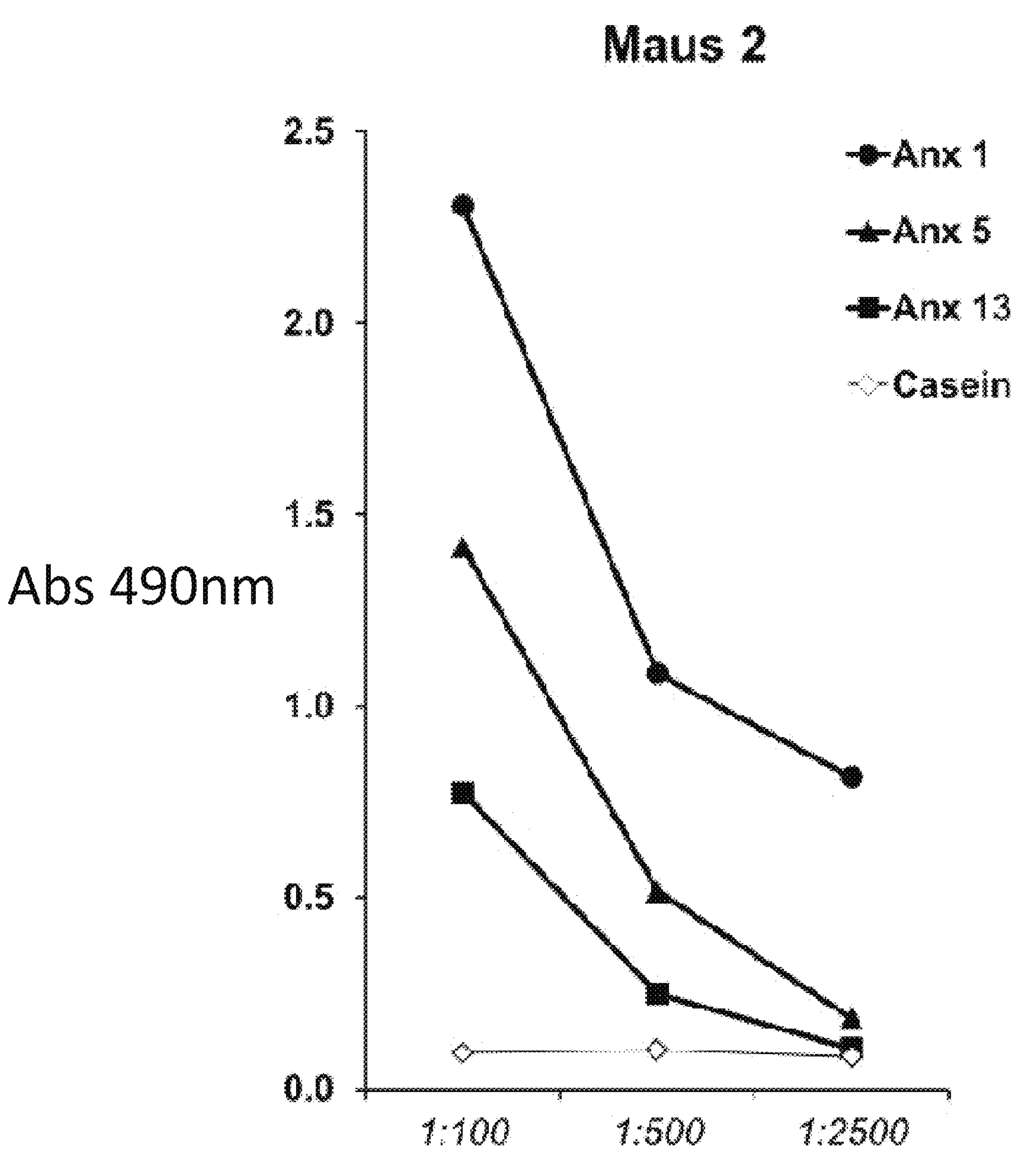
Figure 3C:
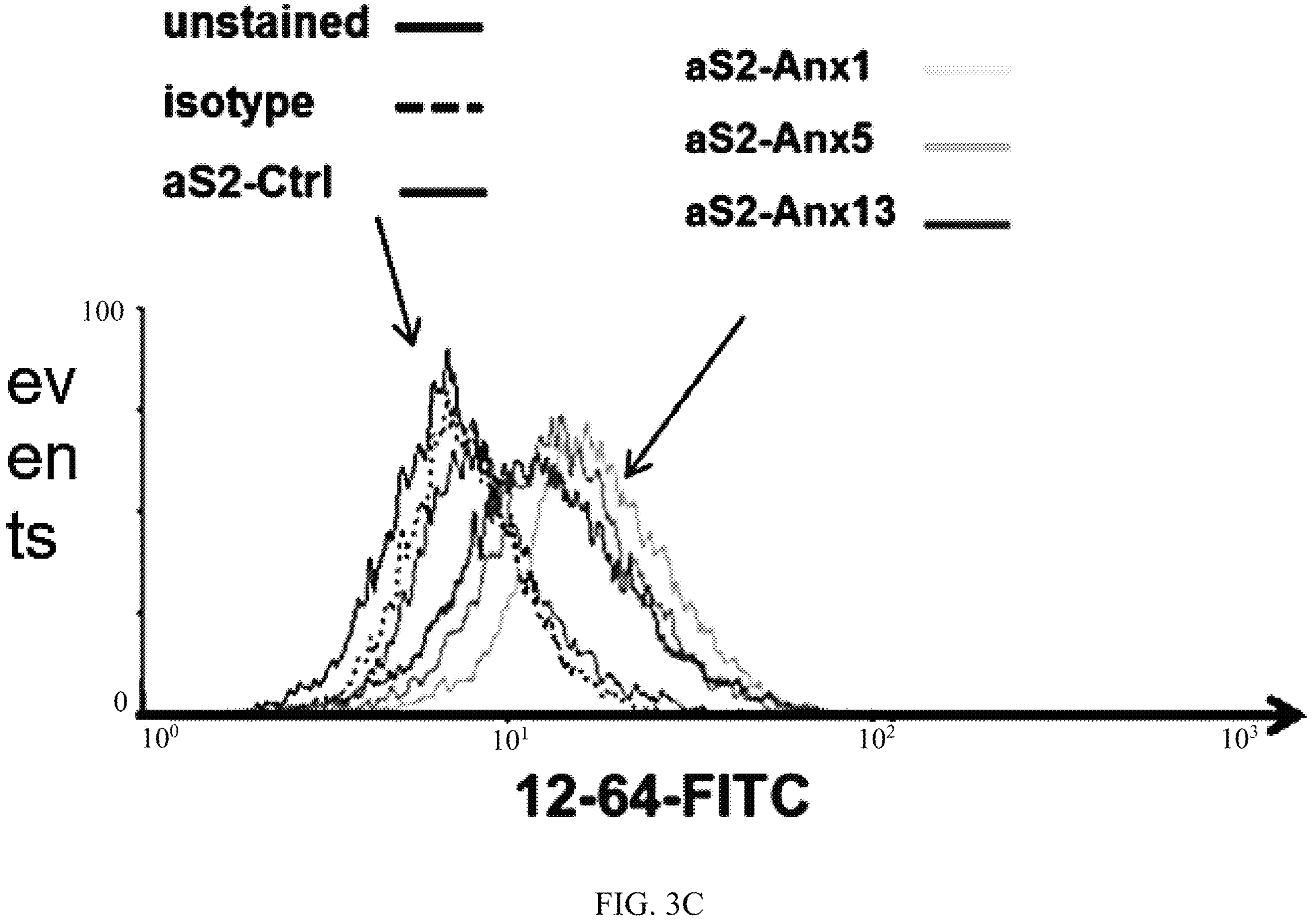
Figure 3D:
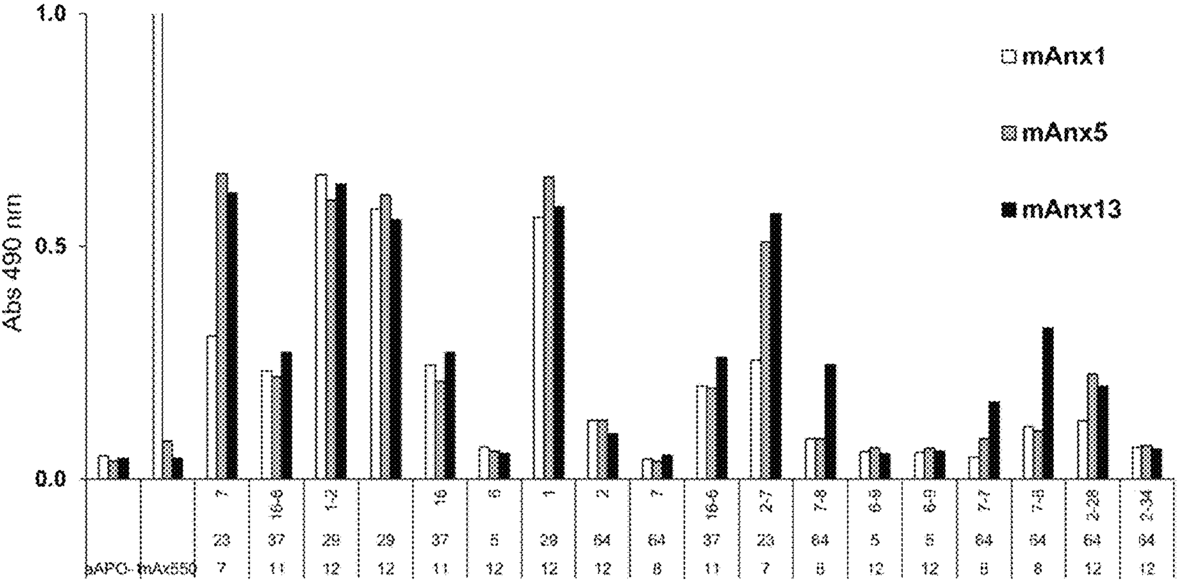

FIG. 2 shows that antibody mAx550 blocks the suppressive effect of apoptotic cells in vitro. Apoptotic murine neutrophils (N, FIG. 2A) or apoptotic RMA cells (aRMA, FIG. 2B) were preincubated with the antibody mAx550 (striped column), an isotype control antibody (iso, dotted column) or left untreated (-, white column). Apoptotic cells were then coincubated with murine bone marrow derived dendritic cells for 4h. Subsequently, cocultures were stimulated with the indicated amounts of CpG. Murine TNFα (mTNFα) in culture supernatants was analyzed by ELISA.

FIG. 3 shows the generation of antibodies against several annexins. FIG. 3A presents an Immunization scheme. Annexin A1 knockout mice ($ANXA1^{-/-}$) were immunized with recombinant murine (ms) annexin A5 in complete Freund's adjuvants, followed by 4 alternating boosts of recombinant murine annexin A13 and annexin A5 in incomplete Freund's adjuvants. XXX=antibodies that bind at least 3 different annexins. Right panel shows serum titer against the indicated proteins of one immunized mouse in ELISA. FIG. 3D) Screening Method. Supernatants of individual hybridomas were screened for binding to immobilized recombinant murine (m) annexins A1, A5 and A13 in ELISA. The antibodies anti-APO-1 (aAPO-1) and mAx550 were used as negative and positive controls, respectively. FIGS. 3B and 3C The monoclonal XXX-antibody 12.64 was coupled to Fluorescein isothioncyanate (FITC) and used to stain apoptotic Schneider cells (aS2), which were transfected with murine annexin A1, annexin A5 or annexin A13 (Anx) or an empty control plasmid (Ctrl). Binding of 12.64-FITC was detected by flow cytometry. Unstained and isotype-stained apoptotic cells are shown as control.

FIG. 4 shows that various Annexins bind to the receptor LRP-1 with high affinity. Binding of the indicated recombinant annexins and the annexin A1 core domain to immobilized LRP-1 was detected by quartz crystal microbalance. Recombinant annexins were analyzed at 3 different concentrations. Depicted are fitted binding curves of the indicated annexins and the annexin A1 core domain to LRP-1. The calculated affinities for all annexins and the core annexin A1 domain range from 50-300 nM. Murine annexin A1 (mAnxA1): filled circles; murine annexin A1 core domain (mAnxA1 core): open circles; murine annexin A5 (mAnxA5): filled squares; murine annexin A13 (mAnxA13): open squares (manuscript in preparation).

FIG. 5 shows that several annexins bind to the receptor Dectin-1 with high affinity. FIG. 5A Analysis of the binding of recombinant annexin A1 (Annexin I) and annexin A5 (Annexin V) to the indicated, immobilized C-type lectin molecules in ELISA. FIG. 5B-5E Surface plasmon resonance spectroscopy sensorgrams of the binding of murine annexin A1 (FIG. 5B), annexin A1 core domain (FIG. 5C), annexin A5 (FIG. 5D), and annexin A13 (FIG. 5E) to the surface molecule Dectin-1. The indicated concentrations of the indicated recombinant annexins were allowed to bind to immobilized Dectin-1 and bound molecules were measured by surface plasmon resonance. Annexin affinities to Dectin-1 were calculated to be in the nanomolar range (~100 nM) (manuscript in preparation).

Figure 6A:
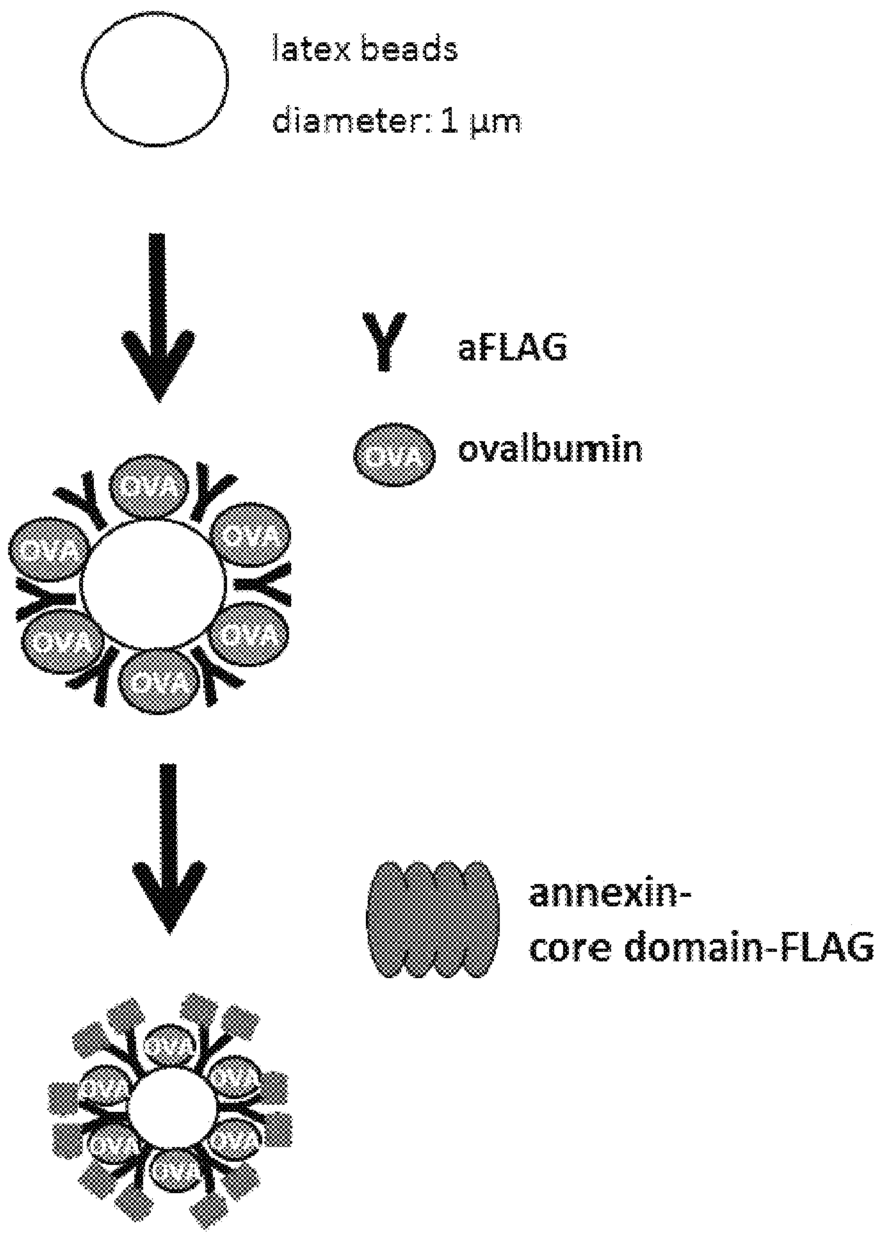
Figure 6B:
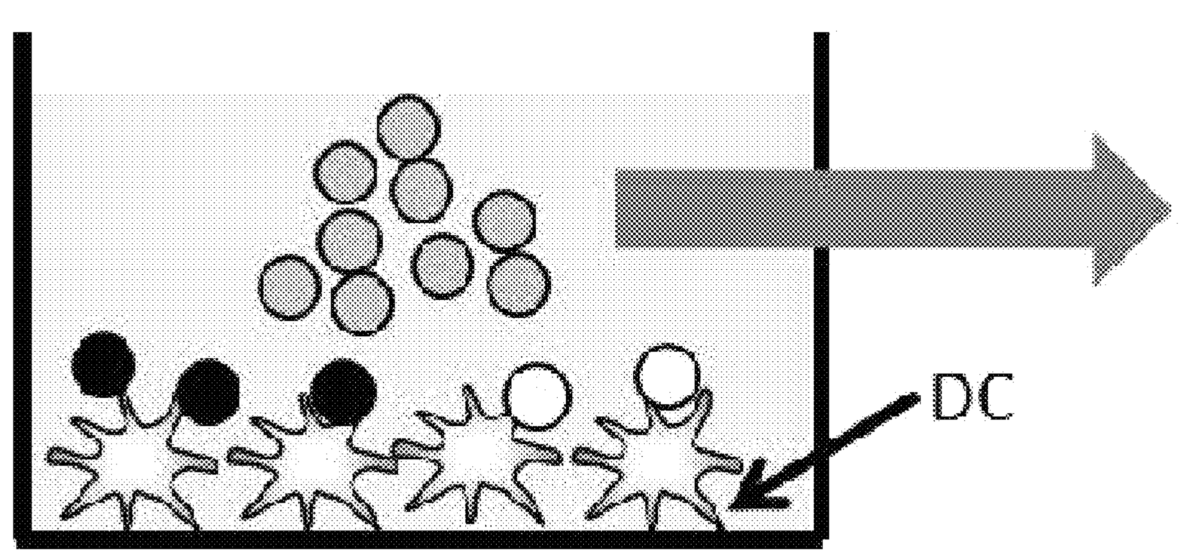
Figure 6C:
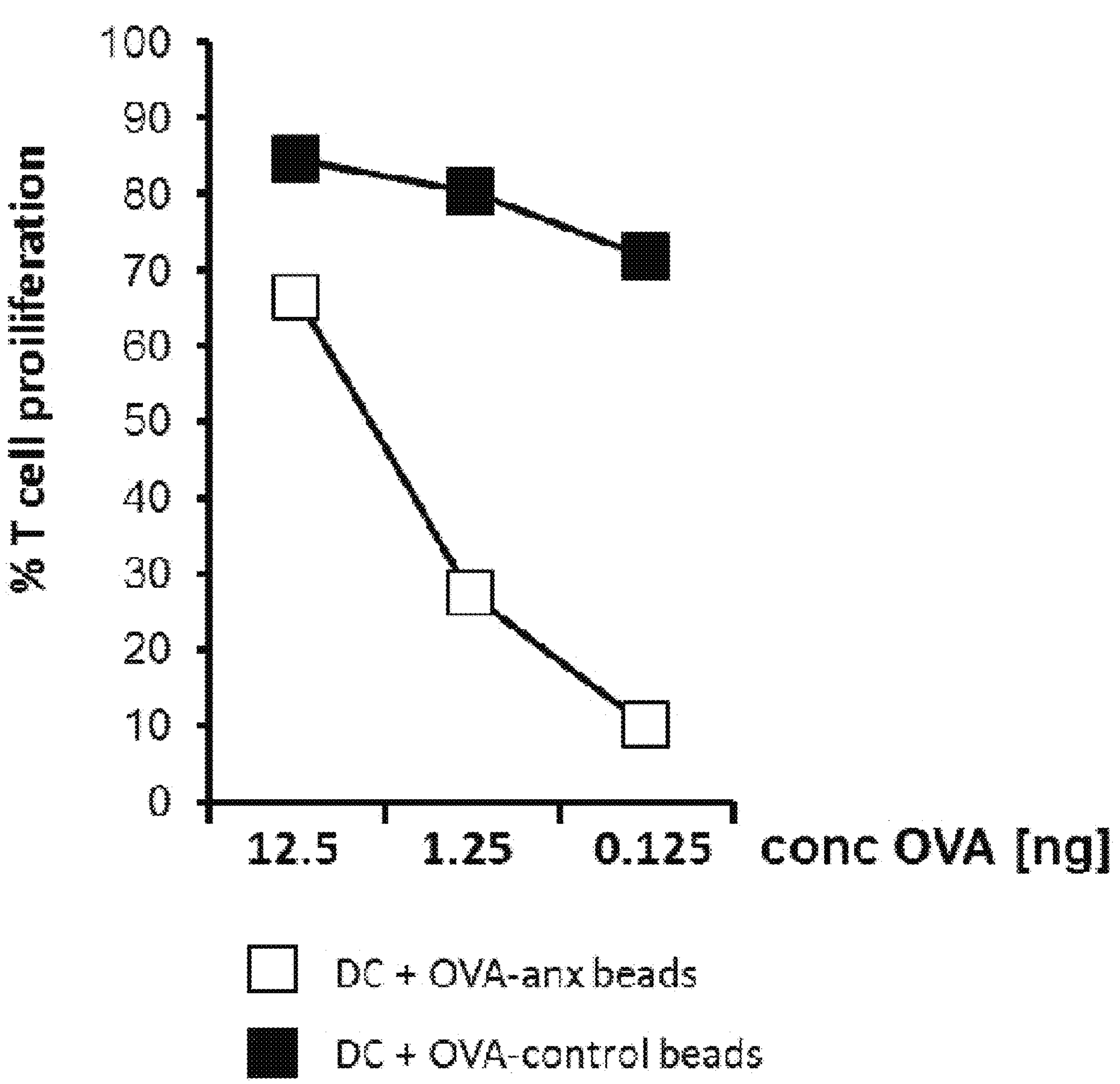
Figure 7A:
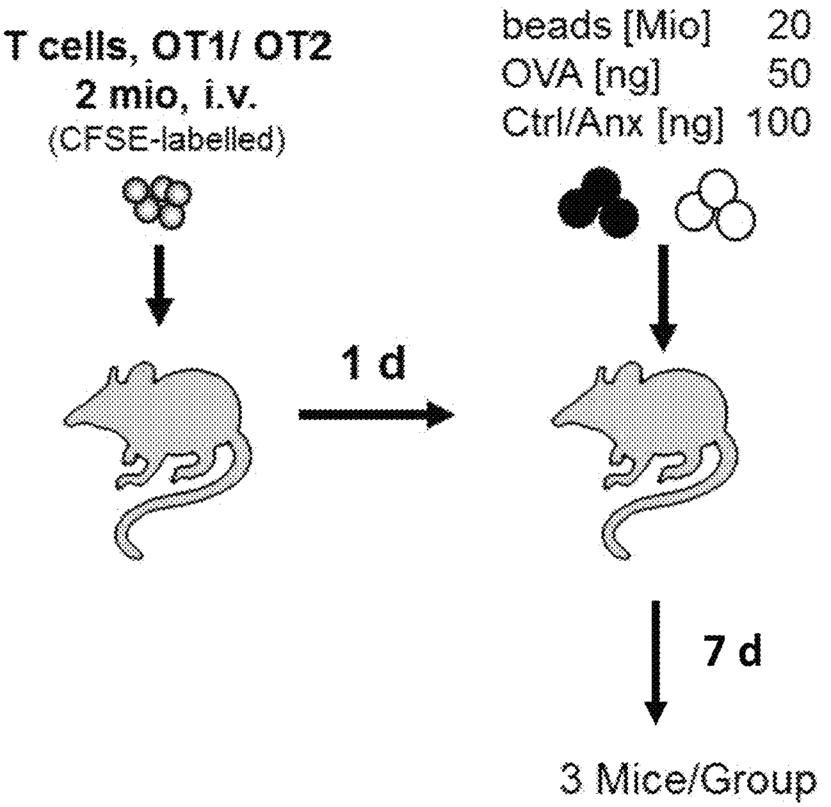
Figure 7A:
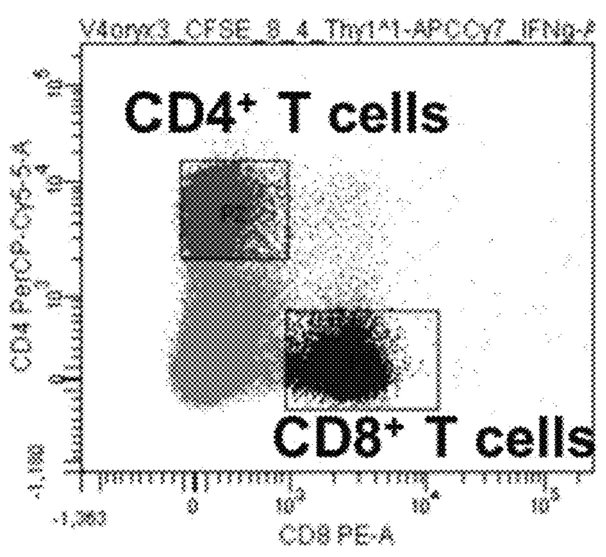
Figure 7B:
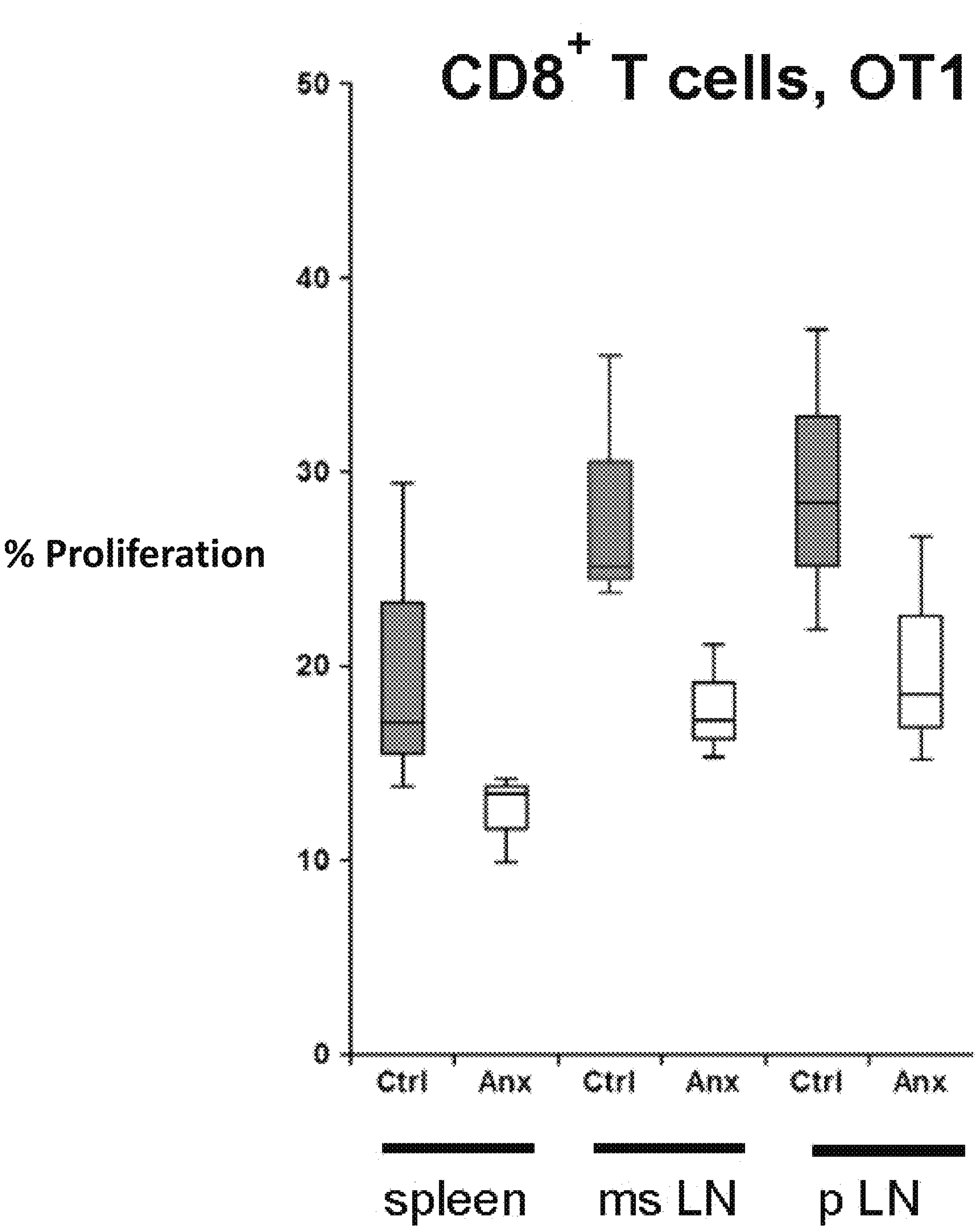
Figure 7C:
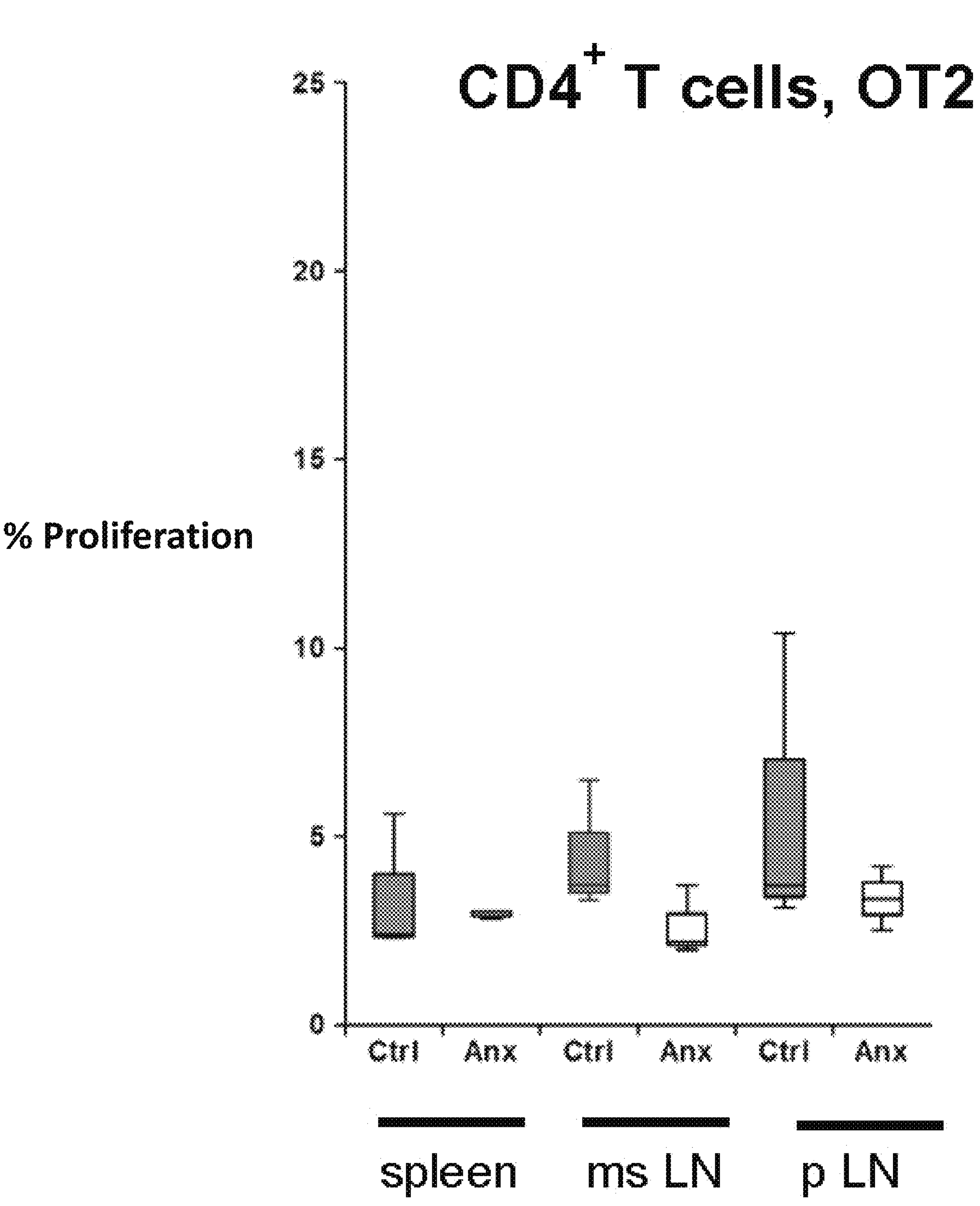
Figure 7D:
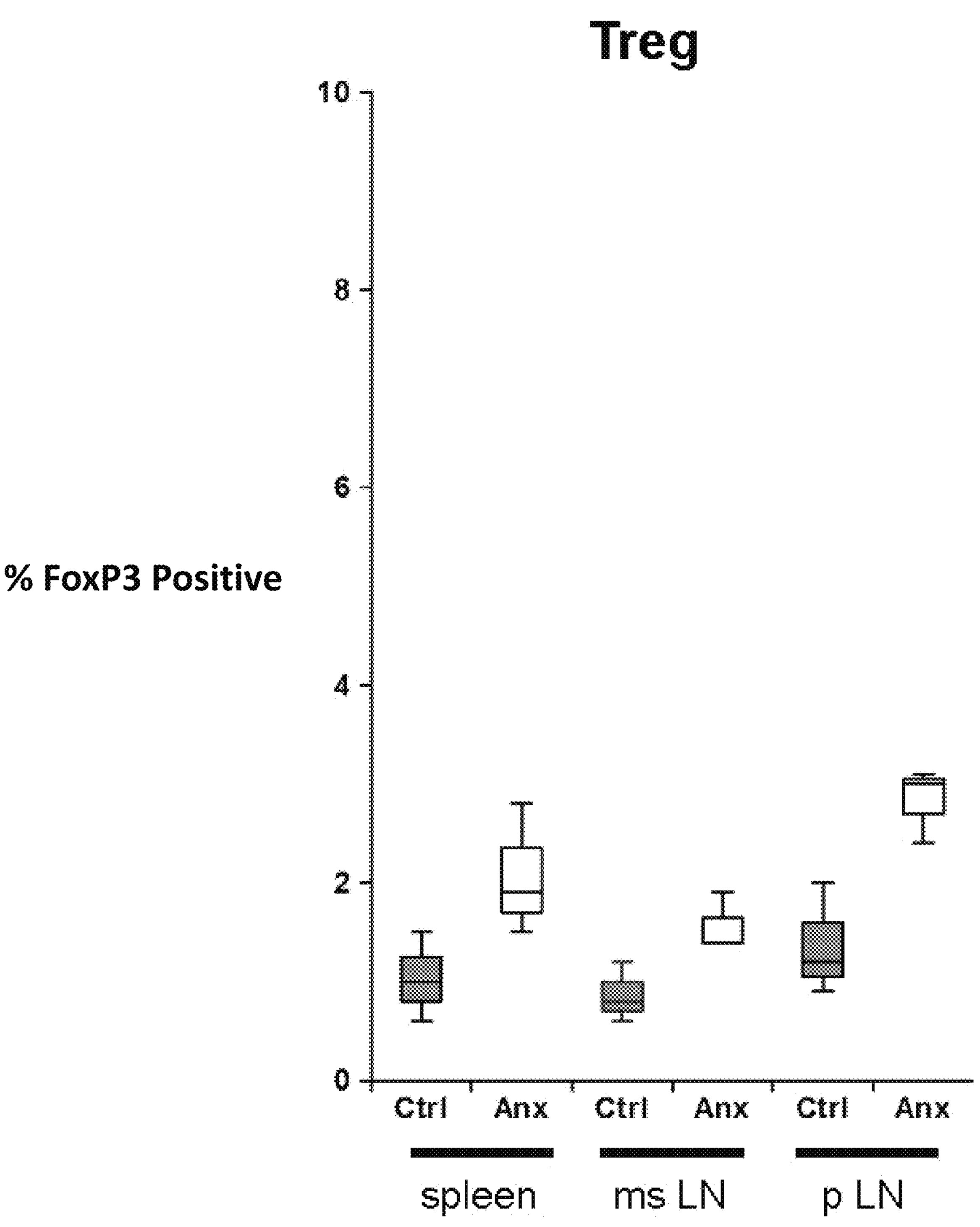

FIG. 6 shows the preparation and effect of antigen-coupled annexin-beads. FIG. 6A Fluorescent latex beads (surface sulfatylated) were coated with anti-FLAG antibodies and ovalbumin (OVA). Thereafter, the annexin A1 core domain was coupled to the beads through its FLAG-tag. FIG. 6B Described OVA-annexin-beads were used in vitro for DC-mediated stimulation of OVA-specific T cells. As control, OVA-beads were coupled to a control protein (OVA-control beads). FIG. 6C shows T cell proliferation (measured as CFSE-dilution) resulting from stimulation by DC that were preincubated with OVA-annexin- or OVA-control protein-coupled beads, respectively.

FIG. 7 shows the effect of annexin-coupled antigen-beads in vivo. OVA-annexin-beads and OVA-control-beads as described in FIG. 6 were used for T cell stimulation in vivo. FIG. 7A Scheme of experiment. OVA-specific, CFSE-labeled T cells (CD4- and CD8-positive OT2 and OT1 cells) were injected into mice (i.v.). 1 d later OVA-annexin or OVA-control beads in indicated concentrations were injected (i.v.). FIGS. 7B-7C T cell-proliferation of OT1 and OT2-cells were measured by CFSE-dilution in flow cytometry gated on transferred $CD4^+$ (FIG. 7C) and $CD8^+$ (FIG. 7B) T cells in spleens, mesenteric (msLN) and popliteal lymph nodes (pLN) of 3 mice. FIG. 7D The percentage of regulatory T-cells (Treg) within the population of OT2-cells was estimated by measuring the Treg-specific transcription factor FoxP3.

Figure 8A:
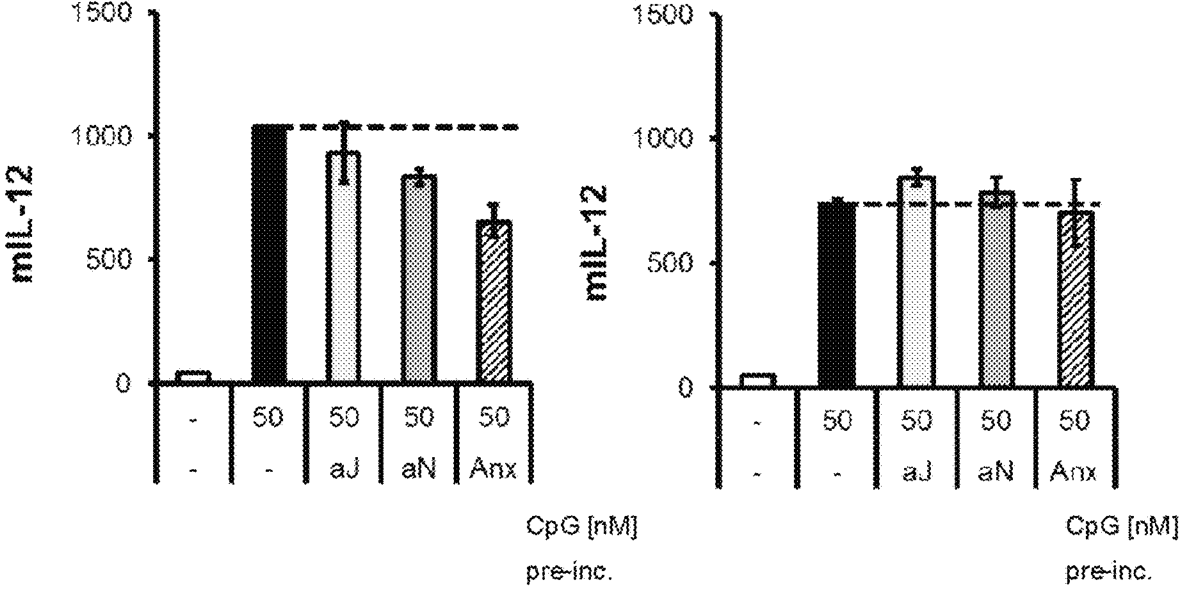
Figure 8B:
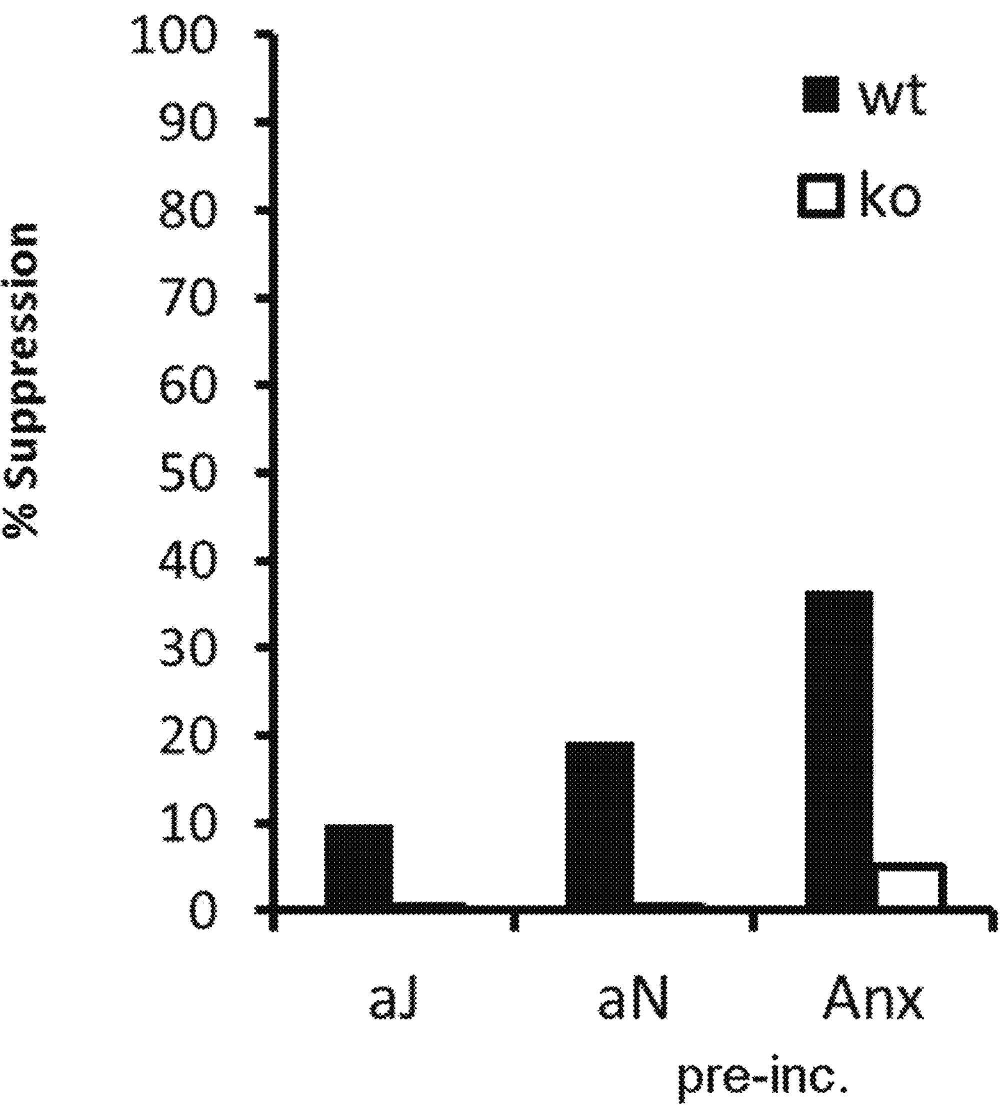
Figure 9A:
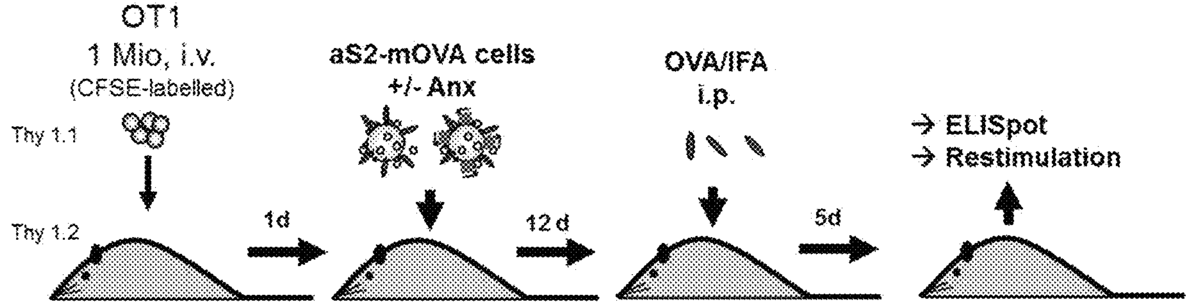
Figure 9B:
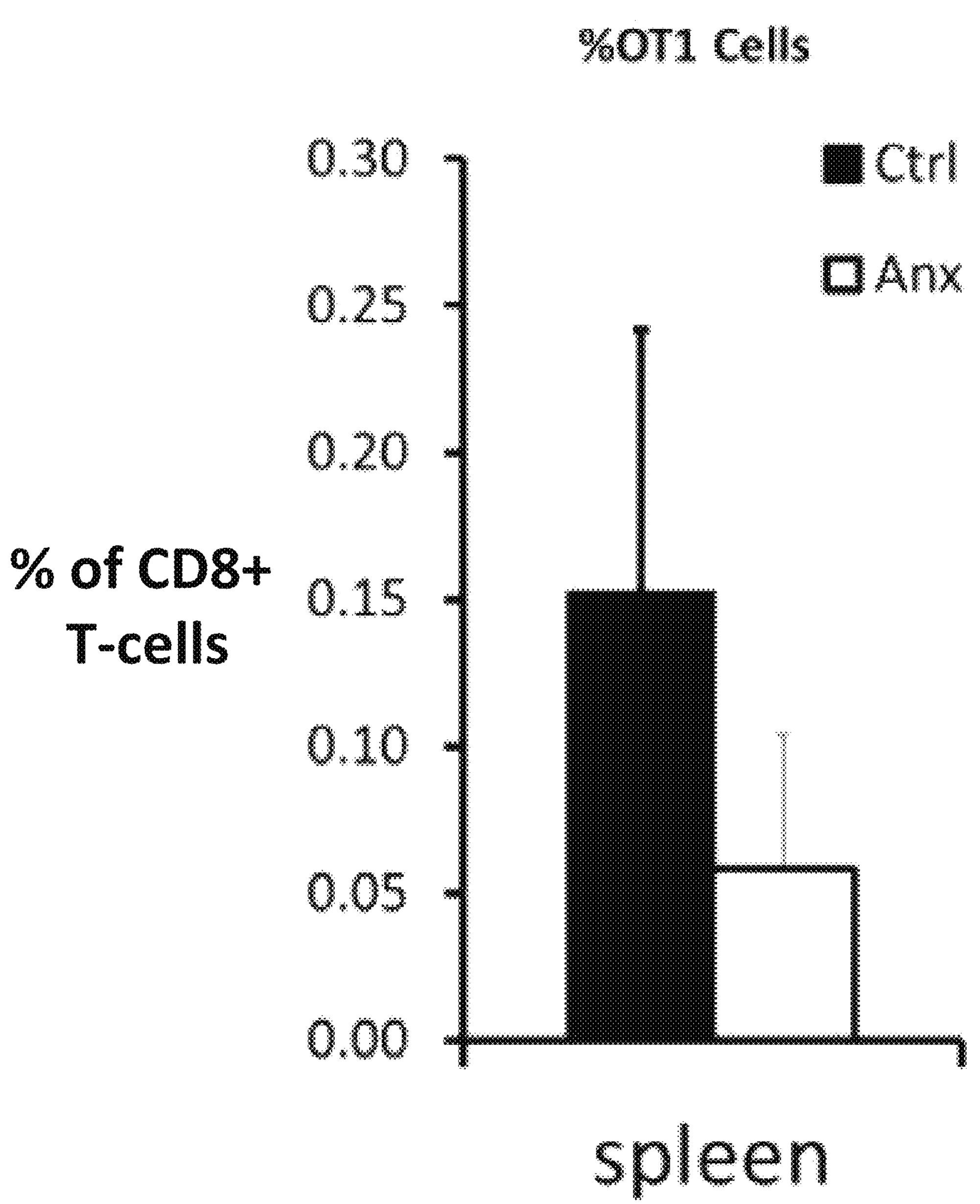
Figure 9C:
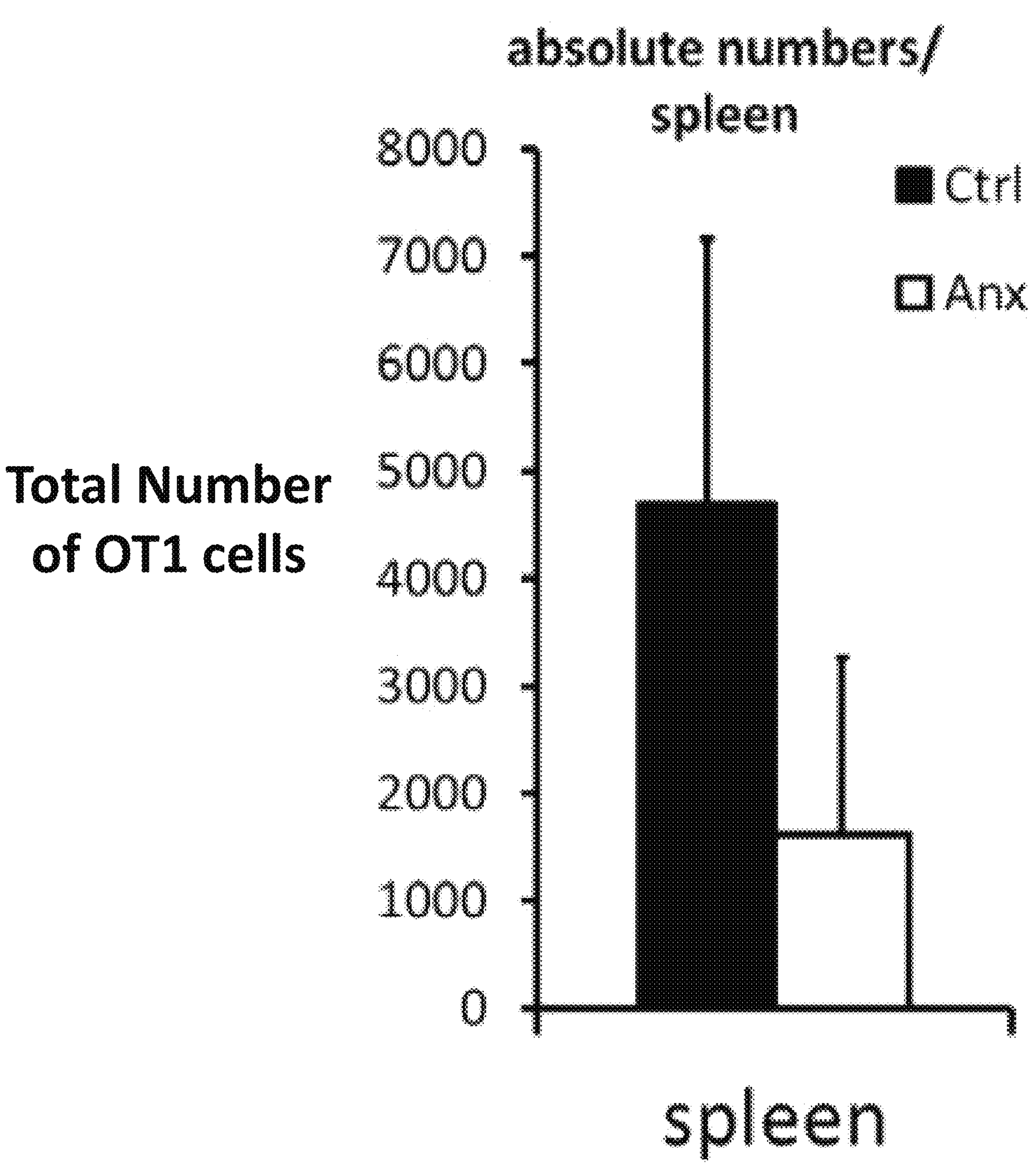
Figure 9D:
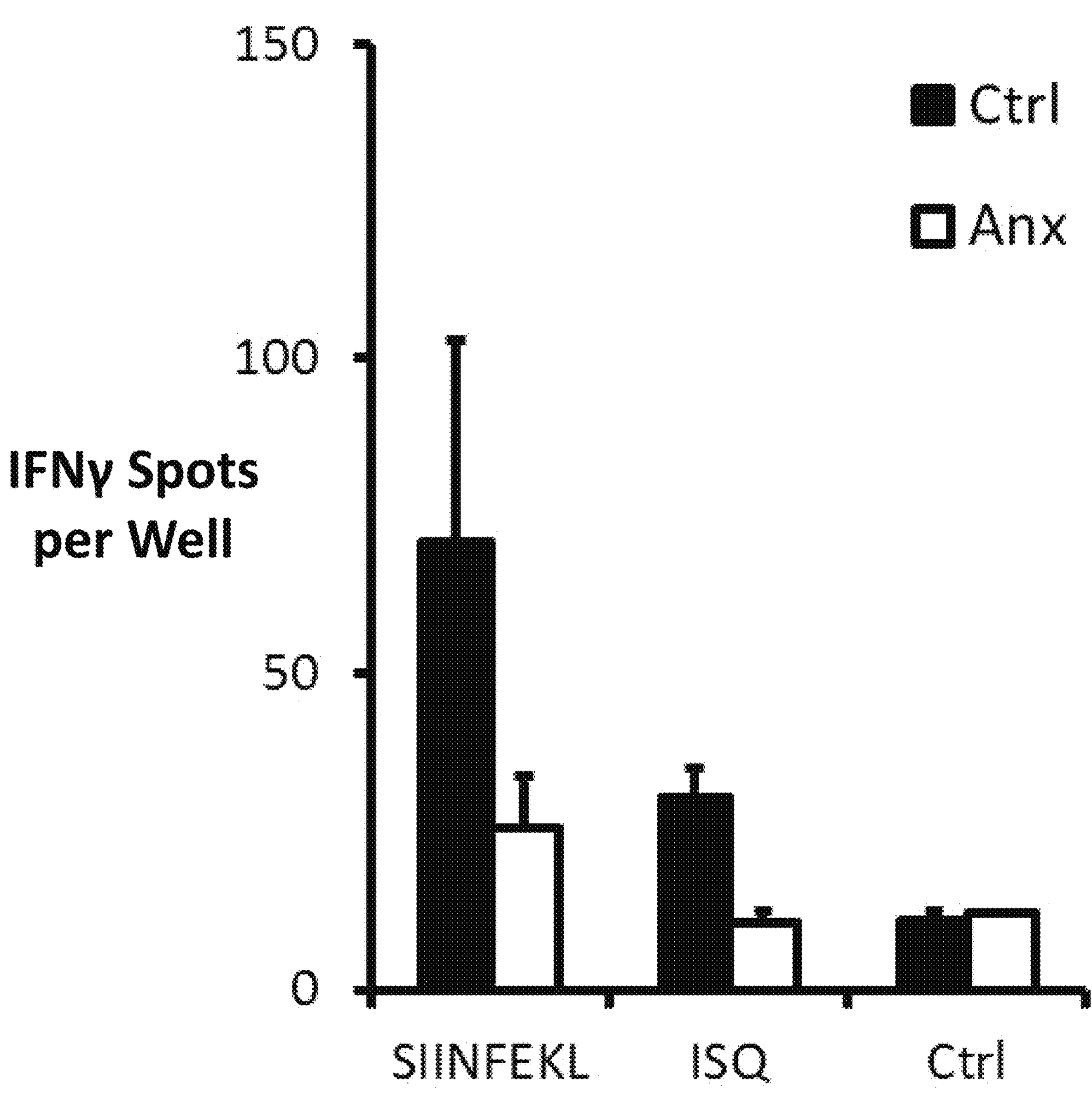
Figure 9E:
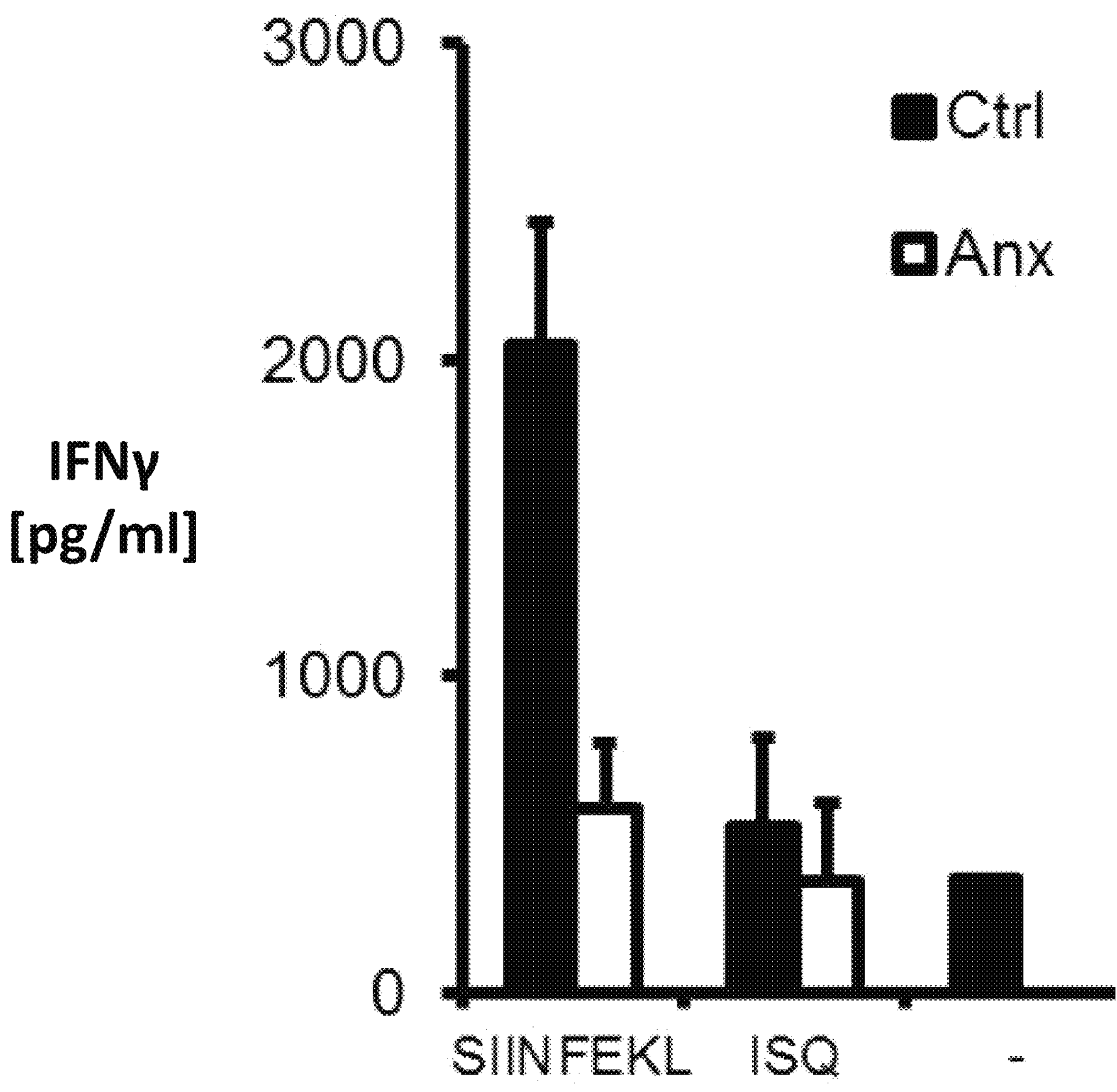

FIG. 8 shows that the suppressive activity of annexin is mediated via Dectin-1. FIG. 8A Immature murine DC of wt mice (wt) or Dectin-1 deficient mice (Dectin-1 ko) were preincubated (pre-inc.) with apoptotic neutrophils (aN), apoptotic Jurkat T cells (aJ) or recombinant annexin (Anx, 500 nM). Subsequently, cultures were stimulated with CpG (50 nM), and the concentration of murine Interleukin-12 (mIL12) in culture supernatants was determined by ELISA. Error bars represent means+/−s.d. of triplicate cultures. Data are representative of 3 independent experiments. FIG. 8B The relative suppression of mIL-12 apoptotic neutrophils (aN), apoptotic Jurkat T cells (aJ) or recombinant annexin (Anx, 500 nM) compared to stimulated DC alone was calculated for wt DC (wt) and Dectin-1 deficient DC (ko).

FIG. 9 shows that annexin induces T cell depletion and reduced T cell activity. FIG. 9A Scheme of experiment. OVA-specific, CFSE-labeled CD8-positive OT1 T cells were injected into mice (i.v.). 1 d later apoptotic OVA- and annexin (Anx) or control-vector (Ctrl)-transfected S2 cells (aS2) were injected (i.v.) as well. After 12 days all mice were boosted with recombinant OVA in incomplete Freund's adjuvants (IFA). After another 5 d spleens of all mice were analyzed by flow cytometry and ELISpot. FIGS. 9B-9C The numbers of remaining transferred OT1 cells were counted relative to all CD8-positive T cells (FIG. 9B). FIG. 9C shows the total amount of transferred OT1 cells per spleen. FIGS. 9D-9E The activity of CD4- and CD8-positive T cells in spleens of all mice was analyzed by ELISpot or restimulation in vitro against an OVA-derived MHC class I dependent peptide (SIINFEKL) or an MHC class II dependent peptide (ISQ) in comparison to a control peptide (Ctrl). The activity was measured as Interferon (IFN)-γ-ELISpots or IFN-γ-secretion in ELISA.

Figure 10:
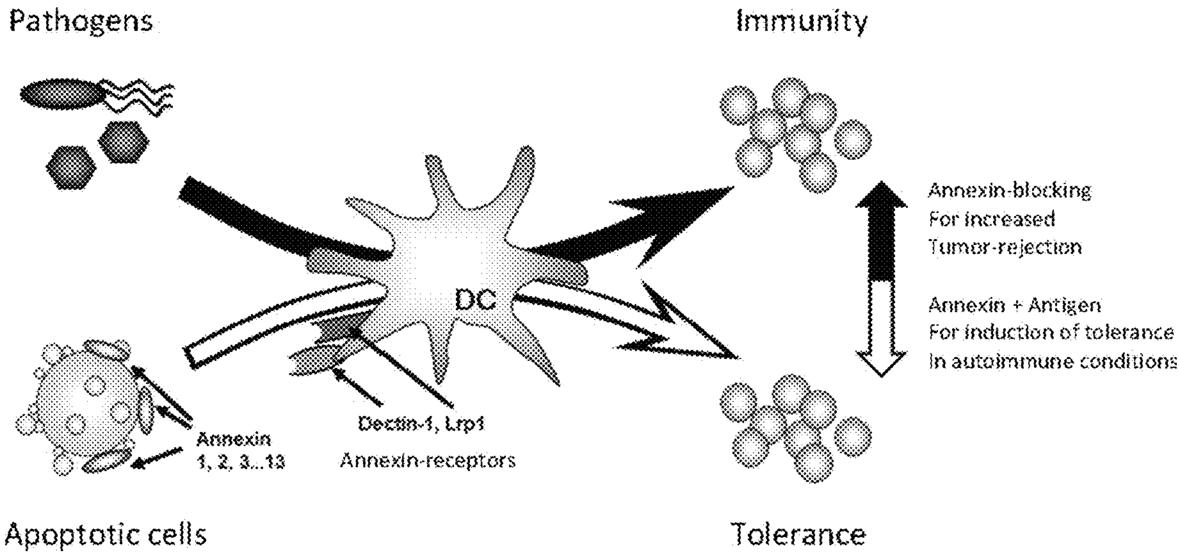

FIG. 10 shows the scheme of the annexin checkpoint system. Annexins on apoptotic cells counteract pro-inflammatory pathogenic stimuli and induce tolerance to autoantigens derived from apoptotic cells. Annexins act via specific annexin receptors (Dectin-1, DC-SIGN, LRP-1) on dendritic cells (DC) and impose a tolerogenic DC-phenotype, which results in antigen-specific T cell depletion. This system can be utilized to induce tolerance against autoantigens involved in the development of autoimmune diseases. Blocking the annexin checkpoint system will induce immune reactivity against apoptotic tumor cells and, thus, tumor rejection.

Figure 11:
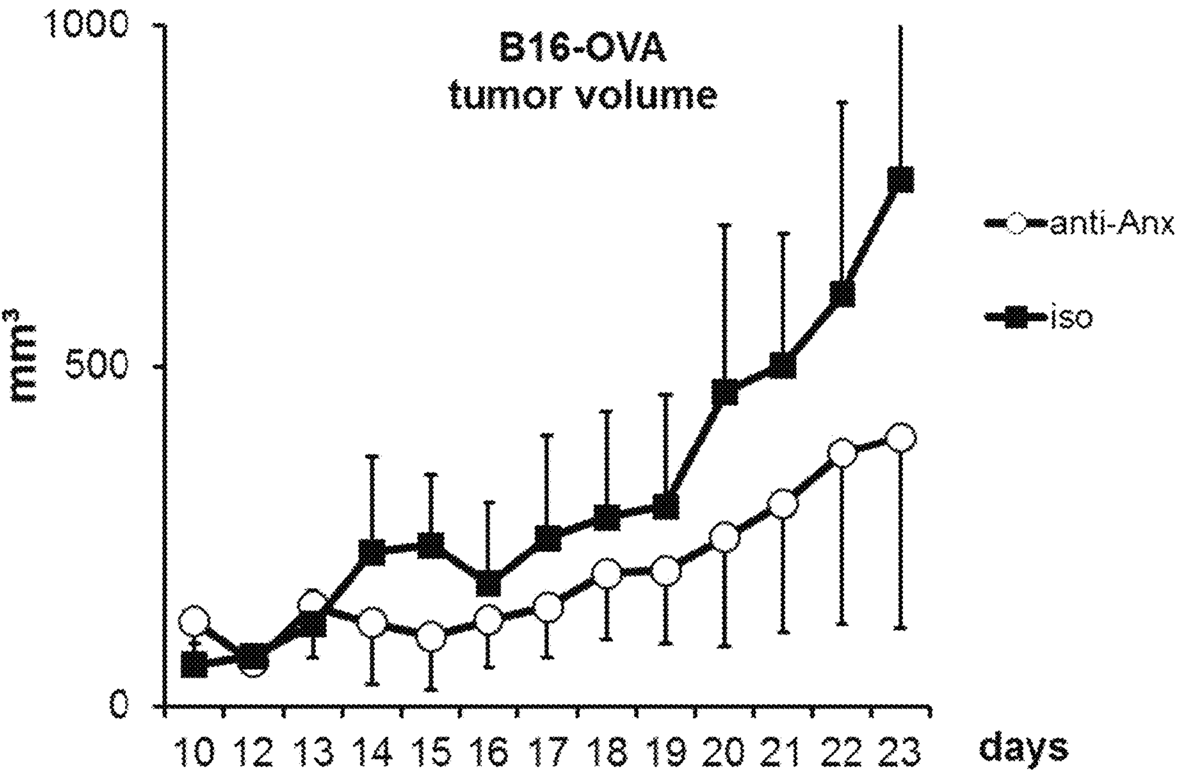

FIG. 11 shows blocking the annexin checkpoint system by anti-annexin antibodies reduces tumor growth. Mice (n=5/group) were injected with ovalbumin (OVA) expressing B16-melanoma cells (intracutaneously). On day 13, 14, 17, 24 and 28 mice were immunized with 150 μg of an anti-annexin antibody (anti-Anx) or the respective isotype control antibody (iso). Tumor growth of melanomas was analyzed by caliper.

FIG. 12 shows that the core domain of annexin mediates the tolerogenic effect of AnxA1. FIG. 12A Scheme of full length AnxA1 and the AnxA1 mutants AnxA1ΔN, AnxA1 mAF-2 and AnxA1ΔN mAF-2. FIG. 12B GM-CSF-differentiated BMDCs from $Tlr4^{-/-}$ mice were incubated with the indicated concentrations of recombinant protein. 6-8 h later, cells were stimulated with 40 nM CpG o/n. TNF-α concentrations in the supernatants were determined by ELISA. Data are mean±SEM of three independent experiments. FIG. 12C Quantification of mRNA levels of FPR1, FPR2 and FPR3 relative to GAPDH in neutrophils (NΦ) and GM-CSF-differentiated BMDCs by qRT-PCR. FIG. 12D Surface expression of FPR1, FPR2 and FPR3 on transiently transfected 293T or BMDCs was detected using the fluorescently labelled FPR ligands fMLF-fluorescein and WKYMVM-FAM. FIG. 12E GM-CSF-differentiated BMDCs from $Tlr4^{-/-}$ mice were incubated with the indicated concentrations of recombinant AnxA1 in the presence or absence of the FPR antagonists Boc-1 and/or Boc-2 or apoptotic Jurkat T cells (aJ, UV-C-irradiation 50 $mJ/cm^2$, 4 h), respectively. 6-8 h later, cells were stimulated with 40 nM CpG o/n. TNF-α concentrations in the supernatants were determined by ELISA. Data are mean±SEM of three independent experiments. FIG. 12F Immunoblot analysis of MAPK activation of BMDCs after incubation with 500 nM of recombinant AnxA1 for the indicated time points. Lysates of CpG- and LPS-stimulated BMDCs from $Tlr4^{-/-}$ and WT mice, respectively, served as positive controls. Data are representative of three independent experiments. FIG. 12G Immunoblot analysis of MAPK activation of BMDCs after incubation with fMLF for the indicated time points. Lysates of CpG- and LPS-stimulated BMDCs from $Tlr4^{-/-}$ and WT mice, respectively, served as positive controls.

Figure 13A:
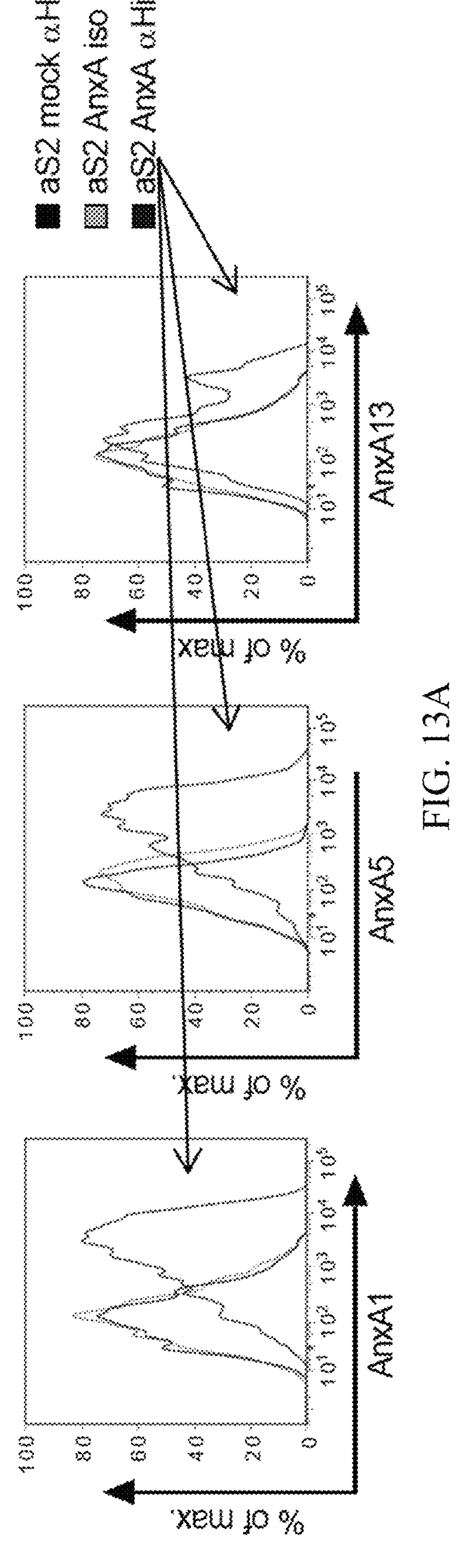
Figure 13B:
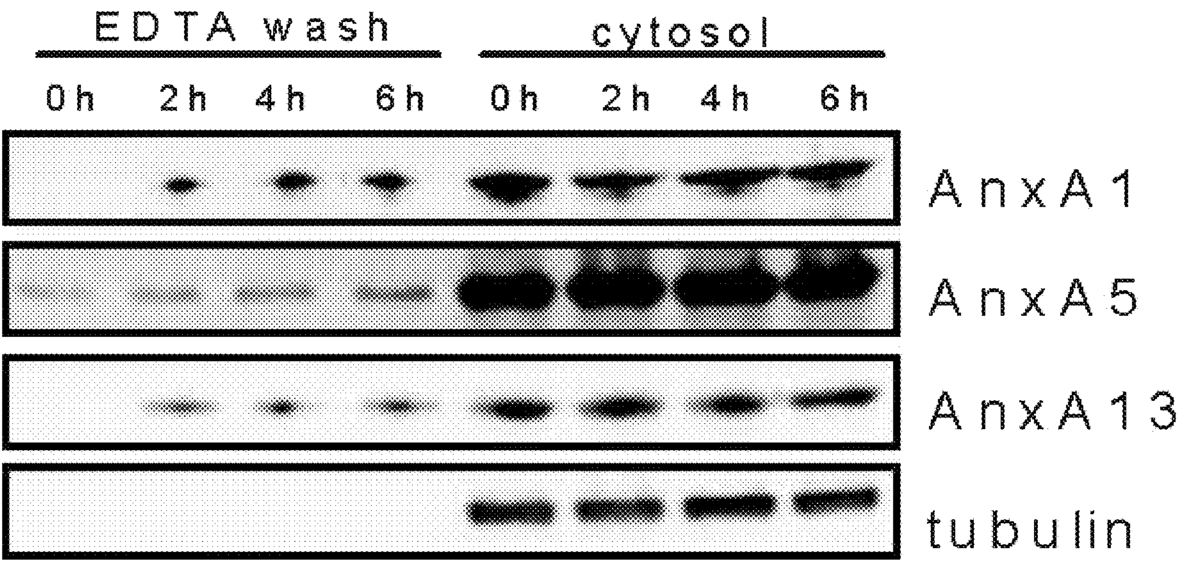
Figure 13C:
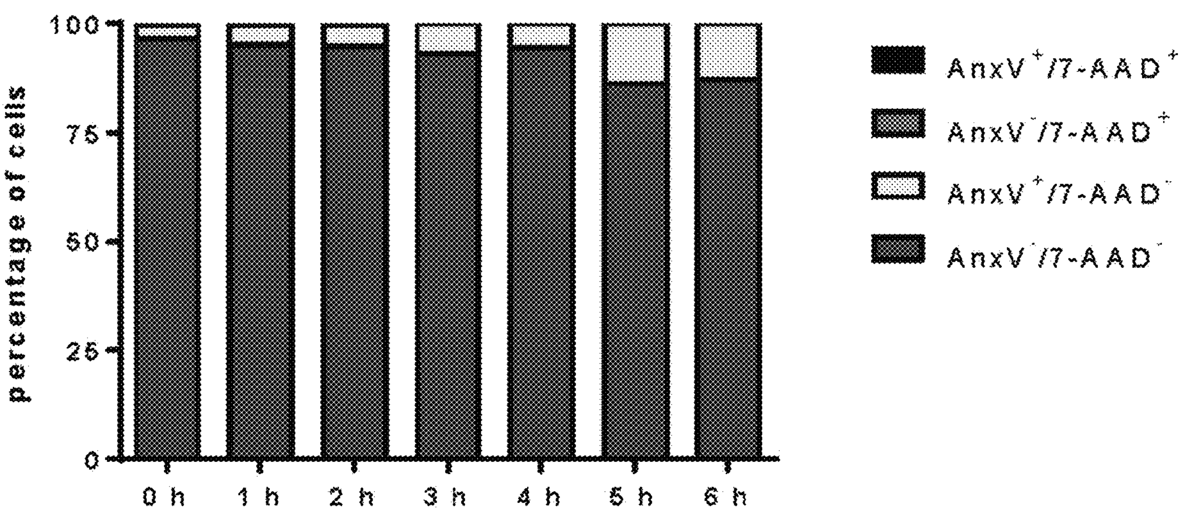

FIG. 13 shows that AnxA5 and AnxA13 translocate to the cell surface upon induction of apoptosis. FIG. 13A Flow cytometric analysis of aS2 cells. 16 h after UV-C irradiation (250 $mJ/cm^2$) mock or AnxA1/5/13-transfected aS2 cells were early apoptotic ($AnxV^+$/7-$AAD^-$) and stained using biotin-conjugated anti-6×His streptavidin-APC. FIG. 13B Immunoblot analysis of cytosolic and membrane fractions of viable (0 h) or early UV-C-irradiated apoptotic CEM cells (50 $mJ/cm^2$, 2-6 h). FIG. 13C Quantification of cell viability of UV-C-irradiated early apoptotic CEM cells of FIG. 2B by flow cytometry using AnxV-FITC/7-AAD.

FIG. 14 shows that AnxA5 and AnxA13 inhibit pro-inflammatory cytokine secretion of BMDCs upon TLR stimulation. FIG. 14A Scheme of AnxA1, AnxA5 and AnxA13. The N-terminal domain is unique for each annexin family member and depicted in white. The highly conserved core domain is shown in grey. (FIGS. 14B-14D) GM-CSF-differentiated BMDCs from $Tlr4^{-/-}$ mice were incubated with the indicated concentrations of recombinant protein. 6-8 h later, cells were stimulated with 40 nM CpG o/n. TNF-α (FIG. 14B), IL-12 (FIG. 14C) or IL-6 (FIG. 14D) concentrations in the supernatants were determined by ELISA. Data are mean±SEM of three independent experiments. FIGS. 14E-F GM-CSF-differentiated BMDCs from $Tlr4^{-/-}$ mice were incubated with the indicated ratio of aJ or aS2. 4-6 h later, cells were stimulated with 40 nM CpG o/n. TNF-α concentrations in the supernatants were determined by ELISA. Data are mean±SEM of four independent experiments. ((FIGS. 14G-H) Flt3L-differentiated BMDCs from $Tlr4^{-/-}$ mice were incubated with the indicated concentrations of recombinant protein. 6-8 h later, cells were stimulated with 40 nM CpG o/n. TNF-α (FIG. 14G) or IL-10 (FIG. 14H) concentrations in the supernatants were determined by ELISA. Data are mean±SEM of two independent experiments.

FIG. 15 shows that AnxA5 and AnxA13 specifically downregulate the expression of co-stimulatory molecules on BMDC. (FIGS. 15A-G) GM-CSF-differentiated BMDCs from $Tlr4^{-/-}$ mice were incubated with 500 nM of the indicated recombinant protein. 6-8 h later, cells were stimulated with 20 nM CpG. After 2 d, cells were stained with antibodies against MHC I (FIG. 15A), MHC II (FIG. 15B), CD40 (FIG. 15C), CD80 (FIG. 15D), CD86 (FIG. 15E), PD-L1 (FIG. 15F), and PD-L2 (FIG. 15G). Data points represent MFI of individual mice and the group mean. FIG. 15H Quantification of cell viability of BMDCs of mouse 1 used in (FIGS. 15A-G) by flow cytometry using AnxV-FITC/7-AAD.

FIG. 16 shows that FPR family members are not involved in recognition of AnxA5 and AnxA13 on BMDCs. FIGS. 16A-C Immunoblot analysis of MAPK activation of BMDCs after incubation with 500 nM of recombinant AnxA5 (FIG. 16A), AnxA13 (FIG. 16B) or the AnxA1 core domain (FIG. 16C) for the indicated time points. Lysates of CpG- and LPS-stimulated BMDCs from $Tkr4^{-/-}$ and WT mice, respectively, served as positive controls. Data are representative of three independent experiments. FIG. 16D GM-CSF-differentiated BMDCs from $Tlr4^{-/-}$ mice were incubated with the indicated concentrations of recombinant protein in the presence or absence of the FPR antagonist Boc-2 or apoptotic Jurkat T-cells (aJ), respectively. 6-8 h later, cells were stimulated with 40 nM CpG o/n. IL-12 concentrations in the supernatants were determined by ELISA. Data are mean±SEM of three independent experiments.

Figure 17A:
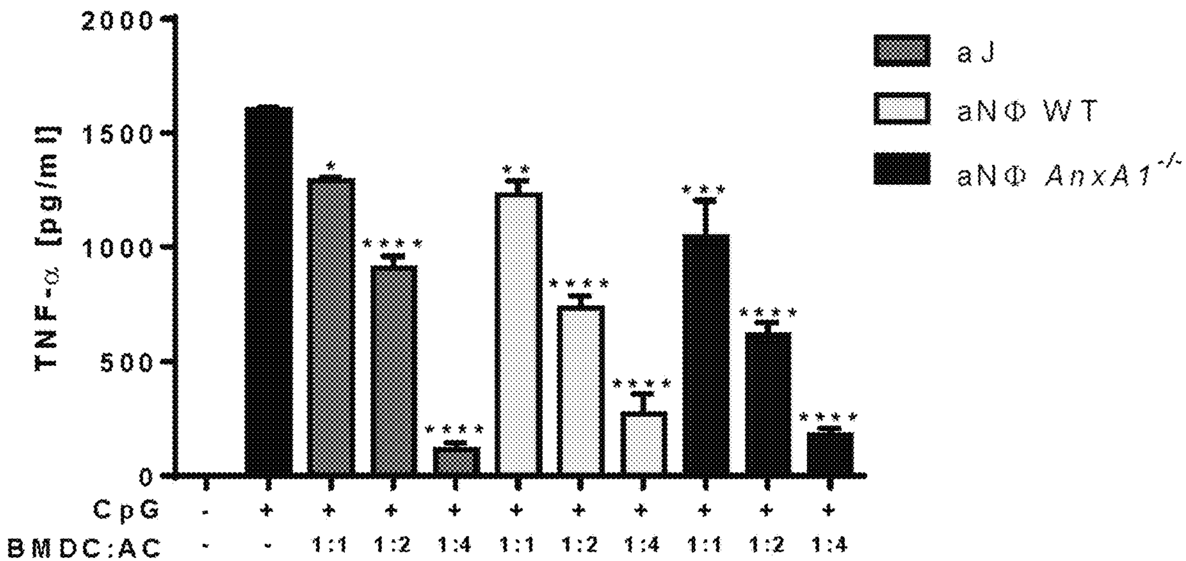
Figure 17B:
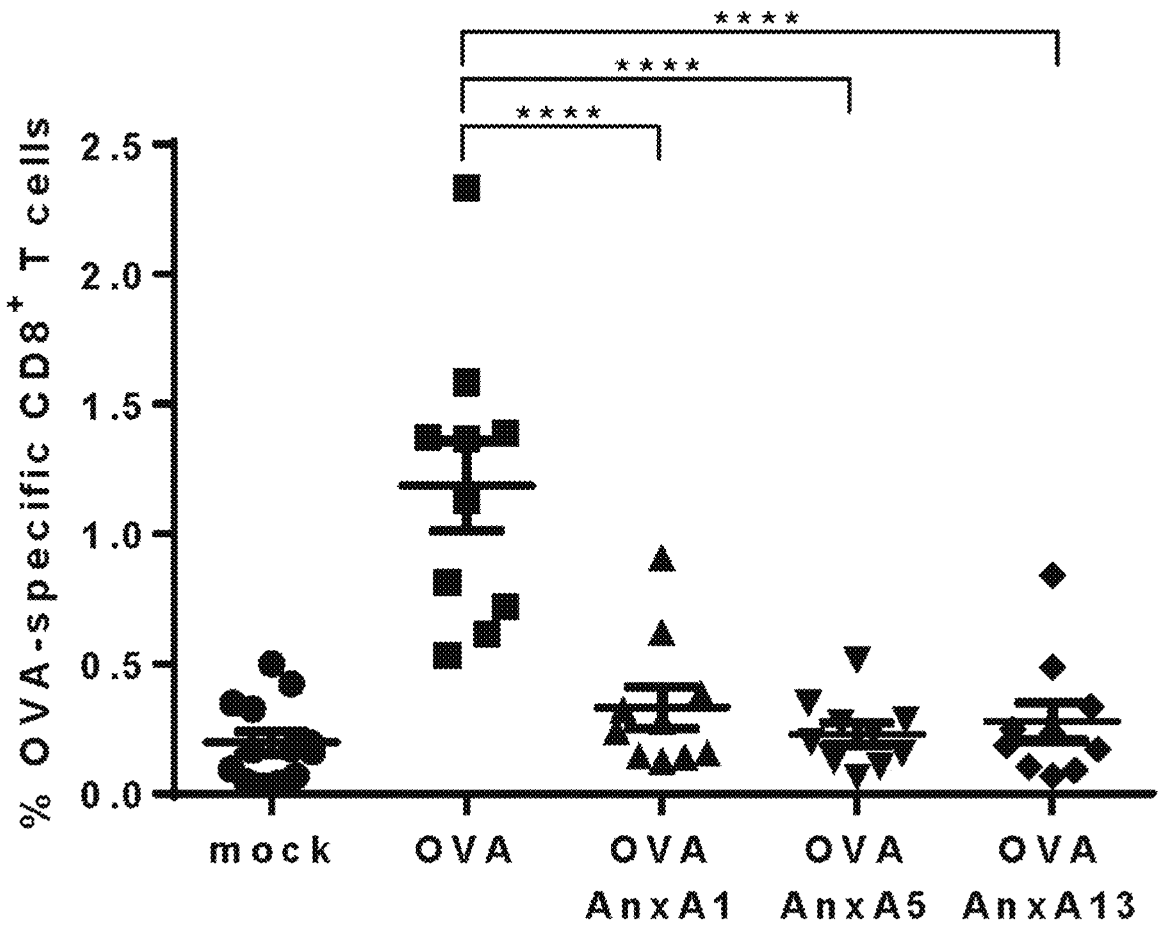

FIG. 17 shows that AnxA5 and AnxA13 suppress the induction of $CD8^+$ T cell immune responses in vivo. FIG. 17A GM-CSF-differentiated BMDCs from WT mice were incubated with the indicated ratio of apoptotic Jurkat T-cells (aJ) or apoptotic neutrophils (NΦ, d1). 4 h later, cells were stimulated with 1 ng/ml LPS o/n. TNF-α concentrations in the supernatants were determined by ELISA. Data are mean±SEM of three independent experiments. FIG. 17B Apoptotic mOVA-expressing S2 cells (aS2 mOVA) together with apoptotic stably transfected S2 cells (aS2 AnxA1, aS2 AnxA5, aS2 AnxA13) were injected i.v. into mice. Mice injected with mock-transfected aS2 cells served as a negative control. After 8 days, the induction of OVA-specific $CD8^+$ T cells in lymph nodes was analyzed by flow cytometry. Errors bars represent the mean±the SEM.

Figure 18:
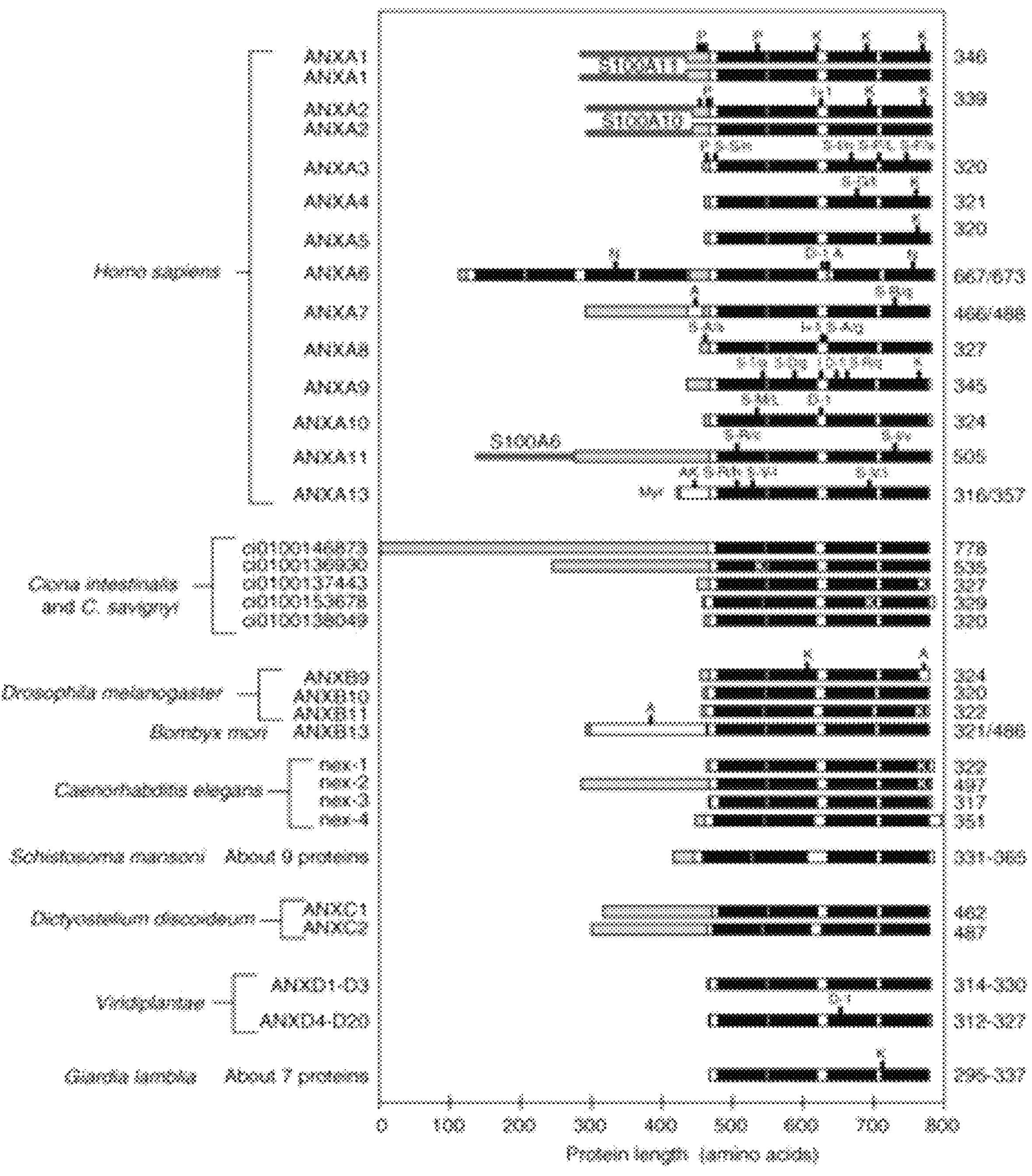

FIG. 18 shows the domain structures of representative annexin proteins. Orthologs of the 12 human annexins shown in other vertebrates have the same structures, with strict conservation of the four repeats in the core region (black) and variation in length and sequence in the amino-terminal regions (shaded). Human ANXA1 and ANXA2 are shown as dimers, with the member of the S100 protein family that they interact with. Domain structures for other model organisms are derived from public data made available by the relevant genome-sequencing projects. Features: S100Ax, sites for attachment of the indicated member of the S100 family of calcium-binding proteins; P, known phosphorylation sites; K, KGD synapomorphy (a conserved, inherited characteristic of proteins); I, codon insertions (+x denotes the number of codons inserted); S-A/b, nonsynonymous coding polymorphisms (SNPs) with the amino acid in the major variant (A) and that in the minor variant (b); N, putative nucleotide-binding sites; D, codon deletions (−x denotes the number of codons deleted); A, alternatively spliced exons; Myr, myristoylation. The total length of each protein is indicated on the right. Taken from Moss and Morgan. The annexins. Genome Biol. 2004; 5(4): 219.

FIG. 19 shows the accession numbers in FASTA format and an alignment of the protein sequences of human and murine annexins A1, A5 and A13. The conserved sequence of the core domain of the annexins is boxed. An * (asterisk) indicates positions which have a single, fully conserved residue. A: (colon) indicates conservation between groups of strongly similar properties. A . (period) indicates conservation between groups of weakly similar properties.

SEQ ID Nos. 1 to 3 and 6 to 8 show the sequences of the human annexin core domains of annexin 1, 5, and 13, respectively, as used in the context of the present invention.

SEQ ID Nos. 4 and 5 show peptide sequences as used in the context of the present invention.

EXAMPLES

Example I

Generation of Antibody mAx550 Against Annexin on Apoptotic Cells.

Annexin A1 knockout mice (B&K Universal) were 5 times immunized i.p. with $5\times10^5$ apoptotic murine neutrophils. Hybridomas were generated from spleens of immunized mice by polyethylene glycol (PEG 1500, Sigma)-induced fusion with the mouse plasmacytoma line Ag8. Hybridomas were subcloned, and supernatants analyzed for binding to immobilized murine Annexin A1 in ELISA. Positive clone mAx550 was further subcloned and analyzed for binding to human and murine annexin A1 in Western blot and flow cytometry.

Generation of Antibodies Against Several Annexins.

Annexin A1 knockout mice (B&K Universal) were immunized with 50 μg recombinant murine annexin A5 in complete Freund's adjuvants. Subsequently, mice were boosted with 50 μg recombinant murine annexin A13 in incomplete Freund's adjuvants, followed by 4 boosts with recombinant murine annexin A5 and A13 in an alternating fashion. Hybridomas were generated from spleens of immunized mice by polyethylene glycol (PEG 1500, Sigma)-induced fusion with the mouse plasmacytoma line Ag8. Hybridomas were subcloned, and supernatants analyzed for binding to immobilized murine annexin A1, annexin A5, and annexin A13 in ELISA. Positive clones were further subcloned and analyzed for binding to human and murine annexins in flow cytometry.

Mice.

TLR4−/− deficient mice were kindly provided by S. Akira, S. Uemattsu and L. Gissmann. C57BL/6 mice were purchased from the Jackson Laboratory. Annexin A1 knockout mice were purchased from B&K Universal. All mice were maintained in specific-pathogen-free facilities.

Preparation of Recombinant Proteins.

Recombinant proteins were expressed in the *Escherichia coli* BL21(DE3)pLysS strain (Promega, Mannheim, Germany) from the pET41a vector (Novagen, Darmstadt, Germany). PCR products of annexin A1 or serpin B8 were cloned into pET41a harboring a C-terminal FLAG_tag, a PreScission protease cleavage site and a Protein A_tag. Bacterial lysates (10,000×g, 4° C. for 40 min) were loaded onto pre-equilibrated IgG Sepharose 6 Fast Flow beads (GE Healthcare). Removal of LPS was achieved by washing with TBS containing 0.1% Triton X-114 (Sigma). Triton X_114 was removed by washing with TBS containing 0.05% Tween-20 (Gerbu). After cleavage of the fusion protein with PreScission protease (GE Healthcare) and PreScission protease removal, the recombinant protein was dialysed against PBS. LPS content in all annexin A1 preparations was determined to be below 5 EU/mg using the Limulus Amoebocyte Lysate Assay (Lonza) according to the manufacturers' instructions.

Cells and Cell Lines.

Murine neutrophils were prepared by magnetic cell isolation (Miltenyi) according to the manufacturer's instructions. BMDCs were prepared from $TLR4^{-/-}$ mice between 6-12 wk of age as described. In brief, BM cells were flushed from tibias and femurs, and RBCs were lysed by brief exposure to 0.168 M $NH_4Cl$. Cells were washed twice with RPMI 1640. For differentiation of BM precursors to BMDCs using recombinant murine GM-CSF, $1\times10^6$ cells were seeded at a density of $1\times10^6$ cells/ml in RPMI 1640 complete medium (10% FCS, 10 U/ml penicillin/streptomycin, 300 mg/l L-glutamine, 20 ng/ml GM-CSF (Immunotools)) in a 24-well plate. After 2 days the medium was replaced by fresh medium. After 4 d, half of the medium was removed and replaced by fresh medium. Experiments were conducted 7-8 d after differentiation.

Preparation of Apoptotic Cells.

For induction of apoptosis, RMA cells were irradiated with 75 $mJ/cm^2$ UV-C in a Stratalinker 1800 (Stratagene) and used after 2-3 h of incubation. Apoptotic human neutrophils were obtained by continuous in vitro culture for 1-3 days.

Coculture of DC, Annexin A1, Apoptotic Cells and T Cells $1\times10^5$ BMDCs were incubated with beads (0.2-2 Mio/well) or with apoptotic RMA cells ($5\times10^5$ cells/well) or apoptotic neutrophils ($1\text{-}2\times10^5$ cells) for 4-6 h. BMDCs were subsequently stimulated with CpG 1668 at the indicated concentrations. Cytokine concentrations in the supernatants were analyzed 12-16 h after CpG stimulation by ELISA. 24 h after stimulation, CFSE-labeled OT1 and OT2 T cells (each at a concentration of 0.5 Mio per well) were added to the cultures. For estimating T cell proliferation, CFSE-dilution of transferred OT1 and OT2 T cells was analyzed by flow cytometry.

In Vivo Experiments.

OT1 cells alone or a mixture of CFSE-labeled OT1 and OT2 cells were injected into mice (1 Mio each, i.v.). After 1 d, 20 Mio OVA-annexin- or OVA-control-beads/mouse were injected i.v. 7-13 days later, proliferation and expression of FoxP3 of transferred OT1 and OT2 cells were analyzed by flow cytometry. In other experiments, a mixture of 375.000 apoptotic OVA-expressing Schneidercells and 750.000 apoptotic annexin-expressing Schneidercells were injected i.v. instead of beads. 12 days later mice were challenged by injection of 50 μg OVA (Invivogen) in incomplete Freund's adjuvant (Sigma) i.p. 5-6 days later, immune reactivity of splenic T cells of immunized mice was measured against OVA-derived peptides (SIIINFEKL (SEQ ID NO. 4), ISQAVHAAHAEINEAGR, 10 nM (SEQ ID NO. 5)) in ELISpot assays (BD Bioscience). To this purpose, 1.5 Mio splenocytes were stimulated with respective peptides in ELISpot plates (Corning Costar) overnight. Interferon γ-Spots were detected according to manufacturers' instructions. For in vitro restimulation assays, 2.5 Mio splenocytes in 96-well round bottom plates were stimulated with the respective peptides for 3 days. Interferon γ-secretion of cells was detected in supernatants by ELISA (BD Biosciences).

Generation of Annexin-Ova Beads.

$5\times10^9$ fluorescent latex beads (life technology) were incubated with a total of 1.25 ovalbumin (Invitrogen) and 5 μg anti-FLAG antibody (M2, Sigma) in 500 μl phosphate buffered saline (PBS) for 12 h at 4° C. on a revolving rotor. Subsequently, beads were washed 3× with PBS and resuspended in 500 μl PBS. For coupling to annexin or control protein, $2.5\times10^8$ beads were incubated with 6.25 μg recombinant annexin A1 core domain or control protein (PRMT6, Sino Biologicals) in a total volume of 100 μl PBS for 12 h at 4° C. on a revolving rotor. Subsequently, beads were washed 2× with PBS and resuspended in 250 μl PBS.

Measuring the Affinity of the Binding Between Annexin and LRP-1.

For measuring the affinity of the binding of LRP-1 to different annexins (annexin A1, A5, and A13) the device A100 (ATTANA) was used. LRP-1 was immobilized on an LNB carboxychip according to the manufacturers' instructions. In order to achieve this, first, the chip was activated with EDC/SulfoNHS according to the manufacturers' instructions, and then purified LRP1 (5-15 μg/ml) in a sodium acetate buffer (pH 4.0) was injected onto the chip until an increase of the frequency at 70-100 Hz was reached. Then, remaining binding spots on the chip were saturated using two injections of ethanolamine, and the chip was buffered in PBS. For the incubation with the different annexins, they were prepared in six different concentrations in PBS with 2 mM calcium, and measured in triplicates. After each Anx-injection the chip was regenerated with 5 mM EDTA/PBS and 3M NaCl before the next Anx-injection.

Annexin Binding Measurement for Different Receptors by ELISA.

To test for binding to annexins, putative receptor molecules, fragments thereof or fusion proteins (e.g. LRP-11, single LRP-1 domains or Dectin-1 Fc protein) are immobilized on an ELISA plate at 10 μg/ml in coating buffer (Carbonate-Bicarbonate—1.5 g $Na_2$ $CO_3$; 2.93 g NaH $CO_3$; Distilled water, 1 liter, pH to 9.6). After washing (3×PBS Tween 0.01%) and blocking (1% Casein in PBS), different concentrations of recombinant annexins are incubated in the wells for 2 h, followed by 5 wash steps (PBS-Tween 0.05%). Bound annexins are then detected by suitable secondary reagents (e.g. horse radish peroxidase (HRP) labeled secondary antibodies or biotin-labeled secondary antibodies plus streptavidin-labeled HRP) to the recombinant annexin-proteins and measured by reactivity with a suitable substrate (e.g. OPD) in an ELISA plate reader. The assay can also be performed by immobilizing different annexins on a plate and probing with recombinant receptor molecules, fragments thereof or fusion proteins (e.g. LRP-1, single LRP-1 domains or Dectin-1 Fc protein).

Binding Affinity Measurements for Annexin—Dectin 1 by Surface Plasmon Resonance.

Surface plasmon resonance (SPR) is a valuable tool for analyzing receptor ligand interactions in real time and for providing insights into the affinity and kinetics of binding. SPR is a technique for measuring the association and dissociation kinetics of ligand, termed analyte, with a receptor. The analyte or the receptor can be immobilized on a sensor chip which bears a gold film. The association of the analyte and receptor with one or the other, depending which one is immobilized, induces a change in the refractive index of the layer in contact with the gold film. This is measured as a change in the refractive index at the surface layer and is recorded as the SPR signal in resonance units (RU). For the preparation of Dectin-1-coated surfaces, Dectin-1 was immobilized at a flow rate of 10 μl/min. The CMS chip was activated by injection of a mixture of N-ethyl-N'-(diethylaminopropyl)-carbodiimide (EDC) and N-hydroxysuccinimide (NHS) for 10 minutes and functionalized by injecting 100 μg/mL and 10 μg/mL Dectin-1 in acetate buffer pH 5.5 for 7 minutes. The remaining activated carboxyl groups were then capped by injection of 1 M ethanolamine for 10 minutes. Control flow cells were treated with EDC/NHS followed by ethanolamine as described. Concentration gradients of the different annexins were injected over the Dectin-1-functionalized surfaces at 10 μL/min, allowing 60 seconds for contact and 300 seconds for dissociation times, followed by regeneration using 100 mM methyl-α-D-mannopyranoside at 30 μL/min for 30 seconds. Experimental data were analyzed using Biacore S20 T100 Evaluation Software. Kinetic analyses based on a 1:1 interaction model for the annexin-dectin-1 complexes interaction were performed using Scrubber2 (BioLogic Software, Campbell, Australia).

Example II

Mice. TLR4$^{-/-}$ deficient mice were kindly provided by S. Akira, S. Uemattsu and L. Gissmann. C57BL/6 mice were purchased from the Jackson Laboratory. Annexin A1 knockout mice were purchased from B&K Universal. All mice were maintained in specific-pathogen-free facilities.

Cells and cell lines, the preparation of apoptotic cells, the coculture of DCs, annexin A1, apoptotic cells, and T cells, the generation of antibody mAx550 against annexin A1 on apoptotic cells, the generation of antibodies against several annexins, the preparation of recombinant proteins, the in vivo experiments, and the generation of annexin-ova beads were performed as described above for Example I.

The Tolerogenic Effect of AnxA1 is Mediated by its Core Domain

Figure 12A:
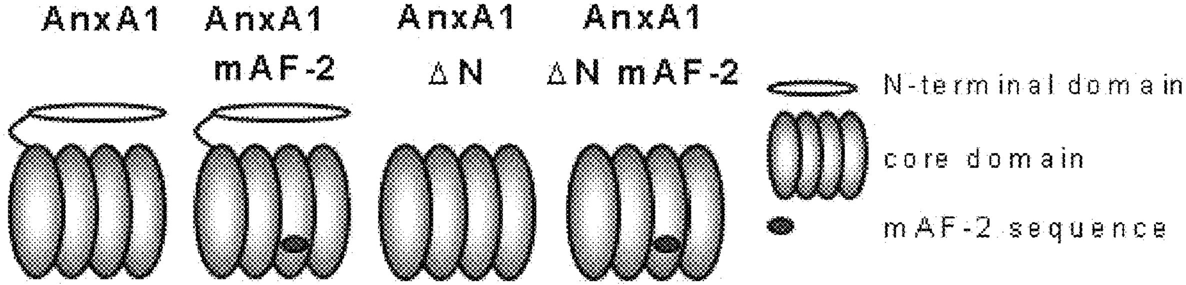
Figure 12B:
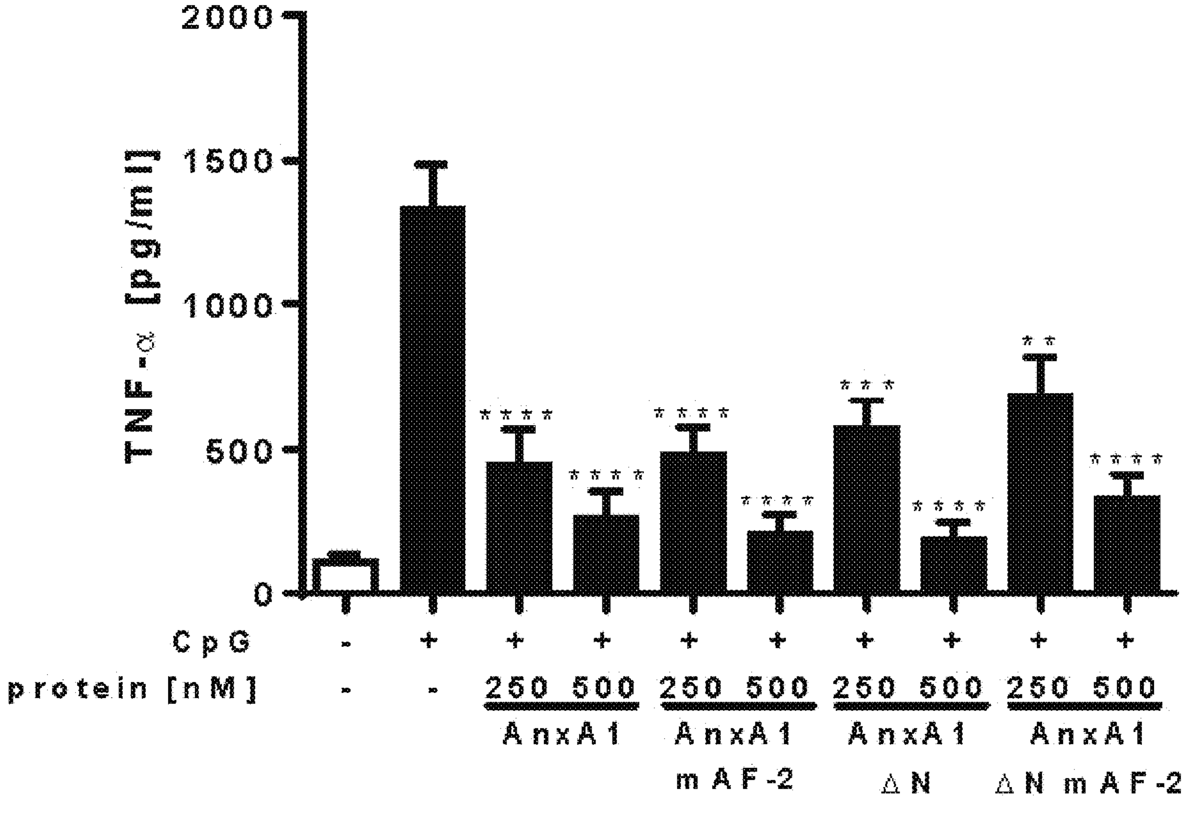
Figure 12D:
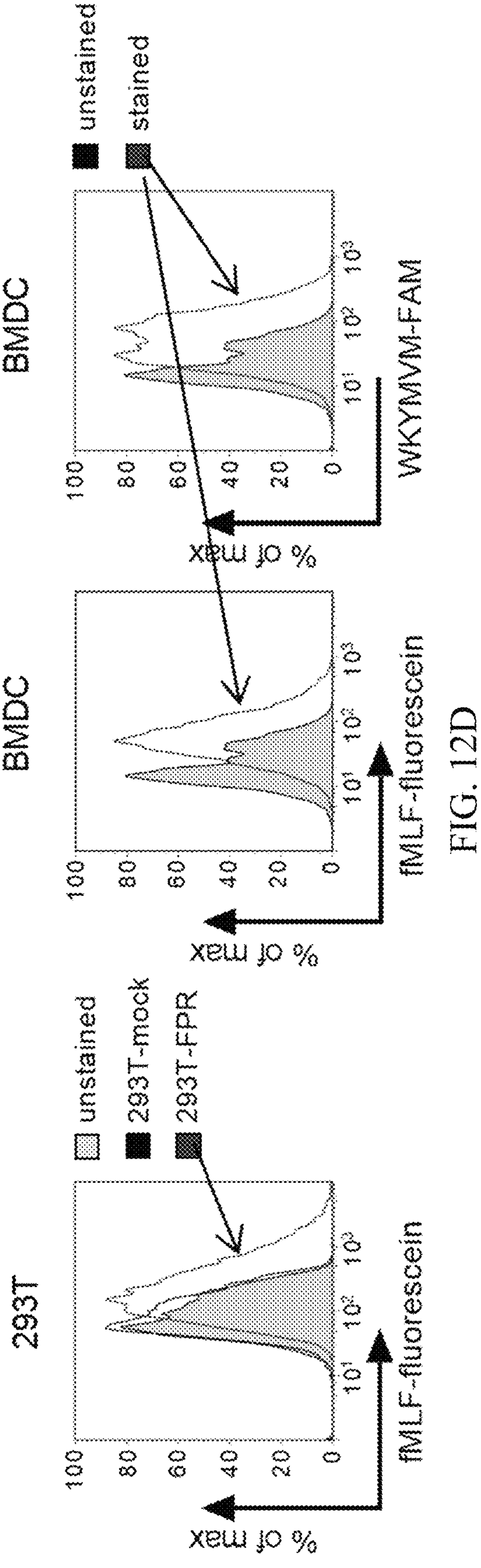
Figure 12E:
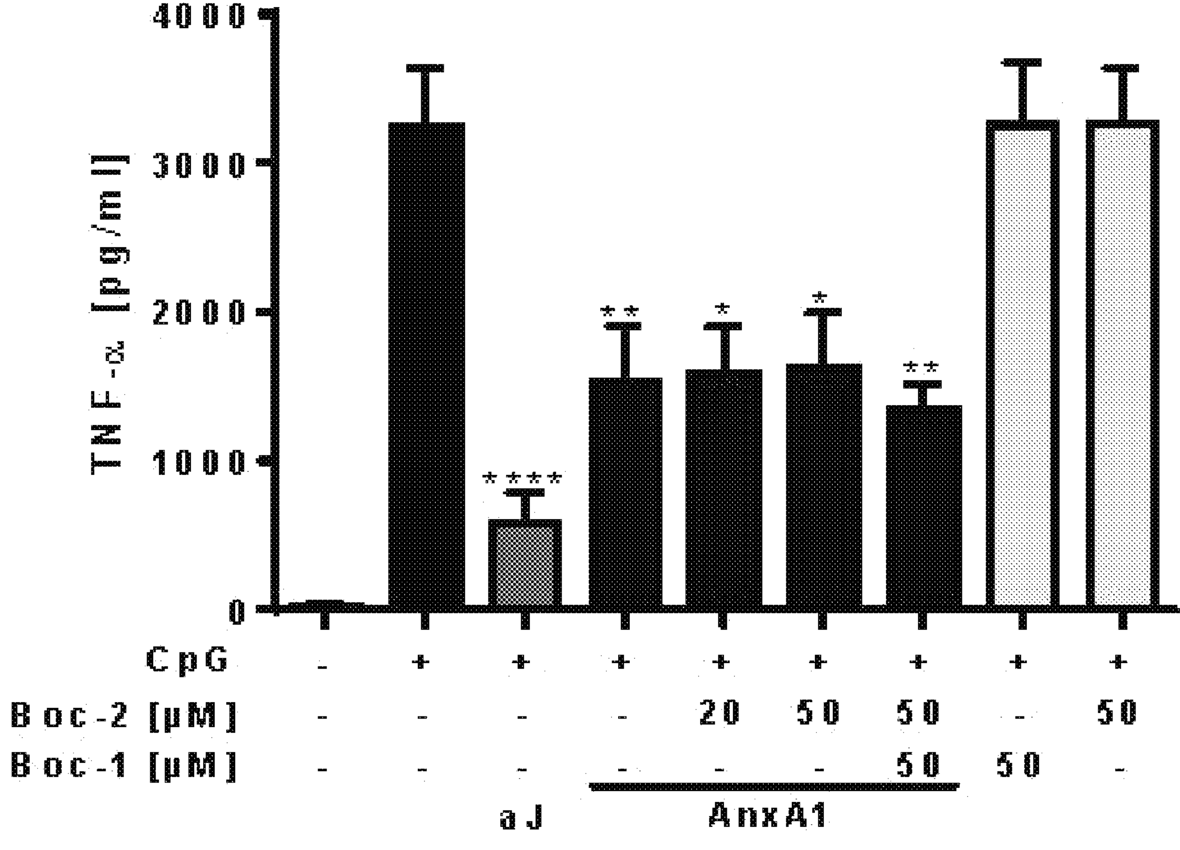
Figure 12F:
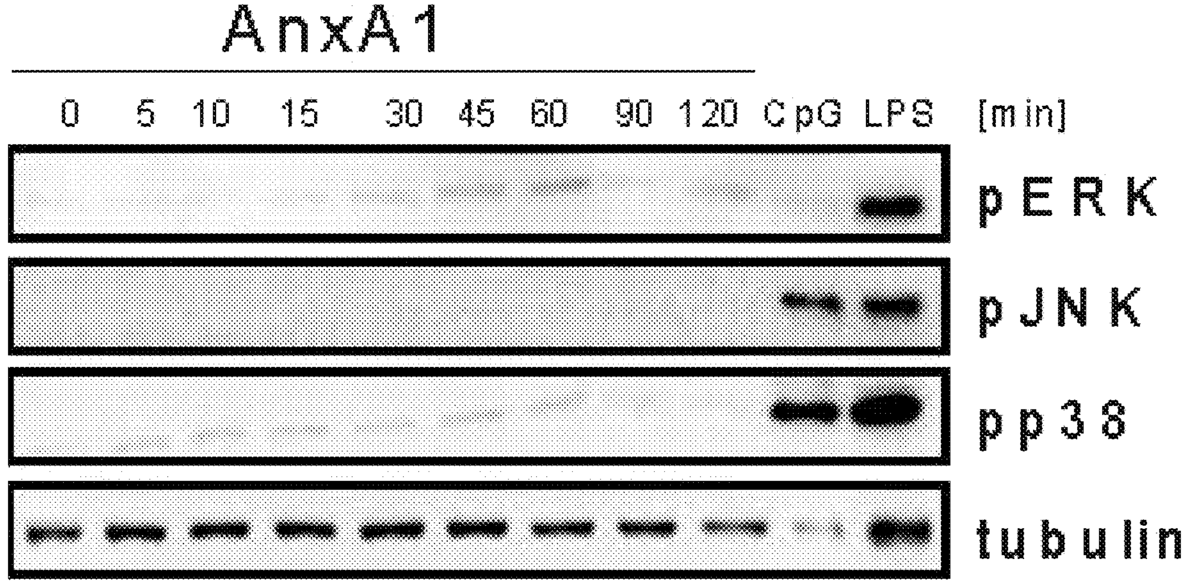
Figure 12G:
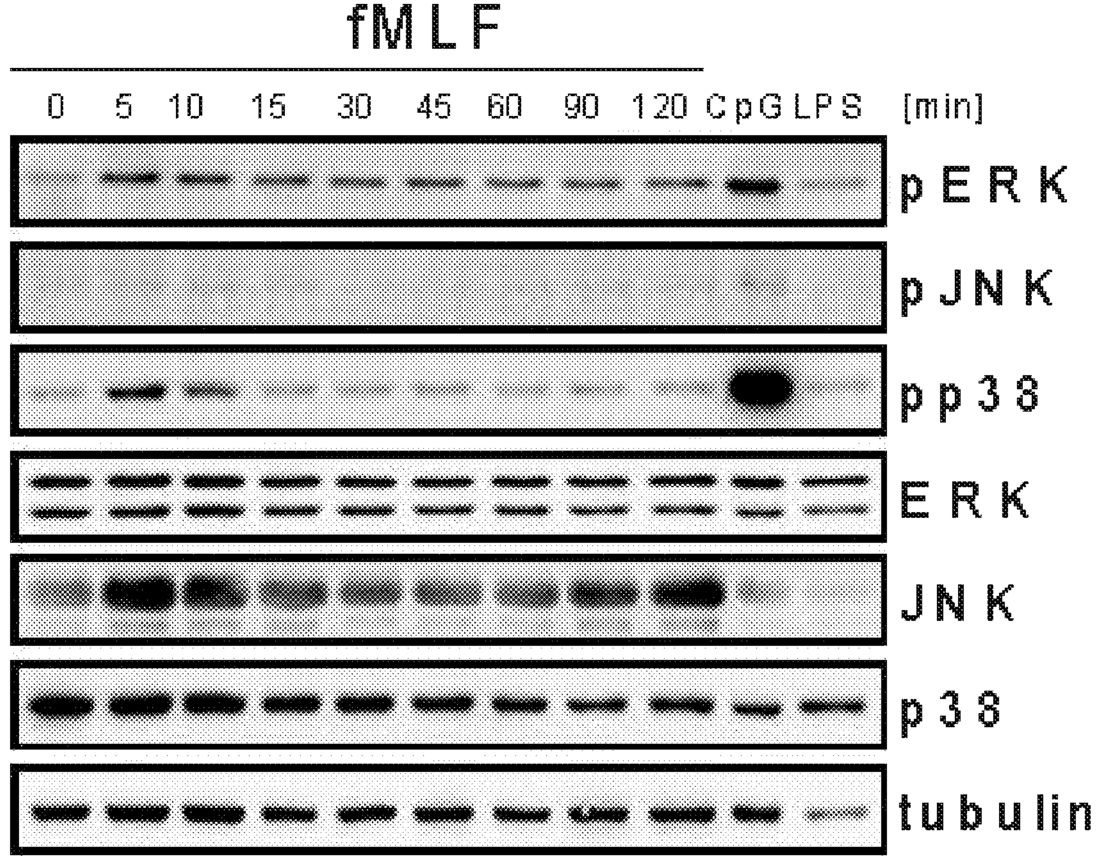

The inventors previously showed that AnxA1 on the surface of ACs negatively regulates DC activation as evidenced by low expression of co-stimulatory molecules and low pro-inflammatory cytokine secretion upon TLR stimulation (11). To investigate to which extent known anti-inflammatory sequences of AnxA1, the N-terminus as well as the AF-2 sequence contribute to this tolerogenic effect, the inventors generated recombinant full length AnxA1 and AnxA1 mutants (FIG. 12A). LPS was carefully removed during purification of recombinant proteins by addition of Triton X-114 and all in vitro experiments were performed using BMDCs from Tlr4$^{-/-}$ mice to exclude effects induced by endotoxin tolerance. In addition, a control protein, serpin 8b, purified in an identical fashion as AnxA1, was inactive in the inventors' functional assays (11). Surprisingly, neither deletion of the N-terminal domain nor mutation of the AF-2 sequence nor a combination of both affected AnxA1-induced inhibition of pro-inflammatory cytokine secretion upon stimulation with the TLR9 ligand CpG (FIG. 12B). This was not due to absence of FPR expression as FPR family members involved in AnxA1 recognition are expressed in BMDCs on the mRNA as well as on the protein level (FIG. 12C-D). To further study the involvement of FPR family members in AnxA1-induced DC tolerization, the pan-specific FPR antagonists Boc-1 and Boc-2 were used in subsequent experiments. The presence of Boc-1 and Boc-2 did not abrogate inhibition of TLR-induced TNF-α secretion by AnxA1 (FIG. 12E). In line, the prototypic FPR ligand fMLF, but not AnxA1, led to activation of MAPK (FIG. 12 F-G). In conclusion, FPR family members do not contribute to recognition of AnxA1 by BMDCs in the context of suppression of DC activation upon TLR stimulation. Instead, the AnxA1 core domain is sufficient to mediate DC tolerization, independent of the AF-2 sequence and the AnxA1 N-terminal domain.

Several Annexin Family Members Translocate to the Cell Surface Upon Induction of Apoptosis The annexin core domain is highly conserved among annexin family members and redundancy has been reported for various functions of annexins (12, 25, 28-31). Therefore, the inventors hypothesized that several annexins might act as tolerogenic signals on the surface of ACs. To test this hypothesis, the inventors first investigated whether other annexins besides AnxA1 translocate to the cell surface upon apoptosis induction. In the inventors' subsequent studies the inventors focused on AnxA5, as it is upregulated in different tissues of AnxA1$^{-/-}$ mice and might compensate for the loss of AnxA1 (32). Furthermore, the inventors also included AnxA13 in the inventors' studies as it is the founder gene of annexins (33). The surface translocation of annexins was first studied by ectopic expression of murine annexins in Schneider insect (S2) cells. Stably transfected S2 cells showed surface exposure of AnxA1, AnxA5 or AnxA13 during early apoptosis when membrane integrity was still intact (FIG. 13A). Next, the inventors induced apoptosis in the human T cell line CEM and monitored translocation of endogenous annexins. In line with the findings observed in stably transfected S2 cells, AnxA5 and AnxA13 in addition to AnxA1 translocated to the surface of apoptotic CEM cells (FIG. 13B). Of note, protein amounts of annexins in the cytosolic fraction remained almost unchanged, indicating that during apoptosis only a minor fraction of the cytosolic pool of annexins translocates to the cell surface (FIG. 13B). In summary, not only AnxA1 but also AnxA5 and AnxA13 are exposed on early ACs.

Figure 14A:
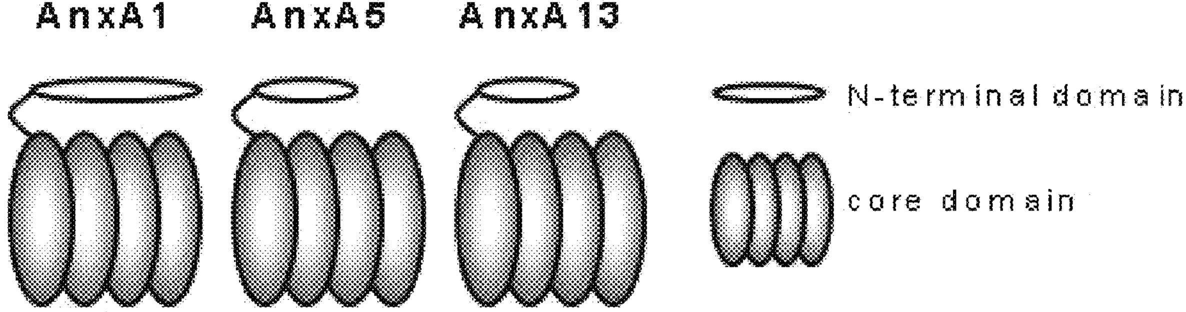
Figure 14B:
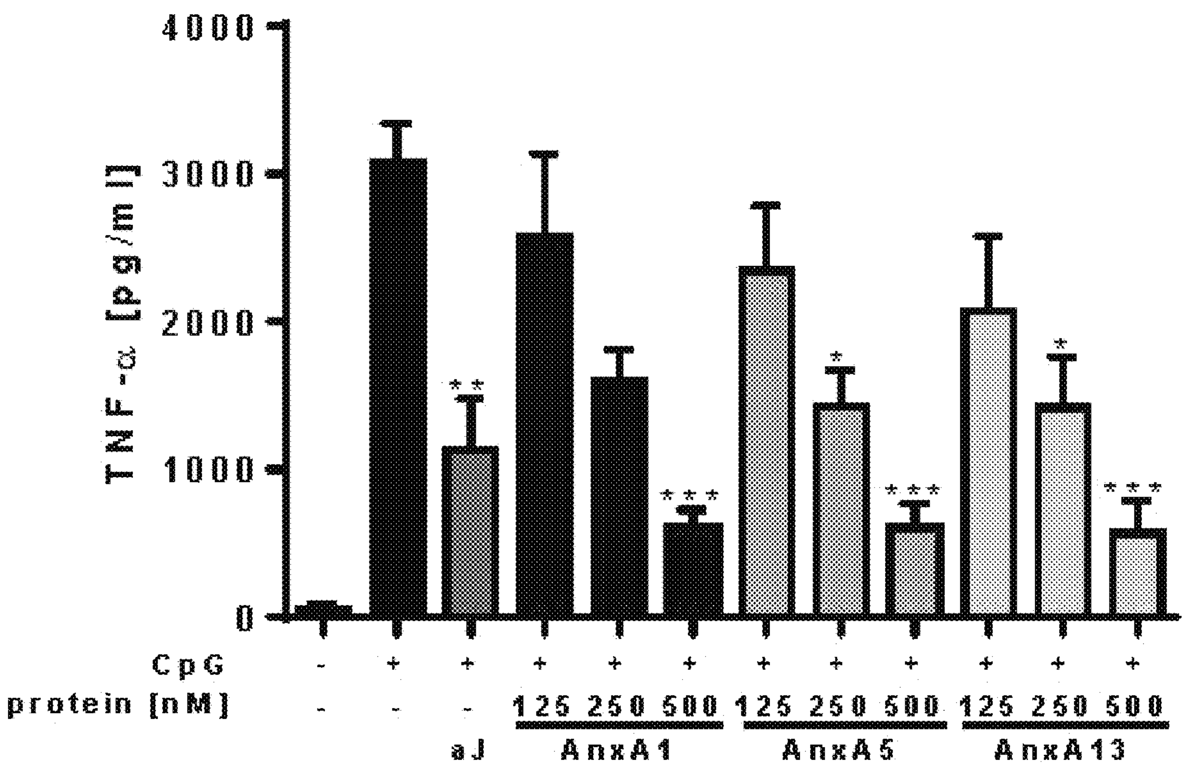
Figure 14C:
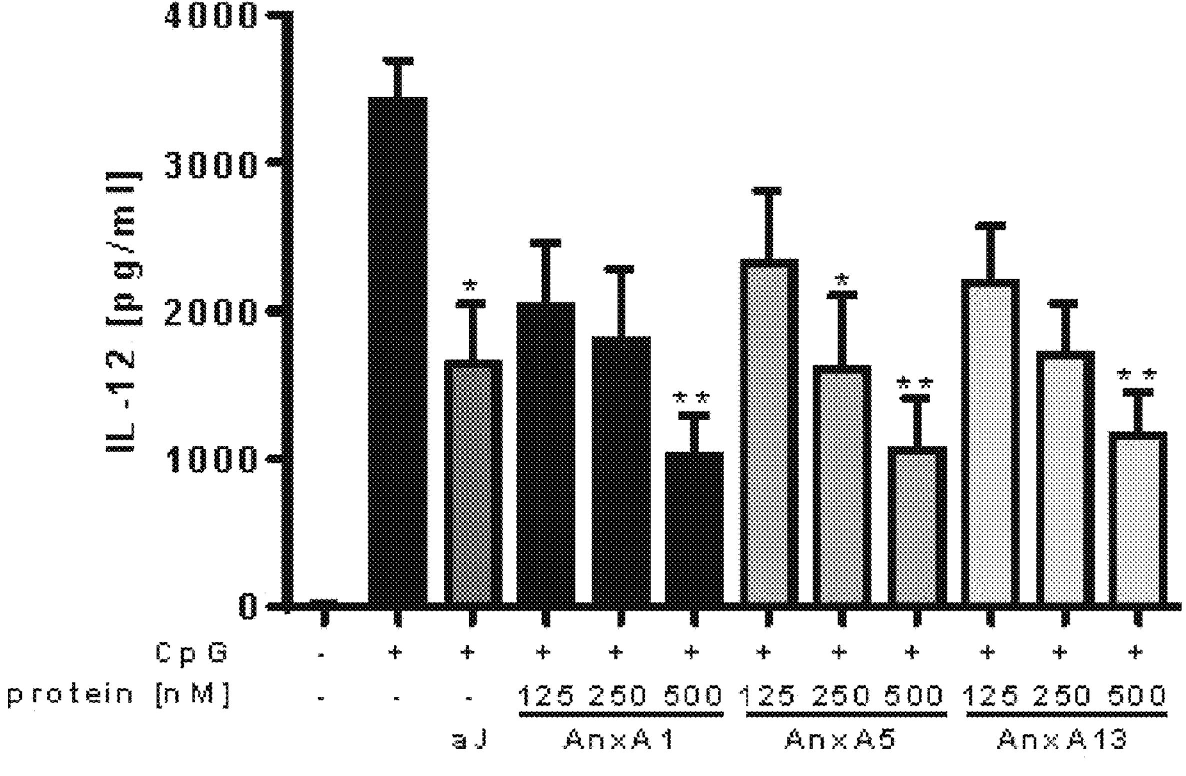
Figure 14D:
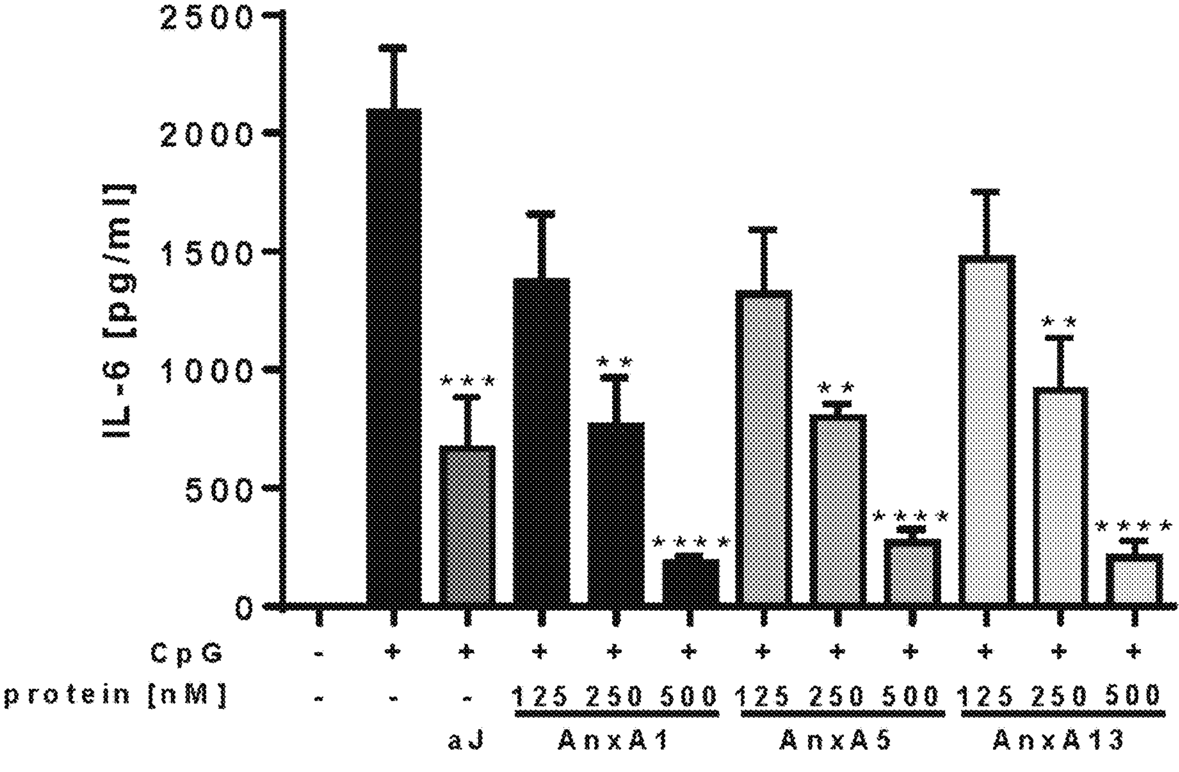
Figure 14E:
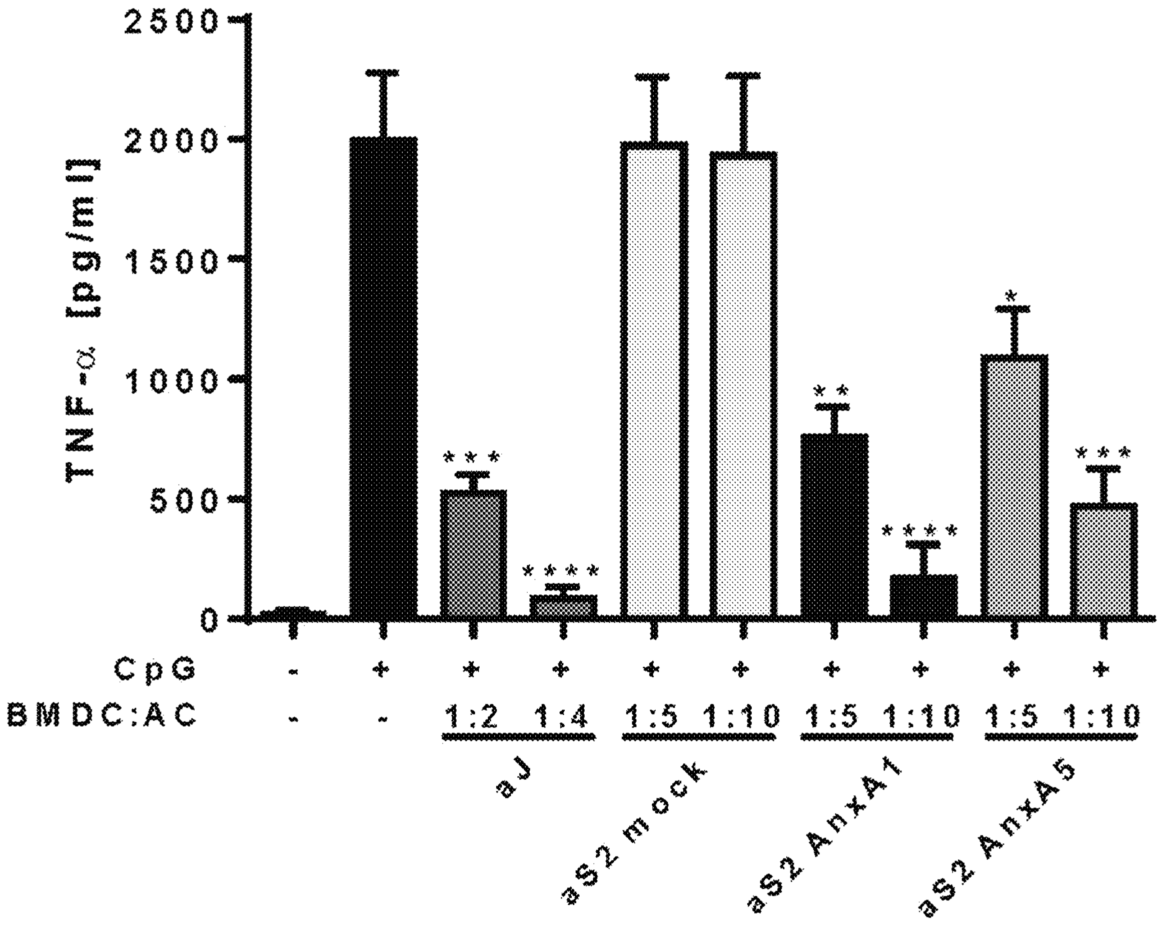
Figure 14F:
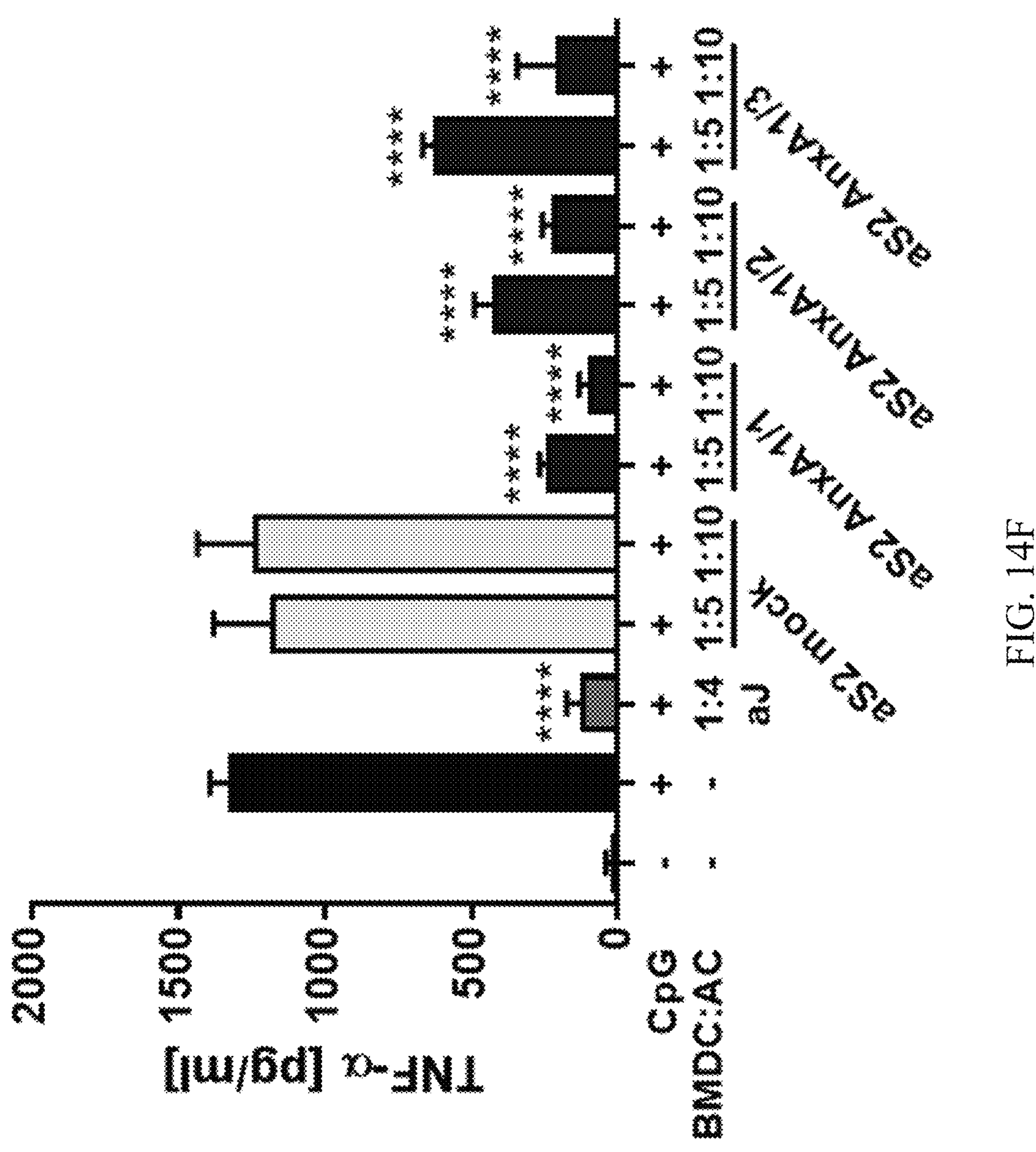
Figure 14G:
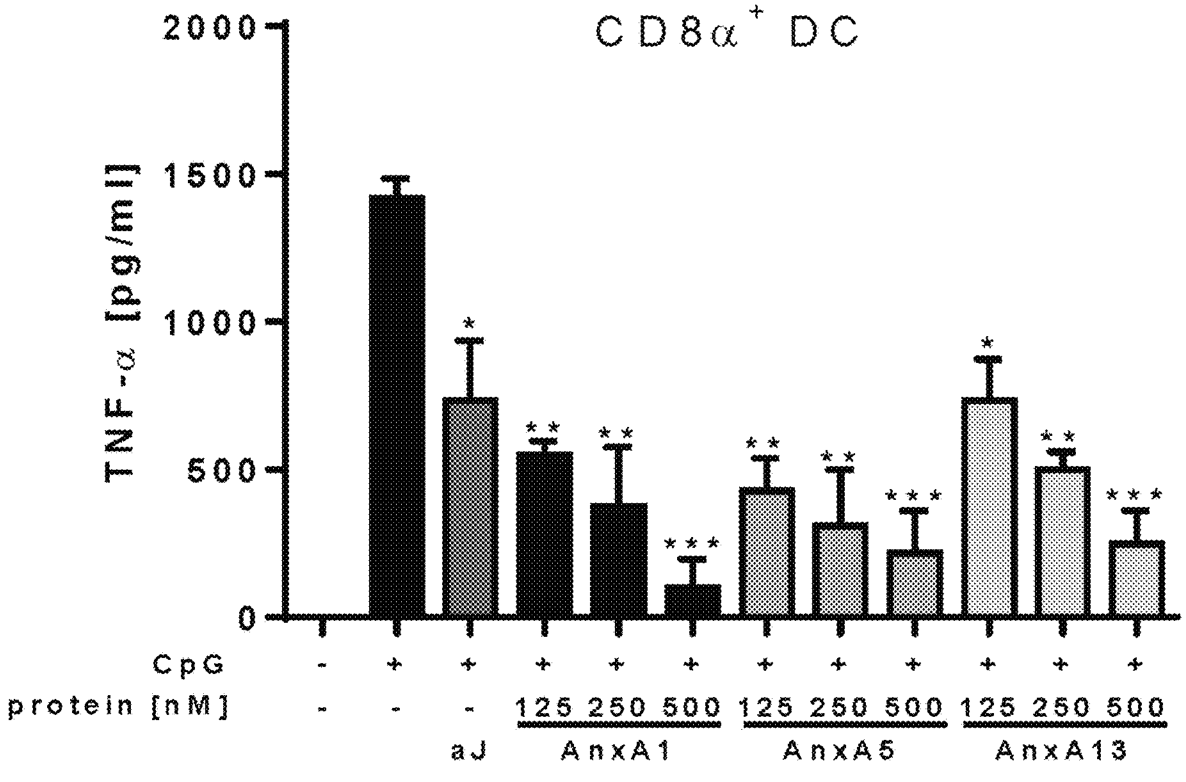
Figure 14H:
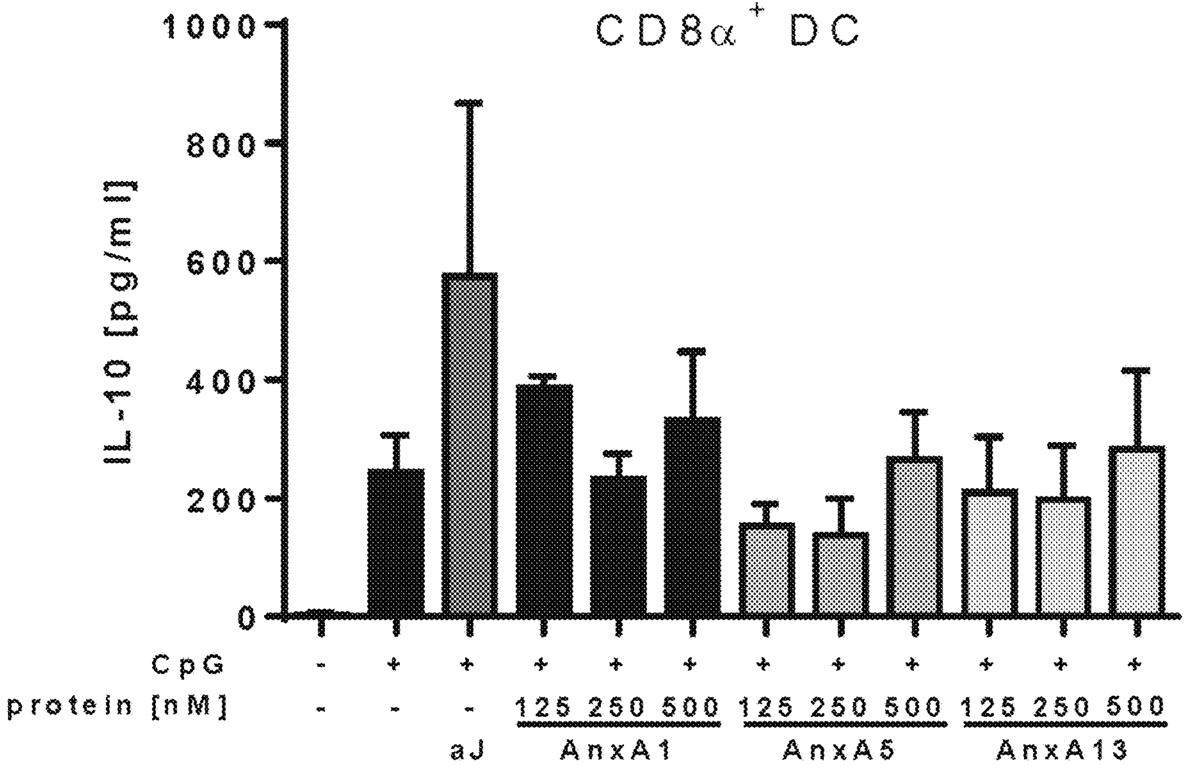

AnxA5 and AnxA13 Inhibit TLR-Induced Pro-Inflammatory Cytokine Secretion by BMDCs As AnxA5 and AnxA13 met the prerequisite to act as a tolerogenic signal, surface translocation during early apoptosis, the inventors next studied whether they also like AnxA1 regulate TLR-induced DC activation. For this, either purified recombinant proteins or stably transfected S2 cells exposing the respective annexin upon apoptosis induction, were used (FIG. 13A). Incubation of BMDCs with recombinant AnxA1, AnxA5 or AnxA13 significantly reduced the secretion of the pro-inflammatory cytokines TNF-α, IL-12 and IL-6 by TLR-stimulated BMDCs in a concentration-dependent manner (FIG. 14). Importantly, this effect was independent of altered cell viability of BMDCs. Similar to the results obtained using recombinant annexins, apoptotic S2 cells stably transfected with AnxA1 or AnxA5 reduced TLR-induced TNF-α secretion. Mock-transfected apoptotic S2 cells, in contrast, did not modulate DC activation (FIG. 3E). Flow cytometric analysis did not reveal differences in phosphatidylserine (PS) externalization, indicating that apoptosis kinetics were comparable in mock- and annexin-transfected S2 cells. The tolerogenic effect of annexins was concentration-dependent as the inhibition of TLR-induced pro-inflammatory cytokine secretion increased with the ratio of apoptotic S2 cells to BMDCs and correlated with annexin expression levels in S2 cells (FIG. 14E-F). CD8$\alpha^+$ DCs, which can be generated via differentiation of BM precursors using Flt3L in vitro, play a critical role in the presentation of self-antigens derived from ACs (34). Addition of recombinant annexins to Flt3L-derived BMDCs reduced the TLR-induced secretion of TNF-$\alpha$ in a concentration-dependent manner, while the secretion of the anti-inflammatory cytokine IL-10 was not affected (FIG. 14G-H). These effects were recapitulated with Flt3L-derived BMDCs incubated with apoptotic S2 cells expressing either AnxA1 or AnxA5. While the secretion of the pro-inflammatory cytokine TNF-$\alpha$ was reduced, annexins had no influence on the secretion of IL-10. Taken together, the inventors' data show that AnxA5 and AnxA13 inhibit the TLR-induced secretion of pro-inflammatory cytokines by DCs, including CD8$\alpha^+$ DCs, whereas the secretion of the immune-regulatory cytokine IL-10 was not affected.

Figure 15A:
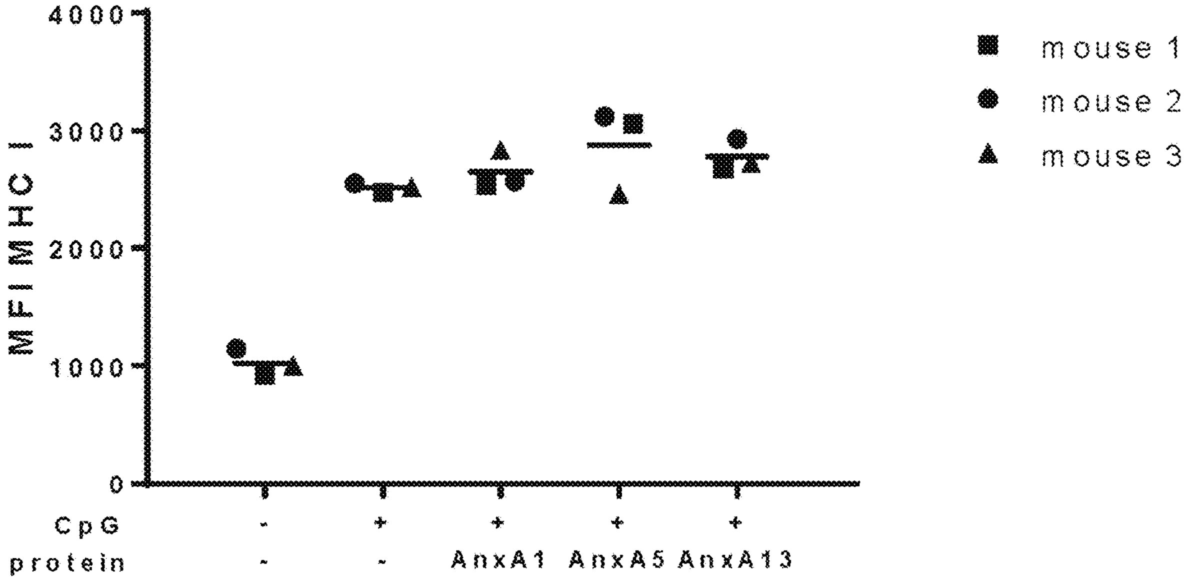
Figure 15B:
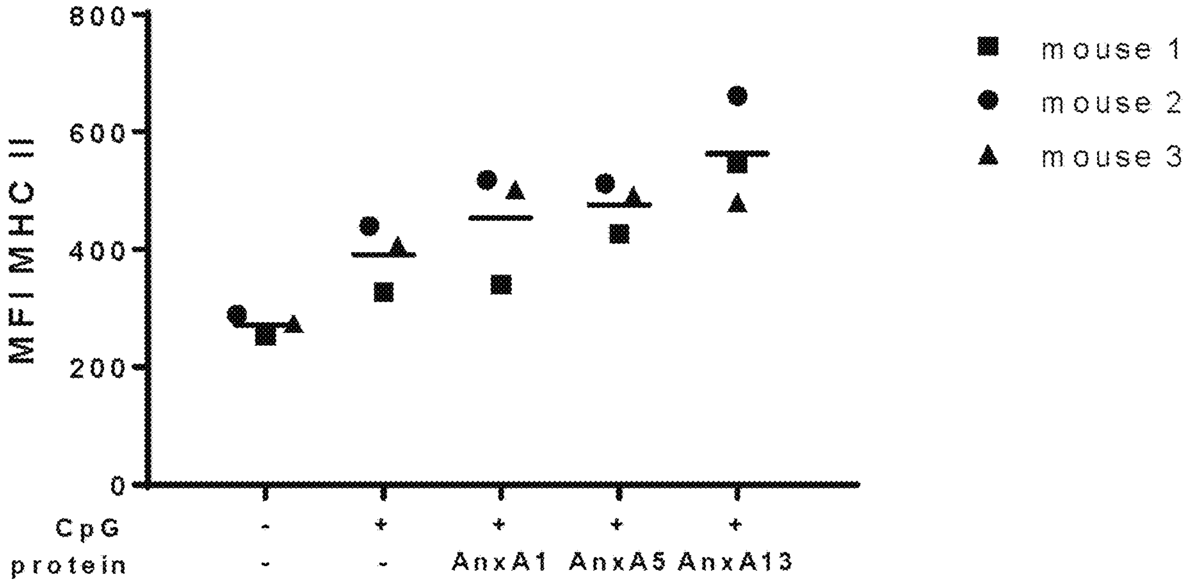
Figure 15C:
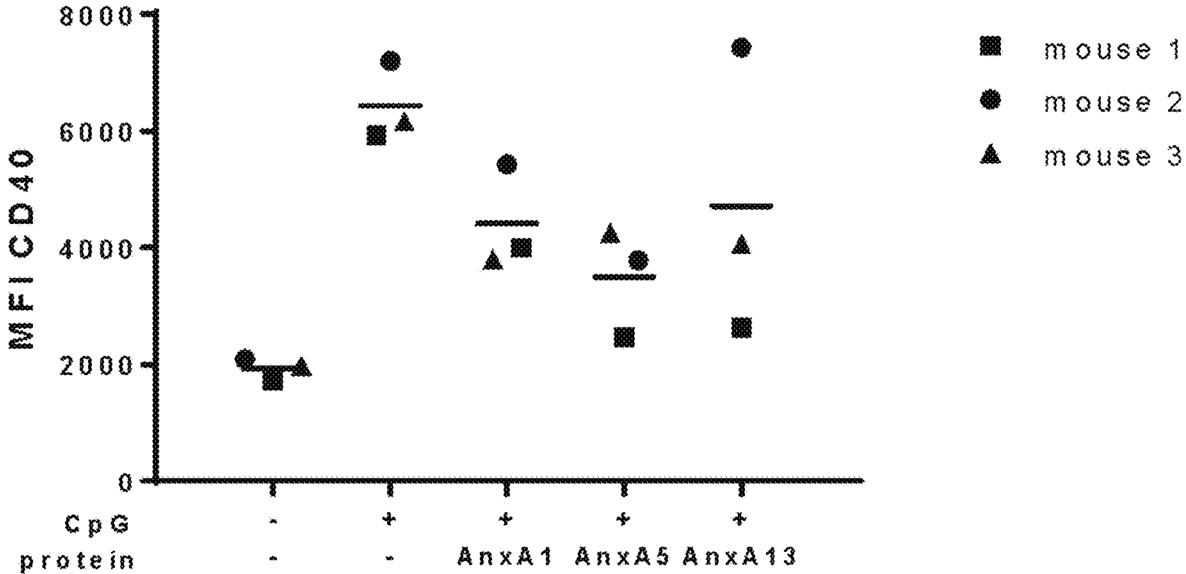
Figure 15D:
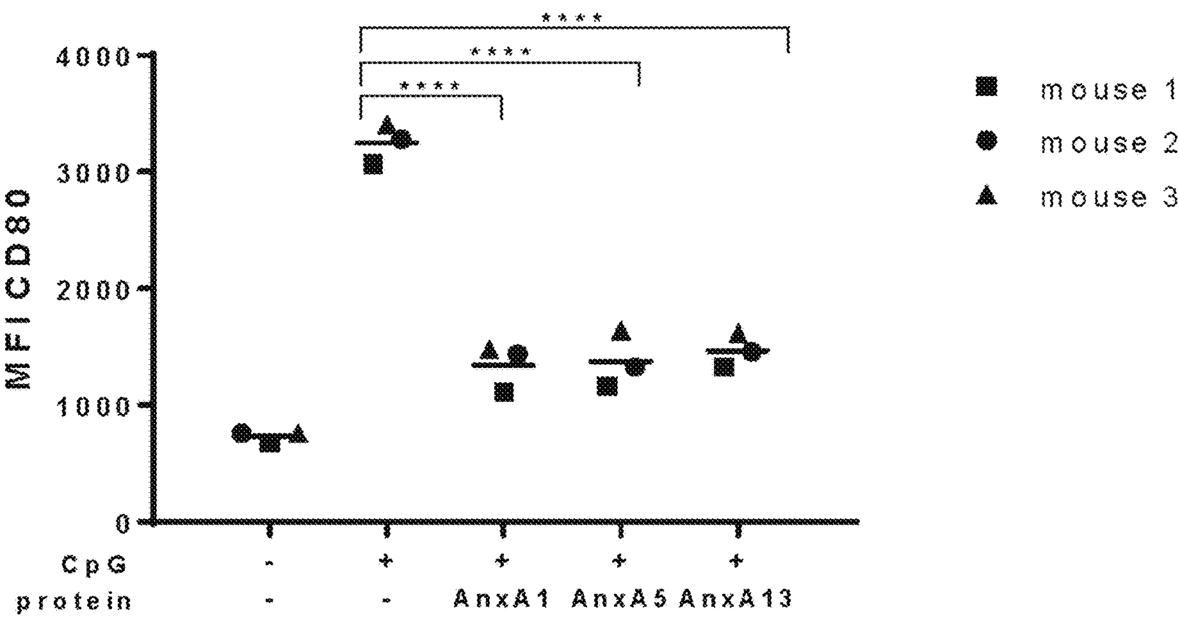
Figure 15E:
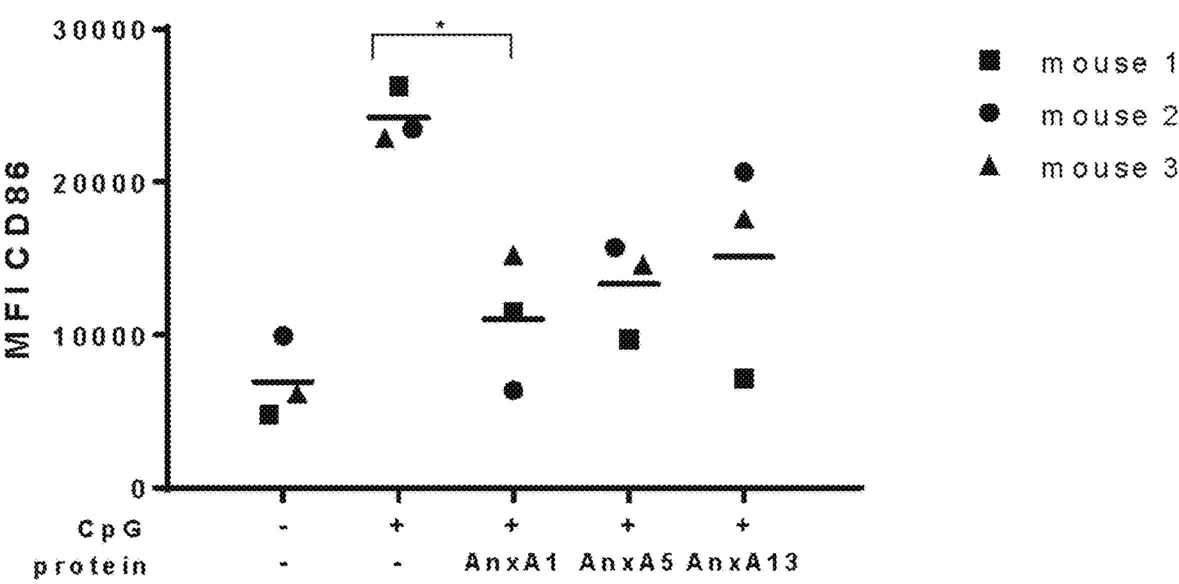
Figure 15F:
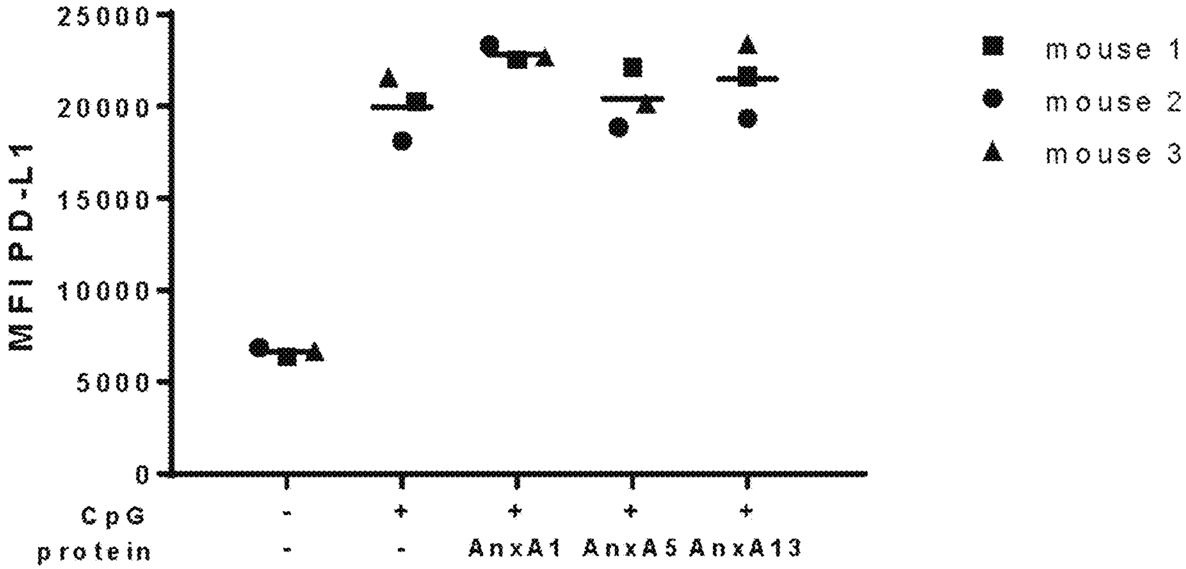
Figure 15G:
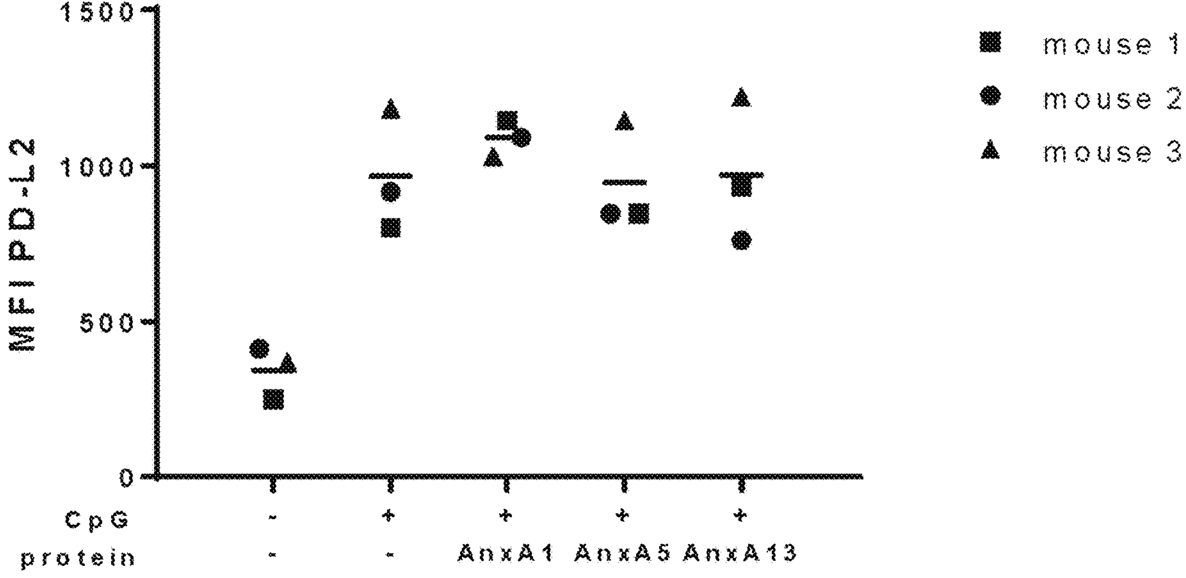
Figure 15H:
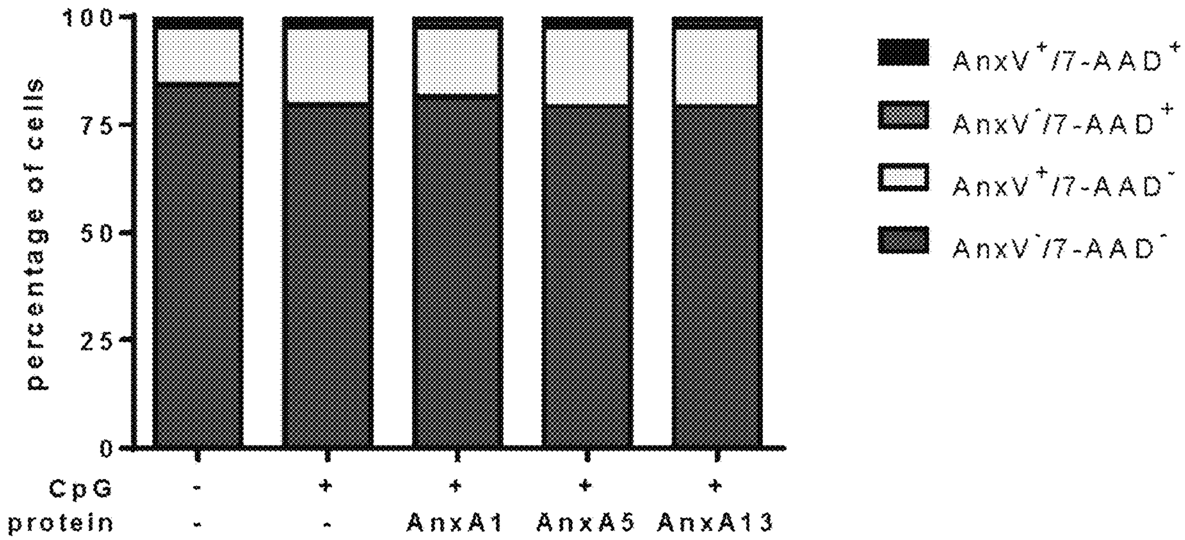

AnxA5 and AnxA13-Treated BMDCs Show Impaired Upregulation of Co-Stimulatory Molecules Upon TLR-Induced DC Activation ACs and AnxA1 also regulate surface expression of co-stimulatory molecules on DCs (11, 35, 36). Therefore, the effect of recombinant AnxA5 and AnxA13 on the expression of co-regulatory and MHC molecules was investigated two days after TLR stimulation. Incubation of BMDCs with AnxA1, AnxA5 or AnxA13 did not influence surface expression of MHC class I molecules, but slightly increased expression of MHC class II molecules (FIG. 15A-B). Remarkably, AnxA1, AnxA5 and AnxA13 inhibited upregulation of the co-stimulatory molecules CD40, CD80 and CD86 upon TLR stimulation (FIG. 15C-E). In contrast, surface expression of the co-inhibitory molecules programmed cell death 1 ligand 1 (PD-L1) and PD-L2 as well as cell viability of BMDCs were not affected (FIG. 15F-H). In summary, AnxA1, AnxA5 and AnxA13 impair TLR-induced upregulation of co-stimulatory molecules without affecting surface expression of co-inhibitory and MHC molecules.

FPR Family Members are not Required for DC Tolerization by AnxA5 and AnxA13

Figure 16A:
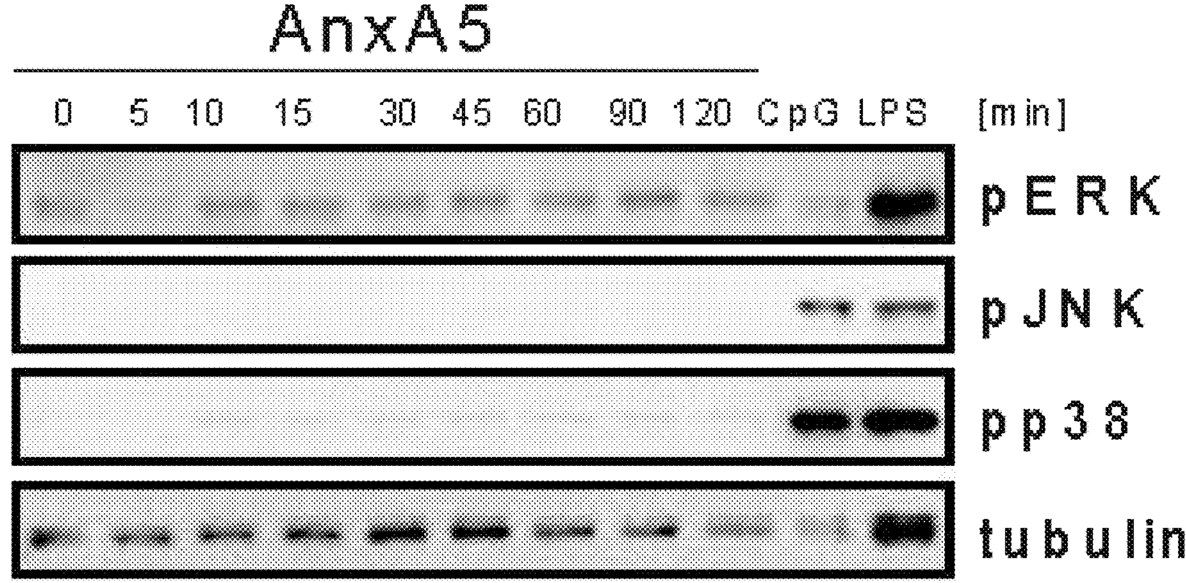
Figure 16B:
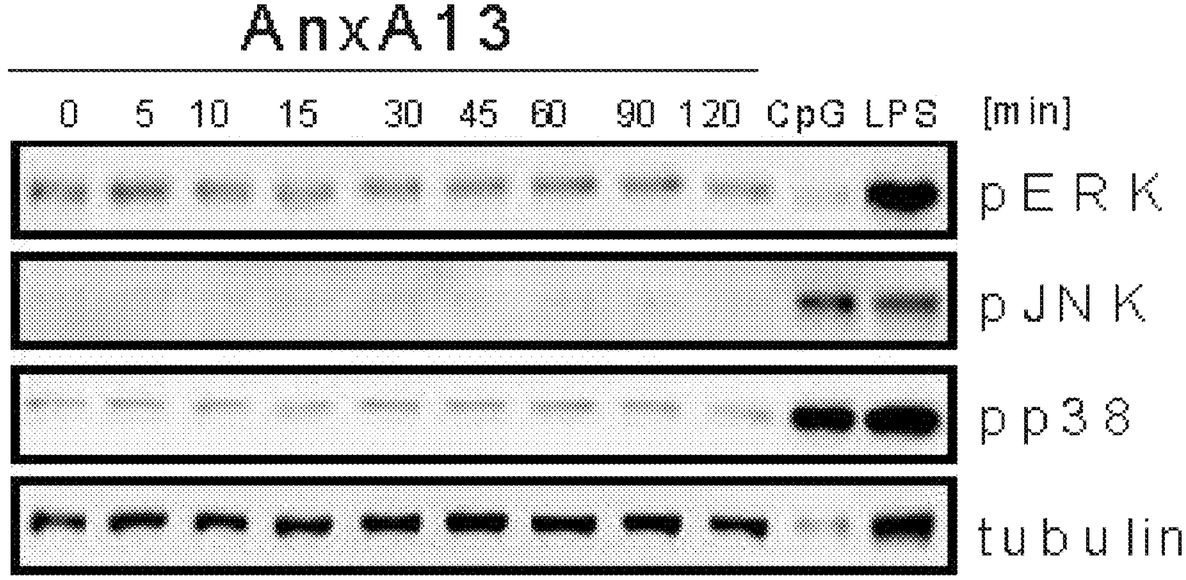
Figure 16C:
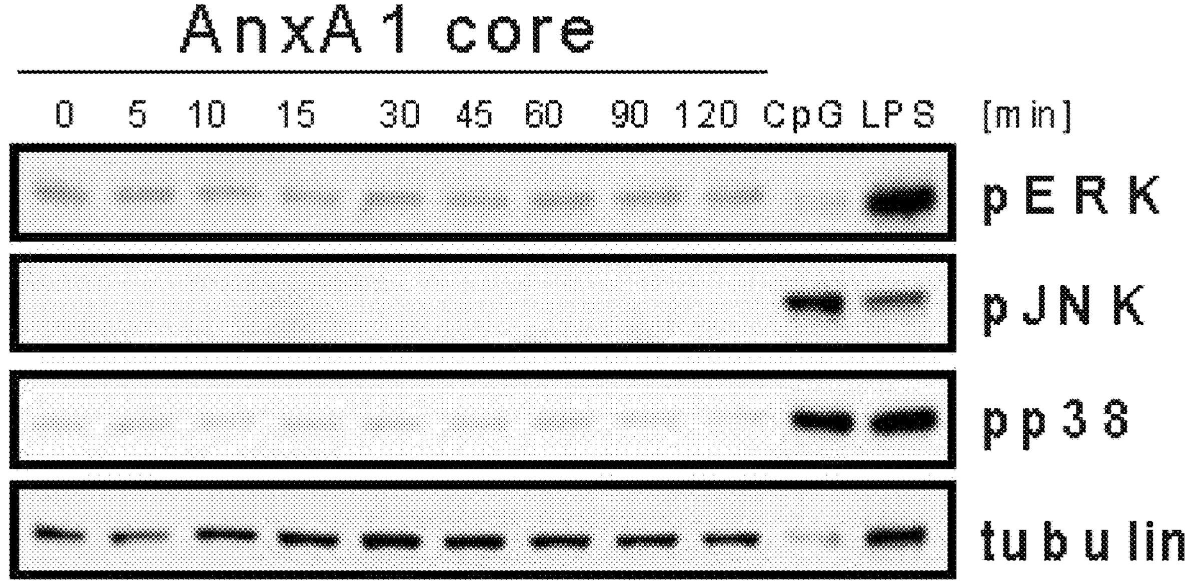
Figure 16D:
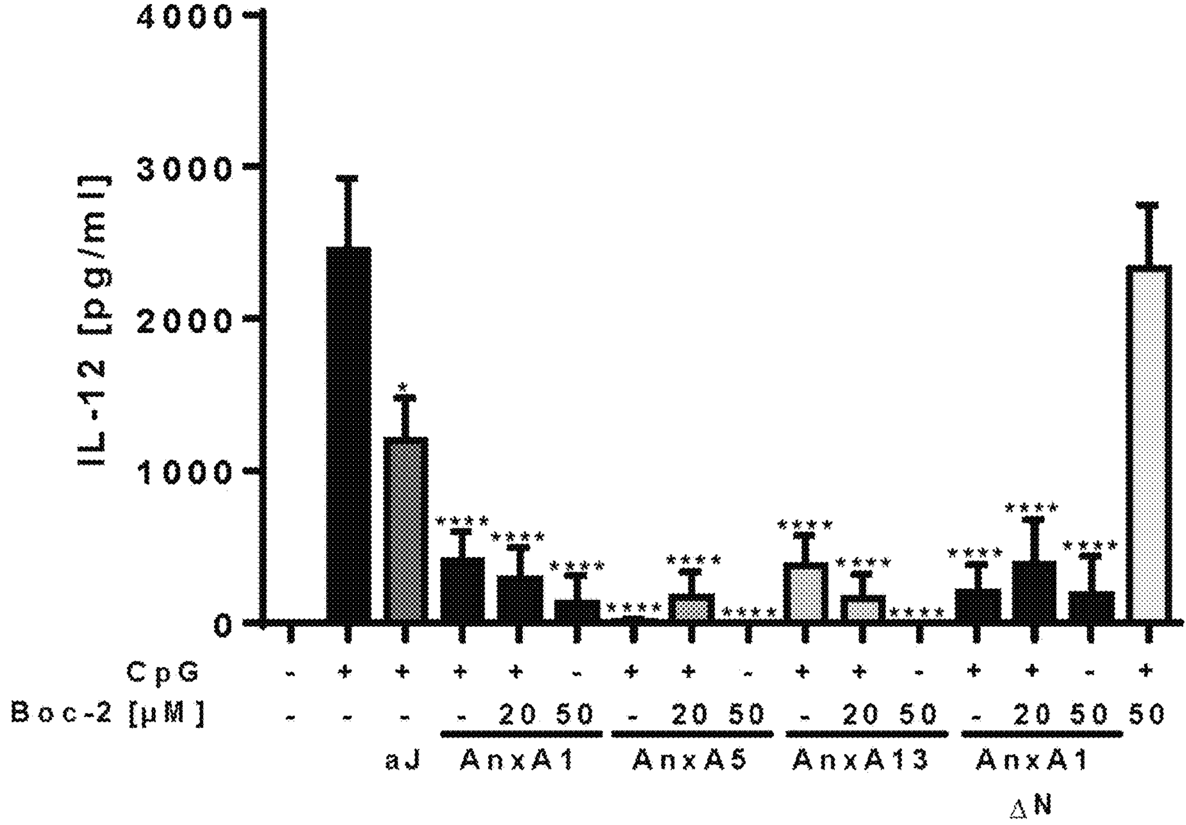

The phenotype of BMDCs incubated with AnxA5 or AnxA13 resembles the one induced by AnxA1. Therefore, the inventors next tested whether recognition of AnxA5, AnxA13 or of the AnxA1 core domain is also independent of FPR family members. Indeed, analysis of MAPK activation revealed that MAPK were not activated in BMDCs after incubation with AnxA5 and AnxA13 (FIG. 16A). Furthermore, the pan-specific FPR antagonist Boc-2 did not abrogate inhibition of TLR-induced pro-inflammatory cytokine secretion by AnxA5 and AnxA13 (FIG. 16B). In conclusion, AnxA1, AnxA5 and AnxA13 induce the development of DCs with a tolerogenic phenotype as characterized by low expression of co-stimulatory molecules and low pro-inflammatory cytokine secretion independent of FPR signaling.

AnxA5 and AnxA13 Suppress CD8$^+$ T Cell Immune Responses In Vivo

Several annexins translocate to the surface of ACs to promote the development of tolerogenic DCs, and annexin single knockout mice lack a severe phenotype. Therefore, the inventors hypothesized that annexins are redundant tolerogenic signals in vivo. Thus, deletion of AnxA1 should neither impair suppressive effects of ACs on AC-treated BMDCs nor provoke autoimmunity against self-antigens derived from ACs. In fact, absence of AnxA1 does not lead to an altered phenotype of BMDCs after AC engulfment. Apoptotic neutrophils or splenocytes from WT and AnxA1$^{-/-}$ mice suppressed TLR-induced TNF-$\alpha$ secretion by BMDCs to a comparable extent. The level of suppression increased with an elevated ratio of AC to BMDCs as seen with apoptotic Jurkat T cells, which served as a positive control (FIG. 17A). Importantly, neutrophils and splenocytes from WT and AnxA1$^{-/-}$ mice showed no difference in apoptosis kinetics upon irradiation with UV-C. Next, AnxA1$^{-/-}$ mice were analyzed for signs of autoimmunity.

CD62L/CD44 surface expression of different splenic T cell populations was comparable between WT and AnxA1$^{-/-}$ mice, indicating that there was no change in the activation status of peripheral T cells. In contrast, lymphoproliferation (lpr) mice, which served as a positive control for the development of systemic autoimmunity, clearly showed enhanced activation of splenic T cells. Furthermore, splenomegaly and lymphadenopathy were absent in 5-6-month-old AnxA1$^{-/-}$ mice. In conclusion, the lack of autoimmunity in AnxA1$^{-/-}$ mice, and the unaltered suppressive capacity of ACs from AnxA1$^{-/-}$ mice indicated that AnxA5 and AnxA13 might substitute for the loss of AnxA1 and might act as tolerogenic signals in vivo.

The inventors' group recently showed that AnxA1 restrains the function and reduces the frequency of antigen-specific CD8$^+$ T cells upon immunization of mice with xenogeneic apopotic cells ectopically expressing AnxA1 (11). To investigate whether AnxA5 and AnxA13 also regulate induction of antigen-specific T cell responses in vivo, apoptotic S2 cells expressing the model antigen Ovalbumin were injected into mice and the anti-OVA T cell response was monitored. Injection of apoptotic S2-mOVA induced a cell-mediated immune response and led to the development of OVA-specific CD8$^+$ T cells (FIG. 17B). Notably, co-injection of apoptotic S2 cells overexpressing either AnxA1, AnxA5 or AnxA13 strongly inhibited the development of OVA-specific CD8$^+$ T cells (FIG. 17B). Thus, AnxA5 and AnxA13 negatively regulate the induction of antigen-specific CD8$^+$ T cell responses and therefore act as tolerogenic signals also in vivo.

REFERENCES AS CITED

1. Mueller, D. L. 2010. Mechanisms maintaining peripheral tolerance. *Nat Immunol* 11: 21-27.
2. Huang, F. P., N. Platt, M. Wykes, J. R. Major, T. J. Powell, C. D. Jenkins, and G. G. MacPherson. 2000. A discrete subpopulation of dendritic cells transports apoptotic intestinal epithelial cells to T cell areas of mesenteric lymph nodes. *J Exp Med* 191: 435-444.
3. Gregory, C. D., and A. Devitt. 2004. The macrophage and the apoptotic cell: an innate immune interaction viewed simplistically? *Immunology* 113: 1-14.
4. Bedoui, S., P. G. Whitney, J. Waithman, L. Eidsmo, L. Wakim, I. Caminschi, R. S. Allan, M. Wojtasiak, K. Shortman, F. R. Carbone, A. G. Brooks, and W. R. Heath. 2009. Cross-presentation of viral and self antigens by skin-derived CD103+ dendritic cells. *Nat Immunol* 10: 488-495.
5. Bursch, L. S., L. Wang, B. Igyarto, A. Kissenpfennig, B. Malissen, D. H. Kaplan, and K. A. Hogquist. 2007. Identification of a novel population of Langerin+ dendritic cells. *J Exp Med* 204: 3147-3156.
6. del Rio, M. L., J. I. Rodriguez-Barbosa, E. Kremmer, and R. Forster. 2007. CD103− and CD103+ bronchial lymph node dendritic cells are specialized in presenting and cross-presenting innocuous antigen to CD4+ and CD8+ T cells. *J Immunol* 178: 6861-6866.

7. A-Gonzalez, N., S. J. Bensinger, C. Hong, S. Beceiro, M. N. Bradley, N. Zelcer, J. Deniz, C. Ramirez, M. Diaz, G. Gallardo, C. R. de Galarreta, J. Salazar, F. Lopez, P. Edwards, J. Parks, M. Andujar, P. Tontonoz, and A. Castrillo. 2009. Apoptotic cells promote their own clearance and immune tolerance through activation of the nuclear receptor LXR. *Immunity* 31: 245-258.
8. Scott, R. S., E. J. McMahon, S. M. Pop, E. A. Reap, R. Caricchio, P. L. Cohen, H. S. Earp, and G. K. Matsushima. 2001. Phagocytosis and clearance of apoptotic cells is mediated by MER. *Nature* 411: 207-211.
9. Kawane, K., M. Ohtani, K. Miwa, T. Kizawa, Y. Kanbara, Y. Yoshioka, H. Yoshikawa, and S. Nagata. 2006. Chronic polyarthritis caused by mammalian DNA that escapes from degradation in macrophages. *Nature* 443: 998-1002.
10. Wallet, M. A., P. Sen, R. R. Flores, Y. Wang, Z. Yi, Y. Huang, C. E. Mathews, H. S. Earp, G. Matsushima, B. Wang, and R. Tisch. 2008. MerTK is required for apoptotic cell-induced T cell tolerance. *J Exp Med* 205: 219-232.
11. Weyd, H., L. Abeler-Dorner, B. Linke, A. Mahr, V. Jahndel, S. Pfrang, M. Schnolzer, C. S. Falk, and P. H. Krammer. 2013. Annexin A1 on the surface of early apoptotic cells suppresses CD8+ T cell immunity. *PloS one* 8: e62449.
12. Gerke, V., and S. E. Moss. 2002. Annexins: from structure to function. *Physiol Rev* 82: 331-371.
13. Moss, S. E., and R. O. Morgan. 2004. The annexins. *Genome Biol* 5: 219.
14. Raynal, P., and H. B. Pollard. 1994. Annexins: the problem of assessing the biological role for a gene family of multifunctional calcium- and phospholipid-binding proteins. *Biochim Biophys Acta* 1197: 63-93.
15. Walther, A., K. Riehemann, and V. Gerke. 2000. A novel ligand of the formyl peptide receptor: annexin I regulates neutrophil extravasation by interacting with the FPR. *Mol Cell* 5: 831-840.
16. Ernst, S., C. Lange, A. Wilbers, V. Goebeler, V. Gerke, and U. Rescher. 2004. An annexin 1 N-terminal peptide activates leukocytes by triggering different members of the formyl peptide receptor family. *J Immunol* 172: 7669-7676.
17. Strausbaugh, H. J., and S. D. Rosen. 2001. A potential role for annexin 1 as a physiologic mediator of glucocorticoid-induced L-selectin shedding from myeloid cells. *J Immunol* 166: 6294-6300.
18. Perretti, M., and J. Dalli. 2009. Exploiting the Annexin A1 pathway for the development of novel anti-inflammatory therapeutics. *Br J Pharmacol* 158: 936-946.
19. Hayhoe, R. P., A. M. Kamal, E. Solito, R. J. Flower, D. Cooper, and M. Perretti. 2006. Annexin 1 and its bioactive peptide inhibit neutrophil-endothelium interactions under flow: indication of distinct receptor involvement. *Blood* 107: 2123-2130.
20. Pupjalis, D., J. Goetsch, D. J. Kottas, V. Gerke, and U. Rescher. 2011. Annexin A1 released from apoptotic cells acts through formyl peptide receptors to dampen inflammatory monocyte activation via JAK/STAT/SOCS signalling. *EMBO molecular medicine* 3: 102-114.
21. Wallner, B. P., R. J. Mattaliano, C. Hession, R. L. Cate, R. Tizard, L. K. Sinclair, C. Foeller, E. P. Chow, J. L. Browing, K. L. Ramachandran, and et al. 1986. Cloning and expression of human lipocortin, a phospholipase A2 inhibitor with potential anti-inflammatory activity. *Nature* 320: 77-81.
22. Davidson, F. F., M. D. Lister, and E. A. Dennis. 1990. Binding and inhibition studies on lipocortins using phosphatidylcholine vesicles and phospholipase A2 from snake venom, pancreas, and a macrophage-like cell line. *J Biol Chem* 265: 5602-5609.
23. Kim, S. W., H. J. Rhee, J. Ko, Y. J. Kim, H. G. Kim, J. M. Yang, E. C. Choi, and D. S. Na. 2001. Inhibition of cytosolic phospholipase A2 by annexin I. Specific interaction model and mapping of the interaction site. *J Biol Chem* 276: 15712-15719.
24. Kamal, A. M., R. P. Hayhoe, A. Paramasivam, D. Cooper, R. J. Flower, E. Solito, and M. Perretti. 2006. Antiflammin-2 activates the human formyl-peptide receptor like 1. *Scientific World Journal* 6: 1375-1384.

25. Farber, S. A., R. A. De Rose, E. S. Olson, and M. E. Halpern. 2003. The zebrafish annexin gene family. *Genome Res* 13: 1082-1096.
26. Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte/macrophage colony-stimulating factor. *J Exp Med* 176: 1693-1702.
27. Naik, S. H., A. I. Proietto, N. S. Wilson, A. Dakic, P. Schnorrer, M. Fuchsberger, M. H. Lahoud, M. O'Keeffe, Q. X. Shao, W. F. Chen, J. A. Villadangos, K. Shortman, and L. Wu. 2005. Cutting edge: generation of splenic CD8+ and CD8− dendritic cell equivalents in Fms-like tyrosine kinase 3 ligand bone marrow cultures. *J Immunol* 174: 6592-6597.
28. Brachvogel, B., J. Dikschas, H. Moch, H. Welzel, K. von der Mark, C. Hofmann, and E. Poschl. 2003. Annexin A5 is not essential for skeletal development. *Mol Cell Biol* 23: 2907-2913.
29. Hawkins, T. E., J. Roes, D. Rees, J. Monkhouse, and S. E. Moss. 1999. Immunological development and cardiovascular function are normal in annexin VI null mutant mice. *Mol Cell Biol* 19: 8028-8032.
30. Herr, C., N. Smyth, S. Ullrich, F. Yun, P. Sasse, J. Hescheler, B. Fleischmann, K. Lasek, K. Brixius, R. H. Schwinger, R. Fassler, R. Schroder, and A. A. Noegel. 2001. Loss of annexin A7 leads to alterations in frequency-induced shortening of isolated murine cardiomyocytes. *Mol Cell Biol* 21: 4119-4128.
31. Ling, Q., A. T. Jacovina, A. Deora, M. Febbraio, R. Simantov, R. L. Silverstein, B. Hempstead, W. H. Mark, and K. A. Hajjar. 2004. Annexin II regulates fibrin homeostasis and neoangiogenesis in vivo. *J Clin Invest* 113: 38-48.
32. Hannon, R., J. D. Croxtall, S. J. Getting, F. Roviezzo, S. Yona, M. J. Paul-Clark, F. N. Gavins, M. Perretti, J. F. Morris, J. C. Buckingham, and R. J. Flower. 2003. Aberrant inflammation and resistance to glucocorticoids in annexin 1−/− mouse. *FASEB J* 17: 253-255.
33. Iglesias, J. M., R. O. Morgan, N. A. Jenkins, N. G. Copeland, D. J. Gilbert, and M. P. Fernandez. 2002. Comparative genetics and evolution of annexin A13 as the founder gene of vertebrate annexins. *Mol Biol Evol* 19: 608-618.
34. Iyoda, T., S. Shimoyama, K. Liu, Y. Omatsu, Y. Akiyama, Y. Maeda, K. Takahara, R. M. Steinman, and K. Inaba. 2002. The CD8+ dendritic cell subset selectively endocytoses dying cells in culture and in vivo. *J Exp Med* 195: 1289-1302.
35. Ip, W. K., and Y. L. Lau. 2004. Distinct maturation of, but not migration between, human monocyte-derived dendritic cells upon ingestion of apoptotic cells of early or late phases. *J Immunol* 173: 189-196.

36. Stuart, L. M., M. Lucas, C. Simpson, J. Lamb, J. Savill, and A. Lacy-Hulbert. 2002. Inhibitory effects of apoptotic cell ingestion upon endotoxin-driven myeloid dendritic cell maturation. *J Immunol* 168: 1627-1635.
37. Liu, K., T. Iyoda, M. Saternus, Y. Kimura, K. Inaba, and R. M. Steinman. 2002. Immune tolerance after delivery of dying cells to dendritic cells in situ. *J Exp Med* 196: 1091-1097.
38. Skoberne, M., S. Somersan, W. Almodovar, T. Truong, K. Petrova, P. M. Henson, and N. Bhardwaj. 2006. The apoptotic-cell receptor CR3, but not alphavbeta5, is a regulator of human dendritic-cell immunostimulatory function. *Blood* 108: 947-955.
39. Urban, B. C., N. Willcox, and D. J. Roberts. 2001. A role for CD36 in the regulation of dendritic cell function. *Proc Natl Acad Sci USA* 98: 8750-8755.
40. Krispin, A., Y. Bledi, M. Atallah, U. Trahtemberg, I. Verbovetski, E. Nahari, O. Zelig, M. Linial, and D. Mevorach. 2006. Apoptotic cell thrombospondin-1 and heparin-binding domain lead to dendritic-cell phagocytic and tolerizing states. *Blood* 108: 3580-3589.
41. Adler, A. J., D. W. Marsh, G. S. Yochum, J. L. Guzzo, A. Nigam, W. G. Nelson, and D. M. Pardoll. 1998. CD4+ T cell tolerance to parenchymal self-antigens requires presentation by bone marrow-derived antigen-presenting cells. *J Exp Med* 187: 1555-1564.
42. Akbari, O., R. H. DeKruyff, and D. T. Umetsu. 2001. Pulmonary dendritic cells producing IL-10 mediate tolerance induced by respiratory exposure to antigen. *Nat Immunol* 2: 725-731.
43. Hawiger, D., K. Inaba, Y. Dorsett, M. Guo, K. Mahnke, M. Rivera, J. V. Ravetch, R. M. Steinman, and M. C. Nussenzweig. 2001. Dendritic cells induce peripheral T cell unresponsiveness under steady state conditions in vivo. *J Exp Med* 194: 769-779.
44. Janssen, E. M., N. M. Droin, E. E. Lemmens, M. J. Pinkoski, S. J. Bensinger, B. D. Ehst, T. S. Griffith, D. R. Green, and S. P. Schoenberger. 2005. CD4+ T-cell help controls CD8+ T-cell memory via TRAIL-mediated activation-induced cell death. *Nature* 434: 88-93.
45. Kawahata, K., Y. Misaki, M. Yamauchi, S. Tsunekawa, K. Setoguchi, J. Miyazaki, and K. Yamamoto. 2002. Generation of CD4(+)CD25(+) regulatory T cells from autoreactive T cells simultaneously with their negative selection in the thymus and from nonautoreactive T cells by endogenous TCR expression. *J Immunol* 168: 4399-4405.
46. Probst, H. C., K. McCoy, T. Okazaki, T. Honjo, and M. van den Broek. 2005. Resting dendritic cells induce peripheral CD8+ T cell tolerance through PD-1 and CTLA-4. *Nat Immunol* 6: 280-286.
47. Monceau, V., Y. Belikova, G. Kratassiouk, D. Charue, E. Camors, C. Communal, P. Trouve, F. Russo-Marie, and D. Charlemagne. 2004. Externalization of endogenous annexin A5 participates in apoptosis of rat cardiomyocytes. *Cardiovasc Res* 64: 496-506.
48. Kaneko, N., R. Matsuda, S. Hosoda, T. Kajita, and Y. Ohta. 1996. Measurement of plasma annexin V by ELISA in the early detection of acute myocardial infarction. *Clin Chim Acta* 251: 65-80.
49. Matsuda, R., N. Kaneko, Y. Horikawa, F. Chiwaki, M. Shinozaki, T. Ieiri, T. Suzuki, and N. Ogawa. 2001. Localization of annexin V in rat normal kidney and experimental glomerulonephritis. *Res Exp Med* (*Berl*) 200: 77-92.
50. Sen, P., M. A. Wallet, Z. Yi, Y. Huang, M. Henderson, C. E. Mathews, H. S. Earp, G. Matsushima, A. S. Baldwin, Jr., and R. M. Tisch. 2007. Apoptotic cells induce Mer tyrosine kinase-dependent blockade of NF-kappaB activation in dendritic cells. *Blood* 109: 653-660.
51. Verbovetski, I., H. Bychkov, U. Trahtemberg, I. Shapira, M. Hareuveni, O. Ben-Tal, I. Kutikov, O. Gill, and D. Mevorach. 2002. Opsonization of apoptotic cells by autologous iC3b facilitates clearance by immature dendritic cells, down-regulates DR and CD86, and up-regulates CC chemokine receptor 7. *J Exp Med* 196: 1553-1561.
52. Voll, R. E., M. Herrmann, E. A. Roth, C. Stach, J. R. Kalden, and I. Girkontaite. 1997. Immunosuppressive effects of apoptotic cells. *Nature* 390: 350-351.
53. Fujii, S., K. Liu, C. Smith, A. J. Bonito, and R. M. Steinman. 2004. The linkage of innate to adaptive immunity via maturing dendritic cells in vivo requires CD40 ligation in addition to antigen presentation and CD80/86 costimulation. *J Exp Med* 199: 1607-1618.
54. Joffre, O., M. A. Nolte, R. Sporri, and C. Reis e Sousa. 2009. Inflammatory signals in dendritic cell activation and the induction of adaptive immunity. *Immunol Rev* 227: 234-247.
55. Serhan, C. N., S. D. Brain, C. D. Buckley, D. W. Gilroy, C. Haslett, L. A. O'Neill, M. Perretti, A. G. Rossi, and J. L. Wallace. 2007. Resolution of inflammation: state of the art, definitions and terms. *FASEB J* 21: 325-332.
56. Serhan, C. N., J. Z. Haeggstrom, and C. C. Leslie. 1996. Lipid mediator networks in cell signaling: update and impact of cytokines. *FASEB J* 10: 1147-1158.
57. Kim, K. M., D. K. Kim, Y. M. Park, C. K. Kim, and D. S. Na. 1994. Annexin-I inhibits phospholipase A2 by specific interaction, not by substrate depletion. *FEBS Lett* 343: 251-255.
58. Solito, E., A. Mulla, J. F. Morris, H. C. Christian, R. J. Flower, and J. C. Buckingham. 2003. Dexamethasone induces rapid serine-phosphorylation and membrane translocation of annexin 1 in a human folliculostellate cell line via a novel nongenomic mechanism involving the glucocorticoid receptor, protein kinase C, phosphatidylinositol 3-kinase, and mitogen-activated protein kinase. *Endocrinology* 144: 1164-1174.
59. Solito, E., C. de Coupade, S. Canaider, N. J. Goulding, and M. Perretti. 2001. Transfection of annexin 1 in monocytic cells produces a high degree of spontaneous and stimulated apoptosis associated with caspase-3 activation. *Br J Pharmacol* 133: 217-228.
60. Solito, E., A. Kamal, F. Russo-Marie, J. C. Buckingham, S. Marullo, and M. Perretti.

2003. A novel calcium-dependent proapoptotic effect of annexin 1 on human neutrophils. *FASEB J* 17: 1544-1546.

61. Gidon-Jeangirard, C., E. Solito, A. Hofmann, F. Russo-Marie, J. M. Freyssinet, and M. C. Martinez. 1999. Annexin V counteracts apoptosis while inducing Ca(2+) influx in human lymphocytic T cells. *Biochem Biophys Res Commun* 265: 709-715.
62. Miele, L., E. Cordella-Miele, A. Facchiano, and A. B. Mukherjee. 1988. Novel anti-inflammatory peptides from the region of highest similarity between uteroglobin and lipocortin I. *Nature* 335: 726-730.

63. Perretti, M., N. Chiang, M. La, I. M. Fierro, S. Marullo, S. J. Getting, E. Solito, and C. N. Serhan. 2002. Endogenous lipid- and peptide-derived anti-inflammatory pathways generated with glucocorticoid and aspirin treatment activate the lipoxin A4 receptor. *Nat Med* 8: 1296-1302.
64. Haynes, N. M., R. G. van der Most, R. A. Lake, and M. J. Smyth. 2008. Immunogenic anti-cancer chemotherapy as an emerging concept. *Curr Opin Immunol* 20: 545-557.
65. van der Most, R. G., A. J. Currie, B. W. Robinson, and R. A. Lake. 2008. Decoding dangerous death: how cytotoxic chemotherapy invokes inflammation, immunity or nothing at all. *Cell Death Differ* 15: 13-20.
66. Garg, A. D., D. Nowis, J. Golab, P. Vandenabeele, D. V. Krysko, and P. Agostinis. 2010. Immunogenic cell death, DAMPs and anticancer therapeutics: an emerging amalgamation. *Biochim Biophys Acta* 1805: 53-71.

What is claimed is:

1. A method for identifying a compound that specifically interferes with an extracellular binding interaction between an annexin core domain and a cell surface receptor selected from the group consisting of a Dectin-1 receptor and lipoprotein receptor-related protein-1 (LRP-1), said method comprising:

a) contacting the annexin core domain and said receptor with a compound that interferes with the extracellular binding interaction of said annexin core domain with said receptor, and b) identifying a specific interference of said extracellular binding interaction between said annexin core domain and said receptor in the presence of said compound, as compared to said extracellular binding interaction in the absence of said compound, as detected by using a method selected from rtPCR, flow cytometry, ELISA, ELISpot, quartz crystal microbalance, immunoprecipitation and measuring an induction or reduction of translocation of said annexin core domain to an outer cell membrane and/or apoptosis in a cell expressing the annexin core domain, wherein said annexin core domain is selected from the group consisting of an annexin 1 core domain, an annexin 5 core domain, and an annexin 13 core domain.

2. The method according to claim 1, wherein said receptor is Dectin-1.

3. The method according to claim 1, wherein said interference comprises a decrease or an increase in an activity selected from the group consisting of (a) expression of said annexin, (b) binding of said annexin to said receptor, (c) annexin-mediated immunosuppression, and (d) phagocytosis of apoptotic cells.

4. The method according to claim 1, wherein said compound is selected from the group consisting of a peptide, a small molecule, an antisense oligonucleotide, an siRNA, an mRNA, and an antibody, and wherein said compound specifically interferes with binding of the annexin core domain to said receptor.

5. The method according to claim 1, wherein said annexin core domain is an annexin 1 core domain.

6. The method according to claim 5, wherein said annexin 1 core domain comprises an amino acid sequence according to SEQ ID NO. 1 or SEQ ID NO. 6.

7. The method according to claim 1, wherein said annexin core domain is an annexin 5 core domain.

8. The method according to claim 7, wherein said annexin 5 core domain comprises an amino acid sequence according to SEQ ID NO. 2 or SEQ ID NO. 7.

9. The method according to claim 1, wherein said annexin core domain is an annexin 13 core domain.

10. The method according to claim 9, wherein said annexin 13 core domain comprises an amino acid sequence according to SEQ ID NO. 3 or SEQ ID NO. 8.

11. A method for identifying a compound that specifically interferes with a binding interaction between an annexin core domain on a cell recombinantly expressing the annexin core domain and a receptor, said method comprising:

a) contacting the cell recombinantly expressing the annexin core domain, and the receptor with a compound that specifically interferes with the binding interaction between said annexin core domain and said receptor, and (b) detecting a specific interference of the binding interaction between said annexin core domain and said receptor in the presence of said compound as compared to said binding interaction in the absence of said compound as detected by using a method selected from rtPCR, flow cytometry, ELISA, ELISpot, quartz crystal microbalance, immunoprecipitation and measuring an induction or reduction of translocation of said annexin core domain to an outer cell membrane of said cell and/or apoptosis in said cell, wherein said compound is identified by the detection of the specific interference of said binding interaction, wherein said annexin core domain is selected from the group consisting of an annexin 1 core domain, an annexin 5 core domain, and an annexin 13 core domain, and, wherein said receptor is selected from the group consisting of Dectin-1 receptor and LRP-1.

12. The method according to claim 11, wherein said receptor is Dectin-1.

13. The method according to claim 11, wherein said annexin core domain is an annexin 1 core domain.

14. The method according to claim 13, wherein said annexin 1 core domain comprises an amino acid sequence according to SEQ ID NO. 1 or SEQ ID NO. 6.

15. The method according to claim 11, wherein said annexin core domain is an annexin 5 core domain.

16. The method according to claim 15, wherein said annexin 5 core domain comprises an amino acid sequence according to SEQ ID NO. 2 or SEQ ID NO. 7.

17. The method according to claim 11, wherein said annexin core domain is an annexin 13 core domain.

18. The method according to claim 17, wherein said annexin 13 core domain comprises an amino acid sequence according to SEQ ID NO. 3 or SEQ ID NO. 8.

19. The method according to claim 11, wherein said interference comprises a decrease or an increase in an activity selected from the group consisting of (a) expression of said annexin, (b) binding of said annexin to said receptor, (c) annexin-mediated immunosuppression, and (d) phagocytosis of apoptotic cells.

20. The method according to claim 11, wherein said compound is selected from the group consisting of a peptide, a small molecule, an antisense oligonucleotide, an srRNA, an mRNA, and an antibody, and wherein said compound specifically interferes with binding of the annexin core domain to said receptor.

21. The method according to claim 11, wherein said cell is selected from the group consisting of a dendritic cell, a macrophage, a cancer cell, an apoptotic cell, an S2 cell, a Mono Mac cell, and a recombinant host cell.

22. The method according to claim 11, wherein said cell further expresses said receptor on the cell surface.

* * * * *

SEQUENCE LISTING

```
<160> NUMBER OF SEQ ID NOS: 8

<210> SEQ ID NO 1
<211> LENGTH: 346
<212> TYPE: PRT
<213> ORGANISM: Homo sapiens

<400> SEQUENCE: 1

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
```

```
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345


<210> SEQ ID NO 2
<211> LENGTH: 320
<212> TYPE: PRT
<213> ORGANISM: Homo sapiens

<400> SEQUENCE: 2

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320


<210> SEQ ID NO 3
<211> LENGTH: 316
```

```
<212> TYPE: PRT
<213> ORGANISM: Homo sapiens

<400> SEQUENCE: 3

Met Gly Asn Arg His Ala Lys Ala Ser Ser Pro Gln Gly Phe Asp Val
1               5                   10                  15

Asp Arg Asp Ala Lys Lys Leu Asn Lys Ala Cys Lys Gly Met Gly Thr
            20                  25                  30

Asn Glu Ala Ala Ile Ile Glu Ile Leu Ser Gly Arg Thr Ser Asp Glu
        35                  40                  45

Arg Gln Gln Ile Lys Gln Lys Tyr Lys Ala Thr Tyr Gly Lys Glu Leu
    50                  55                  60

Glu Glu Val Leu Lys Ser Glu Leu Ser Gly Asn Phe Glu Lys Thr Ala
65                  70                  75                  80

Leu Ala Leu Leu Asp His Pro Ser Glu Tyr Ala Ala Arg Gln Leu Gln
                85                  90                  95

Lys Ala Met Lys Gly Leu Gly Thr Asp Glu Ser Val Leu Ile Glu Val
            100                 105                 110

Leu Cys Thr Arg Thr Asn Lys Glu Ile Ile Ala Ile Lys Glu Ala Tyr
        115                 120                 125

Gln Arg Leu Phe Asp Arg Ser Leu Glu Ser Asp Val Lys Gly Asp Thr
    130                 135                 140

Ser Gly Asn Leu Lys Lys Ile Leu Val Ser Leu Leu Gln Ala Asn Arg
145                 150                 155                 160

Asn Glu Gly Asp Asp Val Asp Lys Asp Leu Ala Gly Gln Asp Ala Lys
                165                 170                 175

Asp Leu Tyr Asp Ala Gly Glu Gly Arg Trp Gly Thr Asp Glu Leu Ala
            180                 185                 190

Phe Asn Glu Val Leu Ala Lys Arg Ser Tyr Lys Gln Leu Arg Ala Thr
        195                 200                 205

Phe Gln Ala Tyr Gln Ile Leu Ile Gly Lys Asp Ile Glu Glu Ala Ile
    210                 215                 220

Glu Glu Glu Thr Ser Gly Asp Leu Gln Lys Ala Tyr Leu Thr Leu Val
225                 230                 235                 240

Arg Cys Ala Gln Asp Cys Glu Asp Tyr Phe Ala Glu Arg Leu Tyr Lys
                245                 250                 255

Ser Met Lys Gly Ala Gly Thr Asp Glu Glu Thr Leu Ile Arg Ile Ile
            260                 265                 270

Val Thr Arg Ala Glu Val Asp Leu Gln Gly Ile Lys Ala Lys Phe Gln
        275                 280                 285

Glu Lys Tyr Gln Lys Ser Leu Ser Asp Met Val Arg Ser Asp Thr Ser
    290                 295                 300

Gly Asp Phe Arg Lys Leu Leu Val Ala Leu Leu His
305                 310                 315


<210> SEQ ID NO 4
<211> LENGTH: 9
<212> TYPE: PRT
<213> ORGANISM: Gallus gallus

<400> SEQUENCE: 4

Ser Ile Ile Ile Asn Phe Glu Lys Leu
1               5


<210> SEQ ID NO 5
<211> LENGTH: 17
```

<212> TYPE: PRT
<213> ORGANISM: Gallus gallus

<400> SEQUENCE: 5

Ile Ser Gln Ala Val His Ala Ala His Ala Glu Ile Asn Glu Ala Gly
1               5                   10                  15

Arg

<210> SEQ ID NO 6
<211> LENGTH: 346
<212> TYPE: PRT
<213> ORGANISM: Mus musculus

<400> SEQUENCE: 6

Met Ala Met Val Ser Glu Phe Leu Lys Gln Ala Arg Phe Leu Glu Asn
1               5                   10                  15

Gln Glu Gln Glu Tyr Val Gln Ala Val Lys Ser Tyr Lys Gly Gly Pro
            20                  25                  30

Gly Ser Ala Val Ser Pro Tyr Pro Ser Phe Asn Val Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Thr Asn Ala Gln Arg Gln Gln Ile
65                  70                  75                  80

Lys Ala Ala Tyr Leu Gln Glu Asn Gly Lys Pro Leu Asp Glu Val Leu
                85                  90                  95

Arg Lys Ala Leu Thr Gly His Leu Glu Glu Val Val Leu Ala Met Leu
            100                 105                 110

Lys Thr Pro Ala Gln Phe Asp Ala Asp Glu Leu Arg Gly Ala Met Lys
        115                 120                 125

Gly Leu Gly Thr Asp Glu Asp Thr Leu Ile Glu Ile Leu Thr Thr Arg
    130                 135                 140

Ser Asn Glu Gln Ile Arg Glu Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Lys Ala Leu Leu Ala Leu Ala Lys Gly Asp Arg Cys Gln Asp Leu
            180                 185                 190

Ser Val Asn Gln Asp Leu Ala Asp Thr Asp Ala Arg Ala Leu Tyr Glu
        195                 200                 205

Ala Gly Glu Arg Arg Lys Gly Thr Asp Val Asn Val Phe Thr Thr Ile
    210                 215                 220

Leu Thr Ser Arg Ser Phe Pro His Leu Arg Arg Val Phe Gln Asn Tyr
225                 230                 235                 240

Gly Lys Tyr Ser Gln His Asp Met Asn Lys Ala Leu Asp Leu Glu Leu
                245                 250                 255

Lys Gly Asp Ile Glu Lys Cys Leu Thr Thr Ile Val Lys Cys Ala Thr
            260                 265                 270

Ser Thr Pro Ala Phe Phe Ala Glu Lys Leu Tyr Glu Ala Met Lys Gly
        275                 280                 285

Ala Gly Thr Arg His Lys Ala Leu Ile Arg Ile Met Val Ser Arg Ser
    290                 295                 300

Glu Ile Asp Met Asn Glu Ile Lys Val Phe Tyr Gln Lys Lys Tyr Gly
305                 310                 315                 320

Ile Ser Leu Cys Gln Ala Ile Leu Asp Glu Thr Lys Gly Asp Tyr Glu

```
                325                 330                 335

Lys Ile Leu Val Ala Leu Cys Gly Gly Asn
            340                 345


<210> SEQ ID NO 7
<211> LENGTH: 319
<212> TYPE: PRT
<213> ORGANISM: Mus musculus

<400> SEQUENCE: 7

Met Ala Thr Arg Gly Thr Val Thr Asp Phe Pro Gly Phe Asp Gly Arg
1               5                   10                  15

Ala Asp Ala Glu Val Leu Arg Lys Ala Met Lys Gly Leu Gly Thr Asp
            20                  25                  30

Glu Asp Ser Ile Leu Asn Leu Leu Thr Ser Arg Ser Asn Ala Gln Arg
        35                  40                  45

Gln Glu Ile Ala Gln Glu Phe Lys Thr Leu Phe Gly Arg Asp Leu Val
    50                  55                  60

Asp Asp Leu Lys Ser Glu Leu Thr Gly Lys Phe Glu Lys Leu Ile Val
65                  70                  75                  80

Ala Met Met Lys Pro Ser Arg Leu Tyr Asp Ala Tyr Glu Leu Lys His
                85                  90                  95

Ala Leu Lys Gly Ala Gly Thr Asp Glu Lys Val Leu Thr Glu Ile Ile
            100                 105                 110

Ala Ser Arg Thr Pro Glu Glu Leu Ser Ala Ile Lys Gln Val Tyr Glu
        115                 120                 125

Glu Glu Tyr Gly Ser Asn Leu Glu Asp Asp Val Val Gly Asp Thr Ser
    130                 135                 140

Gly Tyr Tyr Gln Arg Met Leu Val Val Leu Leu Gln Ala Asn Arg Asp
145                 150                 155                 160

Pro Asp Thr Ala Ile Asp Asp Ala Gln Val Glu Leu Asp Ala Gln Ala
                165                 170                 175

Leu Phe Gln Ala Gly Glu Leu Lys Trp Gly Thr Asp Glu Glu Lys Phe
            180                 185                 190

Ile Thr Ile Phe Gly Thr Arg Ser Val Ser His Leu Arg Arg Val Phe
        195                 200                 205

Asp Lys Tyr Met Thr Ile Ser Gly Phe Gln Ile Glu Glu Thr Ile Asp
    210                 215                 220

Arg Glu Thr Ser Gly Asn Leu Glu Gln Leu Leu Leu Ala Val Val Lys
225                 230                 235                 240

Ser Ile Arg Ser Ile Pro Ala Tyr Leu Ala Glu Thr Leu Tyr Tyr Ala
                245                 250                 255

Met Lys Gly Ala Gly Thr Asp Asp His Thr Leu Ile Arg Val Val Val
            260                 265                 270

Ser Arg Ser Glu Ile Asp Leu Phe Asn Ile Arg Lys Glu Phe Arg Lys
        275                 280                 285

Asn Phe Ala Thr Ser Leu Tyr Ser Met Ile Lys Gly Asp Thr Ser Gly
    290                 295                 300

Asp Tyr Lys Lys Ala Leu Leu Leu Leu Cys Gly Gly Glu Asp Asp
305                 310                 315


<210> SEQ ID NO 8
<211> LENGTH: 317
<212> TYPE: PRT
<213> ORGANISM: Mus musculus
```

-continued

```
<400> SEQUENCE: 8

Met Gly Asn Arg His Ala Lys Glu Arg Ser His His His Gly Phe Asp
1               5                   10                  15

Ala Asp Arg Asp Ala Lys Lys Leu Tyr Lys Ala Cys Lys Gly Met Gly
            20                  25                  30

Thr Asp Glu Ala Ala Ile Ile Glu Val Leu Ser Ser Arg Thr Ser Glu
        35                  40                  45

Glu Arg Gln Gln Ile Lys Gln Lys Tyr Lys Glu Lys Tyr Gly Lys Asp
    50                  55                  60

Leu Glu Glu Val Leu Asn Ser Glu Leu Ser Gly Asn Phe Lys Lys Thr
65                  70                  75                  80

Ala Leu Ala Leu Leu Asp Arg Pro Asn Glu Tyr Ala Ala Arg Gln Leu
                85                  90                  95

Gln Lys Ala Met Lys Gly Val Gly Thr Asp Glu Ala Met Leu Ile Glu
            100                 105                 110

Ile Leu Cys Thr Arg Ser Asn Lys Glu Ile Val Ala Ile Lys Glu Ala
        115                 120                 125

Tyr Gln Arg Leu Phe Gly Arg Ser Leu Glu Ser Asp Val Lys Glu Asp
    130                 135                 140

Thr Ser Gly Asn Leu Arg Lys Ile Leu Val Ser Leu Leu Gln Ala Ser
145                 150                 155                 160

Arg Asp Glu Glu Asp Thr Val Asp Lys Glu Leu Ala Gly Gln Asp Ala
                165                 170                 175

Lys Asp Leu Tyr Asp Ala Gly Glu Gly Arg Trp Gly Thr Asp Glu Leu
            180                 185                 190

Ala Phe Asn Glu Val Leu Ala Lys Arg Ser Tyr Lys Gln Leu Arg Ala
        195                 200                 205

Thr Phe Gln Ala Tyr Gln Ile Leu Ile Gly Lys Asp Met Glu Glu Thr
    210                 215                 220

Ile Glu Glu Glu Thr Ser Gly Asp Leu Lys Lys Ala Tyr Leu Thr Ile
225                 230                 235                 240

Val Arg Cys Ala Gln Asp Leu Glu Gly Tyr Phe Ala Asp Leu Leu Tyr
                245                 250                 255

Lys Ala Met Lys Gly Met Gly Thr Asp Glu Glu Thr Leu Ile Arg Ile
            260                 265                 270

Ile Val Thr Arg Ala Glu Val Asp Leu Gln Gly Ile Lys Ala Lys Phe
        275                 280                 285

Gln Glu Lys Tyr Gln Lys Ser Leu Ser Asp Met Val His Ser Asp Thr
    290                 295                 300

Ser Gly Asp Phe Arg Lys Leu Leu Val Ala Leu Leu His
305                 310                 315
```